United States Patent
Causevic et al.

(10) Patent No.: US 7,333,619 B2
(45) Date of Patent: Feb. 19, 2008

(54) FAST WAVELET ESTIMATION OF WEAK BIO-SIGNALS USING NOVEL ALGORITHMS FOR GENERATING MULTIPLE ADDITIONAL DATA FRAMES

(75) Inventors: Elvir Causevic, Ellisville, MO (US); Eldar Causevic, Ellisville, MO (US); Mladen Victor Wickerhauser, St. Louis, MO (US)

(73) Assignees: Everest Biomedical Instruments Company, Chesterfield, MO (US); Washington University, St. Louis, MO (US)

(*) Notice: Subject to any disclaimer, the term of this patent is extended or adjusted under 35 U.S.C. 154(b) by 72 days.

(21) Appl. No.: 11/420,862

(22) Filed: May 30, 2006

(65) Prior Publication Data

US 2006/0233390 A1 Oct. 19, 2006

Related U.S. Application Data

(62) Division of application No. 10/113,530, filed on Mar. 29, 2002, now Pat. No. 7,054,454.

(51) Int. Cl.
*H04B 15/00* (2006.01)
*G10L 21/02* (2006.01)
*G10L 19/14* (2006.01)

(52) U.S. Cl. .................. 381/94.1; 381/94.2; 381/94.3; 704/226; 704/211

(58) Field of Classification Search ...... 381/94.1–94.3; 704/226, 211; 600/559
See application file for complete search history.

(56) References Cited

U.S. PATENT DOCUMENTS

| | | | |
|---|---|---|---|
| 5,388,182 A | * | 2/1995 | Benedetto et al. .......... 704/205 |
| 5,781,881 A | * | 7/1998 | Stegmann .................. 704/211 |
| 6,249,749 B1 | * | 6/2001 | Tran et al. .................. 702/66 |

OTHER PUBLICATIONS

Donoho, David. De-Noising by Soft Thresholding. IEEE Transactions on Information Theory. vol. 41, No. 3. May 1995; pp. 613-627.*
Zhang,Yu et al. Doppler Ultrasound Signal Denosing Based on Wavelet Frames. IEEE Transactions on Ultrasonics, Ferroelectronics, and Frequency Control, vol. 48, No. 3, May 2001; pp. 709-716.*
Coifman, R.R. et al. Adapted Waveform De-Noising: for Medical Signals and IMages. IEEE Enginnering in Medicine and Bilogy. IEEE, vol. 14, Issue 5, Sep./Oct. 1995; pp. 578-586.*
Izowrski, R. et al. Nonlinear Processing of Auditory Brainstem Response. 2001 Proceedings of the 23rd Annual EMBS International Conference, Oct. 25-28, Istanbul, Turkey, pp. 1773-1776.*

* cited by examiner

*Primary Examiner*—Vivian Chin
*Assistant Examiner*—Devona E Faulk
(74) *Attorney, Agent, or Firm*—Thompson Coburn LLP; Matthew A. Rosenberg, Esq.

(57) ABSTRACT

A method and apparatus for de-noising weak bio-signals having a relatively low signal to noise ratio utilizes an iterative process of wavelet de-noising a data set comprised of a new set of frames of wavelet coefficients partially generated through a cyclic shift algorithm. The method preferably operates on a data set having $2^N$ frames, and the iteration is performed N−1 times. The resultant wavelet coefficients are then linearly averaged and an inverse discrete wavelet transform is performed to arrive at the de-noised original signal. The method is preferably carried out in a digital processor.

14 Claims, 38 Drawing Sheets

1. Original signal x[n] consisting of N=8 frames of data of n signal samples in each frame

| $f_1$ | $f_2$ | $f_3$ | $f_4$ | $f_5$ | $f_6$ | $f_7$ | $f_8$ |
|---|---|---|---|---|---|---|---|
| N ||||||||

2. Create a signal x1[1] at level k=1 by averaging frames of x[n] ($f_{12}=(f_1+f_2)/2$), and denoising

| $fd_{12}=den(f_{12},d_1)$ | $fd_{34}=den(f_{34},d_1)$ | $fd_{56}=den(f_{56},d_1)$ | $fd_{78}=den(f_{78},d_1)$ |
|---|---|---|---|
| N/2 ||||

3. Create a signal x2[n] at level k=2, by averaging adjacent frames of x1[n], and denoising

| $fd_{1234}=den(f_{1234},d_2)$ | $fd_{5678}=den(f_{5678},d_2)$ |
|---|---|
| N/4 ||

4. Create a signal x3[n] at level k=3, by averaging adjacent frames of x2[n], and denoising

| $fd_{12345678}=den(f_{12345678},d_3)$ |
|---|
| N/8=1 |

1. Original signal x[n] consisting of N=8 frames of data of n signal samples in each frame

| $f_1$ | $f_2$ | $f_3$ | $f_4$ | $f_5$ | $f_6$ | $f_7$ | $f_8$ |
|---|---|---|---|---|---|---|---|
| N ||||||||

2. Create a signal x1[1] at level k=1 by averaging frames of x[n] ($f_{12}=(f_1+f_2)/2$), then cyclic shifting frames x[n] to create new cyclic shift averages ($f_{23}=(f_2+f_3)/2$), and denoising

| $fd_{12}$ | $fd_{34}$ | $fd_{56}$ | $fd_{78}$ | $fd_{23}$ | $fd_{45}$ | $fd_{67}$ | $fd_{81}$ |
|---|---|---|---|---|---|---|---|
| N/2 |||| N/2 ||||

3. Create a signal x2[1] at level k=2 by averaging frames of x1[n], then cyclic shifting frames x1[n] to create new cyclic shift averages, and denoising

| $fd_{1234}$ | $fd_{5678}$ | $fd_{3456}$ | $fd_{7812}$ | $fd_{2345}$ | $fd_{6781}$ | $fd_{4567}$ | $fd_{8123}$ |
|---|---|---|---|---|---|---|---|
| N/4 || N/4 || N/4 || N/4 ||

4. Create a signal x3[1] at level k=3 by averaging frames of x2[n], then cyclic shifting frames x2[n] to create new cyclic shift averages, and denoising

| $fd_{12345678}$ | $fd_{56781234}$ | $fd_{34567812}$ | $fd_{78123456}$ | $fd_{23456781}$ | $fd_{67812345}$ | $fd_{45678123}$ | $fd_{81234567}$ |
|---|---|---|---|---|---|---|---|
| N/8 | N/8 | N/8 | N/8 | N/8 | N/8 | N/8 | N/8 |

Figure 20

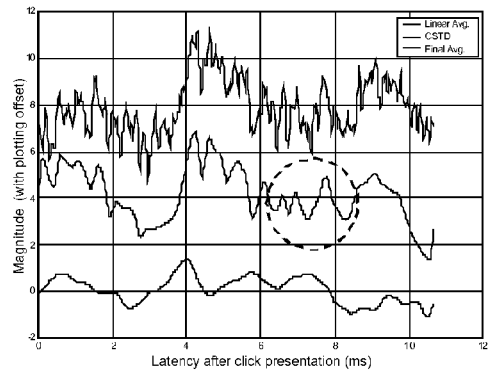
a) 32 frames
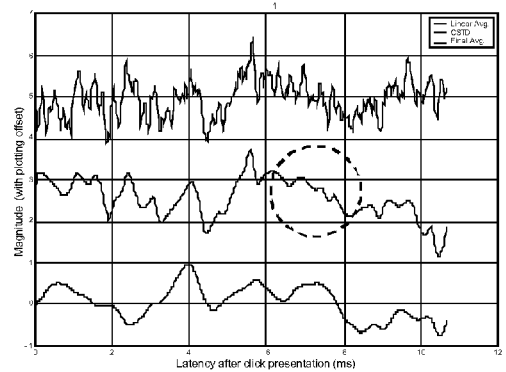
b) 128 frames
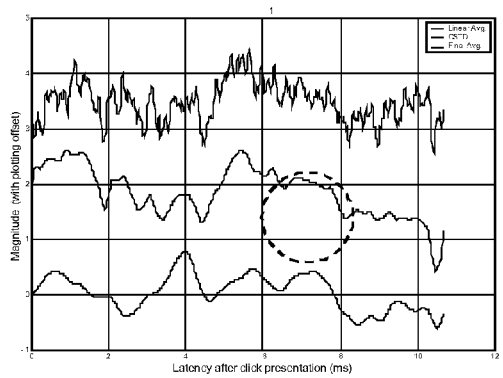
c) 256 frames
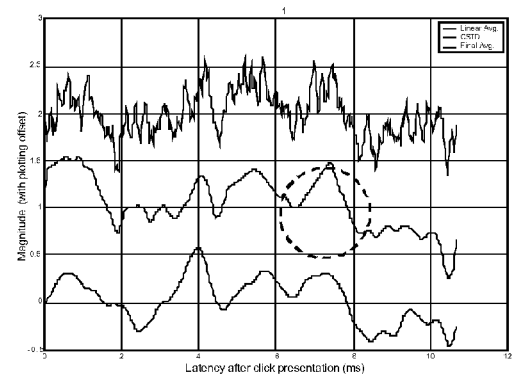
d) 512 frames
Figure 35

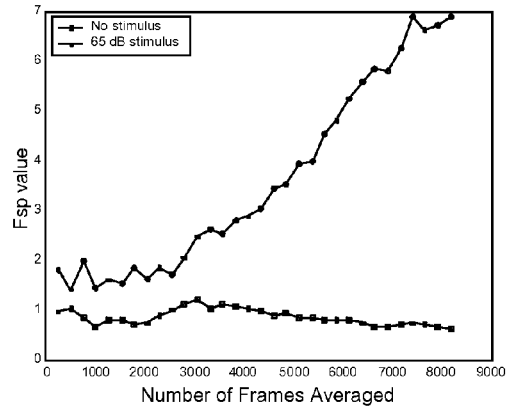
a) Ear 3
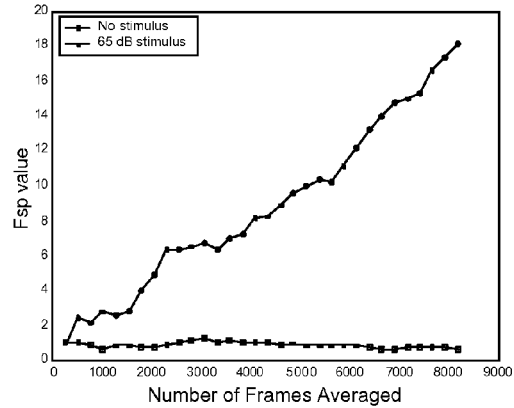
b) Ear 4
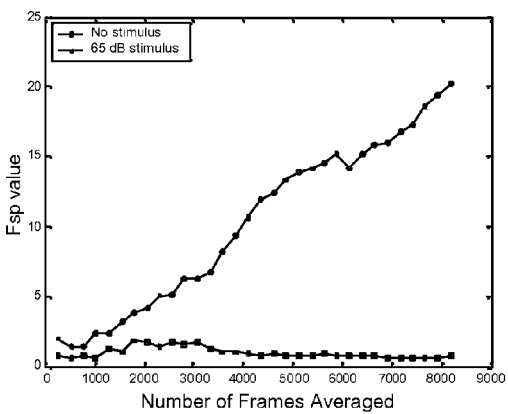
c) Ear 5
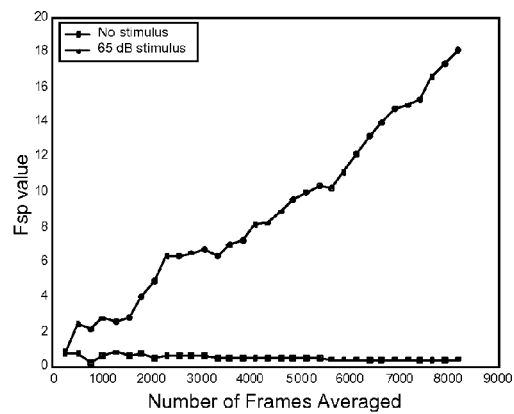
d) Ear 6
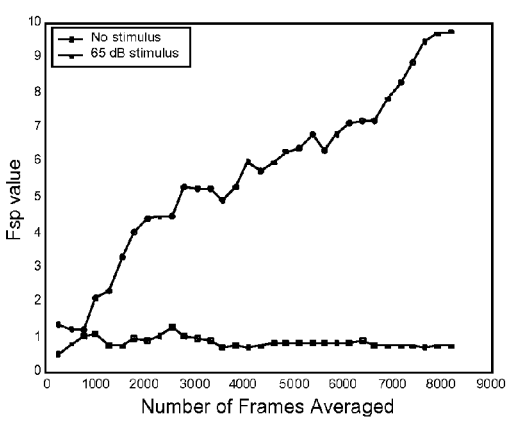
e) Ear 7
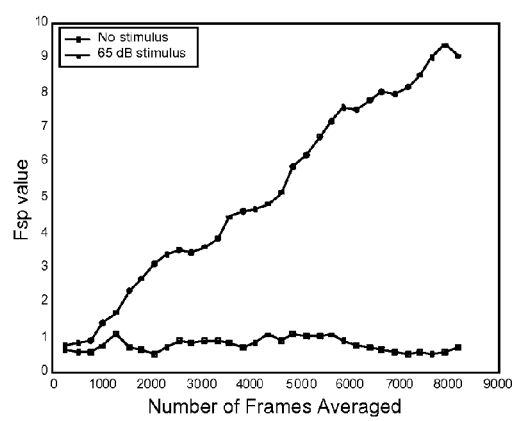
f) Ear 8
Figure 38

Figure A-6 Ear 1, CSTD (left) and variance comparison (right)

Figure A-7 Ear 2, CSTD (left) and variance comparison (right)

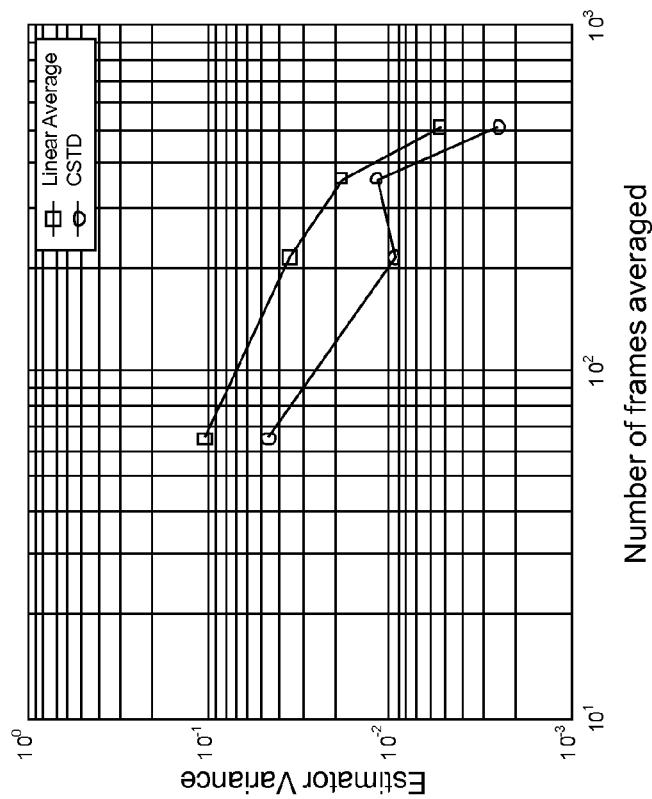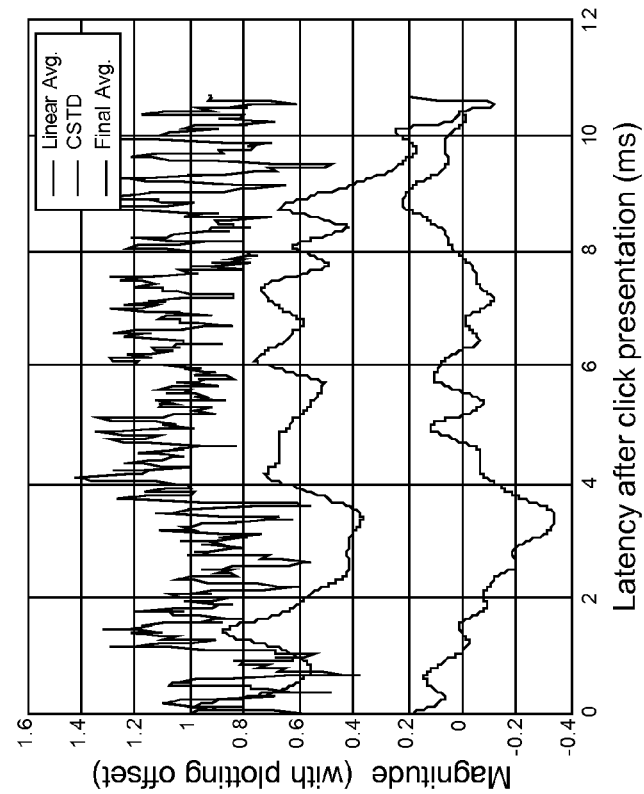
Figure 50

FAST WAVELET ESTIMATION OF WEAK BIO-SIGNALS USING NOVEL ALGORITHMS FOR GENERATING MULTIPLE ADDITIONAL DATA FRAMES

CROSS REFERENCE TO RELATED APPLICATION

This application is a divisional of application Ser. No. 10/113,530, filed Mar. 29, 2002, now U.S. Pat. No. 7,054,454.

BACKGROUND AND SUMMARY OF THE INVENTION

Accurate and rapid bio-signal acquisition and estimation is critically important in a clinical environment. In thousands of hospitals across the U.S. and the world surgeons, physicians, and other medical professionals make substantial health-related (and often life-and-death) decisions every day based on input they receive from diagnostic equipment measuring bio-signals. Many examples exist where the application of today's medical technology is hampered because the signal estimation speed allows only limited data collection, and the resulting clinical decision is based on scarce data simply because insufficient time is available for accurate bio-signal acquisition and assessment.

One example is universal neonatal hearing screening. As reported by the National Center for Hearing Assessment and Management, of the 4,000,000 infants born in the U.S. annually 12,000 have permanent hearing loss, with the average occurrence of three per 1,000. Hearing loss at birth has a higher rate of occurrence than any other birth defect. The average age of hearing loss detection without hearing screening in the U.S. is three years of age. When detected, the hearing loss can often be corrected through sound amplification using hearing aids. In the case of more severe disorders, the hearing loss can be corrected by using cochlear implants that provide direct neural stimulation of the auditory nerve. Unfortunately, when a hearing loss is not discovered until the age of three, even if it can be corrected, the formative years of language development have passed, and these children can never acquire normal speech ability for the rest of their life. Hearing impaired children are often mistakenly labeled as mentally deficient, because their speech and listening comprehension skills are not developing at the normal rate. In addition to the emotional impact of late detection, the National Institutes of Health (NIH) estimates that this costs society on the order of $500,000 dollars per child, in special education costs and lost productivity, with an overall economic impact in billions of dollars.

If the hearing loss is detected early, hearing aids can be fitted to an infant as young as four weeks, and a cochlear implant can be surgically inserted at one year of age. When the child and the parents participate in an overall intervention program that includes hearing assistive devices, parent education, special speech training, and ongoing clinical supervision, these children can develop speech ability and listening comprehension fully by the time they are school-age. This has a profound impact on their quality of life, and a very large social and economic impact on the society as a whole. As a result of the remarkable difference that early detection of hearing loss makes, 32 states in the U.S. mandate hearing tests for all infants, and other states have legislation pending or in process.

Table 1 below is listing of the abbreviations used throughout this written description.

| | |
|---|---|
| ABR | auditory brainstem response |
| ADC | analog-to-digital converter |
| AWGN | additive white Gaussian noise |
| BP | bandpass |
| C(j, k) | wavelet transform coefficients, translation (j) and dilation (k) indices |
| CRLB | Cramer Rao lower bound |
| CSTD | cyclic-shift tree de-noising |
| DAC | digital-to-analog converter |
| DWT | discrete wavelet transform |
| E{ } | expected value |
| FIR | finite impulse response (filter) |
| G, G' | high pass QMF, decomposition and reconstruction (frequency domain) |
| g, g' | high pass QMF, decomposition and reconstruction (time domain) |
| H, H' | low pass QMF, decomposition and reconstruction (frequency domain) |
| h, h' | low pass QMF, decomposition and reconstruction (time domain) |
| HP | highpass, also HPF denotes highpass filter |
| inf | infimum - greatest lower bound of a set |
| k | recombination level of cyclic shifting (number of sweeps = $2^k$) |
| $L^2$ | set of square-summable sequences |
| LP | lowpass, also LPF denotes lowpass filter |
| mod | modulo function (i.e., a mod b = c means a/b has a remainder of c) |
| MSE | mean square error |
| MVU | minimum variance unbiased (estimator) |
| N | final number of frames of ABR data |
| PDF | probability density function |
| PSD | power spectral density |
| QMF | quadrature mirror filer |
| RMS | root mean square |
| RMSE | root mean square error (defined around ABR peak V) |
| SNR | signal to noise ratio |
| sup | supremum - least upper bound of a set |
| V | finite dimensional vector space |
| var{ } | variance |
| x[n] | discrete signal indexed by n, discrete function also denoted by x |
| $\delta_k$ | de-noising threshold function dependent on cyclic shift level k |
| $\sigma^2$ | variance |
| $\{b_n\}$ | sequence indexed by n |
| $\equiv$ | congruence modulo (i.e., x $\equiv$ y mod z $\rightarrow$ x mod z = y mod z) |

To accurately and objectively measure hearing loss at birth, a cochlear acoustic test (otoacoustic emission—OAE) and an auditory brainstem response (ABR) test need to be performed, at multiple frequencies and multiple stimulus levels. An otoacoustic emission test presents tones in the ear, and measures a response to those tones coming from the cochlea. An auditory brainstem response test presents acoustical clicks in the ear, and measures the evoked electrical potentials generated by the neurons triggered in response to the acoustical stimulus. These two tests do not require a patient response, and are considered to be objective tests of hearing ability. Signals from both of these tests are completely buried in noise, with signal-to-noise ratios (SNRs) well below 0 dB. All commercially available devices performing OAE and ABR tests use linear averaging to increase the SNR of the acquired signals to the level required for accurate identification of key signal features. For an OAE test, linear averaging produces signals with SNRs large enough in under a minute per ear. Commonly OAE tests are performed at four frequencies at a single stimulus level. For an ABR test, the focus of the preferred embodiment of the invention, the linear averaging process requires a large number of frames to be acquired and averaged, resulting in overall test time of about 10 minutes for one stimulus level in one ear. As a result, the ABR test is not commonly performed on all infants being screened, but only the ones who fail the OAE test. It is also important to note that an OAE test can produce a "pass" result when the neural portion of the auditory system is damaged or completely missing. This is because the signals being measured by an OAE test are produced by the cochlea independent of the neural portion of the auditory system. Hence testing with the ABR test is imperative to get an accurate representation of hearing ability.

For the infants who do receive the ABR test, only a single ABR test at a single stimulus level is commonly performed prior to hospital discharge. As a result of this technology limitation, the NIH was forced to issue only limited recommendations for nationwide hearing screening. These include cochlear testing at a single level at only a few frequencies (3-5), and only a single level brainstem response measurement. See, National Institutes of Health, *Early Identification of hearing Impairment in Infants and Young Children*, NIH Consens Statement, March 1-3; 11(1) 1-24 (1993). Ideally, both the cochlear response and the brainstem response should be measured at 10 different frequencies, and at 10 sound levels at each frequency, in accordance with standard audiologic practice.

A substantial increase in speed of bio-signal estimation is required to overcome this problem and accurately detect the presence of hearing loss. Testing at only a few levels causes high rates of false positive (Type I error) test results. Currently, that rate is on the order of 3-15%, where only 0.3% of infants born actually have a hearing loss. At the cost of close to $1,000 for a follow up diagnostic test, on the order of 100 to 600 million dollars will be wasted annually on incorrect referrals when the program is fully implemented. Today over 50% of the infants born in the U.S. are screened at birth, currently wasting between 50 and 300 million dollars. There is also a large emotional cost to the parents of infants incorrectly identified with a hearing loss. These criticisms of neonatal hearing screening programs have been the main hindrance to its full nationwide implementation.

An additional reason why most of the children screened for hearing loss receive only the OAE test and not the ABR test is that it is economically infeasible—the equipment to conduct the ABR test costs approximately $20,000, and it only provides hearing testing at one, or at most two, hearing levels. This leaves a substantial portion of hearing impaired infants at a risk of not being detected.

Many other examples exist of clinical measurements being limited by small SNR of biosignals. These include the use of neuromonitoring during surgery to prevent nerve damage, depth of anesthesia monitoring, ototoxic drug administration, and so on, each suffering from unnecessary and potentially health threatening time delays and incomplete decision making based on scarce measurement data. The term weak bio-signal is defined to mean a signal acquired from a human body that has an SNR of preferably less than about 0 dB. These weak signals may also be found in other applications, and the present invention may just as well be used to de-noise those other weak signals. However, for purposes of illustration, the inventor has chosen the bio-signal application to represent the application of the invention.

The key obstacle in the process of weak bio-signal acquisition and estimation is the noise that corrupts the signal. The word "noise" is used herein to describe the cumulative effect of numerous sources of energy that are added to the energy of the information-bearing signal that is sought to be measured. Some of the examples of noise types corrupting bio-signals and their acquisition and processing may be found in the available literature, and include the following:

Physiological Noise:
  electrical activity (action potentials in nerves, movement of ions in/out of cells)
  blood flow (mechanical movement of fluids causing noise)
  breathing (obstructed air flow noise)
  metabolic activity (chemical)

Environmental Noise:
  Interference from power grid (50 Hz or 60 Hz depending on the country)
  Acoustic noise (equipment cooling fans, beepers, other equipment, personnel)
  Electromagnetic and radio-frequency interference from other equipment and broadcast media Bio-signal Acquisition and Processing Noise:
  Transducer-to-body interface noise (movement noise, "electrode pops")
  transducer internal noise (electrodes, microphones, temperature sensors)
  various types of electronics noise (thermal, shot, burst, avalanche noise)
  electromagnetic and RF interference from on-board digital circuitry
  arithmetic noise in digital processing (quantization, finite register length effects)

The cumulative effect of all the various noise sources often results in a combined noise magnitude significantly larger than the underlying signal. For present purposes, the cumulative effect of all the noise sources may be considered to be a single equivalent noise source. The noise from this equivalent noise source may be modeled as an additive white Gaussian noise (AWGN), a stochastic process commonly defined in the stochastic signal processing engineering literature. The term 'additive' means that the noise energy is added to the signal, as opposed to noise energy multiplying the signal. The name 'white' refers to the fact that the power spectral density is constant at all frequencies. The designation 'Gaussian' refers to the fact that the probability density function (PDF) of the noise is closely approximated by a Gaussian PDF. The noise is also assumed to be independent of the signal that is being processed. These assumptions are common in biomedical engineering and clinical literature for evoked potential signals, including the ABR. These key characteristics have been tested with the data collected from test subjects, and the results presented herein support the AWGN model.

Bio-signals, as used in this application, are signals generated by biological activity in the human body, transduced into electrical signals, and then processed to arrive at clinically valid data used by medical professionals to make clinical decisions. Most medical devices using bio-signals today are digital, hence the bio-signals are most commonly digitized and then processed digitally. Many different examples exist:
  electrocardiogram (EKG): electrical signals produced with the contractions of heart muscle
  electroencephalography (EEG): electrical signals produced by neurons creating electrical potentials
  electronystamography (ENG): electrical signals produced by vestibulo-ocular function
  respiratory flow measurement: air flow signals produced by the lungs
  blood oxygen level monitoring: optical signals produced by the transparency of the blood stream In the preferred embodiment, signals generated by the brainstem in response to auditory stimuli are analyzed utilizing a novel wavelet based noise suppression algorithm. The auditory brainstem response was chosen because it is a good example of a weak bio-signal. It is a member of the EEG class of bio-signals, occurring several milliseconds after the onset of the stimulus. The key results derived by studying ABRs are directly applicable to many weak, repetitive bio-signals.

The field of ABR recording and processing is very extensive because ABRs have found very wide applications in the clinical environment. ABRs are also known as brainstem auditory evoked potentials (BAEP or AEPs), brainstem auditory evoked responses (BAER), brainstem evoked response (BSER), as well as early or fast evoked EEG responses. A very large body of literature exists in the form of textbooks, handbooks and journal papers, in which many different uses, aspects and variations of ABRs are explored. In general, ABRs can be used for infant hearing screening, estimation of auditory sensitivity of difficult-to-test or uncooperative patients, neurodiagnosis of eighth nerve or brainstem dysfunction, and monitoring eighth nerve (i.e., acoustic nerve) and brainstem status during neurosurgery. The preferred embodiment will focus on ABRs for hearing ability detection.

Although no single official, detailed standard exists for ABR recordings, the key parameters, nomenclature, electrode placement, range of stimulus types and levels, gains and filter settings, etc. have become consistently used in a clinical environment. These conventions are widely followed in recent publications and current guidelines published by the American Academy of Audiology (AAA), the American Speech-Language-Hearing Association (ASHA), and many U.S. states' clinical processes. Certain portions of signal generation and processing are embodied in different U.S. and international standards, such as the American National Standards Institute (ANSI) and the International Electrotechnical Commission (IEC). See, IEC [International Electrotechnical Commission], "Auditory Test Signals of Short Duration or Audiometric and Neuro-otological Purposes," *International Standard IEC* 645-3, 1$^{st}$ Ed., Geneva, Switzerland (1994); ANSI [American National Standards Institute], *American National Standard Specifications for Audiometers*, [ANSI S3-6-1996], Acoustical Society of America, New York, N.Y. (1996). Hall in his "Handbook of Auditory Evoked Responses", incorporated herein by reference, gives a thorough treatment of the ABR history, current state, methods, and normative data. He also outlines the clinically accepted methods for ABR recording and interpretation through normative data. Also, Hyde in his 1998 paper "Objective detection and analysis of ABRs: An historical perspective", incorporated herein by reference, gives an excellent background of signal processing methods commonly used in ABR processing. These two works, along with numerous others, are in line with the currently accepted clinical practices and are the basis of the operation of commercially available ABR testing equipment. The data collection and analysis methods presented herein will be based on the same parameters as in these two works.

The first auditory related neural recordings were reported as early as 1929 by Berger, and 1930 by Weaver and Bray. The history of ABR recordings is very rich, beginning with a thorough description and nomenclature by Jewett and Williston in their 1971 work. From there, a variety of directions were followed with various types of stimuli, electrode placement, electrode type, processing type, etc., but they eventually converged into a single, but not entirely specific, clinical standard with some variations. ABR has been shown to be invariant under many different patient conditions (wake state, environment, time of day, etc.), and to have predictable morphology of responses across patients. It is an indicator of hearing ability, which can be measured objectively without patient response. Its amplitude is on the order of microvolts, and it is commonly contaminated by noise of the amplitude on the order of millivolts. ABRs are commonly processed by linear averaging, and the test of a response at a single stimulus level of a single ear takes approximately 5-10 minutes depending on noise conditions, quality of electrode placement, and other factors. Hence, testing at multiple levels in both ears commonly takes over an hour in a standard clinical setting. Taking over an hour to test an infant is difficult in a universal neonatal hearing screening program, because the infants are commonly only in the hospital for a short amount of time. During that short time they have to be tested for a variety of other conditions and their vital signs are continuously monitored. Another problem with long testing time arises in large metropolitan hospitals that commonly have 6,000-10,000 births per year. On average they have more than 20 infants in a nursery at any one time, and taking an hour to test each infant would require dedicated staff and multiple test devices. It would be a large and unacceptable economic burden on hospitals to require that each of these infants be screened with a test that takes over an hour. Also, the standard of care for infant health screening is that all other screening tests (PKU, sugar, etc.) take at most a few minutes. Thus, there is a long felt need to have a quick ABR test with results that are meaningful.

A typical ABR diagnostic system used for clinical and for research purposes is shown in FIG. 4. Auditory brainstem responses are evoked by presenting auditory clicks of very short duration in the ear canal. The ABR testing controller initiates click generation based on user input. Clicks are generated digitally and converted to analog voltage pulses of 100 µs duration by the digital-to-analog converter (DAC). This analog signal is fed into the speaker, which is inserted in the ear, and acoustic clicks are presented several thousand times. The click repetition rate is approximately 30-60 clicks/sec, and overall test duration is typically about 5-10 minutes.

The signal is commonly acquired using a set of three skin electrodes: one on the forehead, and one on the mastoid process behind each ear. One of the mastoid electrodes is used as a reference, while the potential between the forehead electrode and the other mastoid electrode is amplified differentially by a factor of approximately 15,000. Electrical power supply lines operating at 50 or 60 Hz, depending on the country, produce a large electrical interference signal in the ABR recording. To reduce the effects of this interference, the common mode output of the differential amplifier is inverted and fed back into the reference electrode. This creates a common mode active ground circuit, routinely used in EEG, ECG and ABR equipment. The amplified signal is converted to a digital signal using an analog-to-digital converter (ADC). The ADC contains an anti-aliasing low pass (LP) filter with a cutoff frequency at 3 kHz. The digital signal is then filtered by a digital linear phase BP filter with user selectable filter settings. Most commonly used criteria are about 30-100 Hz for the low frequency cutoff, and about 1,500-3,000 Hz for the high frequency cutoff.

The start of data acquisition is synchronized to the onset of the clicks by the ABR testing controller, and continues for a period of approximately 15 ms after each click. A single frame of data containing 15 ms of a measured response corresponds to a particular click. Several thousand acquired signal frames are then typically linearly averaged to obtain a smooth estimate of the ABR response. Each point in the final average frame is linearly averaged across each of the N frames of data. The SNR is calculated as the ratio of signal variance and noise variance. The averaging continues until the SNR exceeds a preset amount, and the system determines that a valid ABR response is present. Once a valid ABR waveform is obtained, a human expert trained in ABR interpretation (normally a state-certified audiologist) determines where the peaks are and what their latencies are, and then calculates the inter-peak latencies. They then determine whether the results are in the range of normative data for healthy subjects. If the results are not in the normative range, a pathology is declared to be present.

Over the past decade, wavelet based signal processing has emerged as a new research area in the signal processing community. The most common fields of applications of wavelets are in noise suppression (commonly referred to in the wavelet literature as "de-noising"), data compression, digital communication, system identification and others being added.

The wavelet transform, a member of the family of Fourier transforms, is a process of decomposing a given signal into a set of orthonormal basis functions called wavelets. The present invention utilizes finite length, discrete signals, so only the discrete signal transforms will be discussed.

In the traditional discrete Fourier transform (DFT), as commonly referred to in the signal processing field, the signal is decomposed using complex sinusoids as basis functions, producing a frequency domain representation of the signal. In contrast, the discrete wavelet transform (DWT) uses a family of specifically designed functions called wavelets (little waves) as basis functions. A family of wavelets is created by dilating (or "stretching") the original wavelet function called the "mother wavelet". A wavelet transform decomposes the signal in both time and frequency using different dilations of the mother wavelet. With the application of the DWT, the one-dimensional finite signal x[n] is represented in two-dimensional "wavelet coordinates". Individual levels of signal decomposition are created, called scales. At each scale, a set of coefficients is created by computing the inner product of the original signal x[n] with a scaled version of the mother wavelet. The mother wavelet function is designated by $\Psi$, and its dilations are designated by $\Psi(j)$. The position index of a wavelet at scale j is called a translation. The value of the wavelet is completely described by the two dimensional sequence $\Psi(j,k)$, where j is the scale (or stretch level) index of the wavelet, and k is the translation (or position) index. We then define the DWT as follows:

$$C(j,k) = \sum_{n=0}^{N-1} x[n]\psi_{j,k}[n],$$

where $$\psi_{j,k}[n] = 2^{\frac{j}{2}}\psi(2^{-j}n - k).$$

Coefficients $C(j,k)$ are the wavelet coefficients at different scales j and translations k of the inner product of the wavelet $\Psi(j,k)$ with the original signal x[n]. In wavelet coordinates, information about both the frequency and the location (time) of the signal energy is preserved. In traditional Fourier transform using complex exponentials time information is lost.

Conventional wavelet de-noising is a process of noise suppression that utilizes assumptions about smoothness and coherence properties of both the underlying signal and the noise that contaminates it. Similar to filtering in the frequency domain, the wavelet coefficient thresholding algorithm ("wavelet shrinkage") reduces sets of wavelet coefficients in the wavelet domain. This process is based on the assumption that the underlying signal is smooth and coherent, while the noise that is mixed with the signal is rough and incoherent. Smoothness of a signal is a property related to its bandwidth, and is defined in relation to how many times a signal can be differentiated. The degree of smoothness is equal to the number of continuous derivatives that can be calculated.

A signal is coherent if its energy is concentrated in both time and frequency domains. An incoherent noise is "spread out", and not concentrated. One measure of coherence is how many wavelet coefficients are required to represent 99% of the signal energy. A time-frequency signal space is completely spanned (covered) by wavelet coefficients at all scales and translations. A well-concentrated signal decomposed in an appropriately selected wavelet basis will require very few coefficients to represent 99% of signal energy. On the other hand, a completely incoherent noise will require 99% of the coefficients that span the entire space to represent 99% of its energy.

The conventional wavelet de-noising process is a three-step process:

1. Wavelet transform the signal to obtain wavelet coefficients at different scales
2. Threshold the coefficients and set to zero any smaller than a threshold $\delta$
3. Perform the inverse wavelet transform to approximate the original signal In the de-noising process, the noise components of the signal are attenuated by selectively setting the wavelet coefficients to zero. De-noising is thus a non-linear operation, because different coefficients are affected differently by the threshold function. There are many parameters to control in this algorithm: level of wavelet decomposition, threshold selection, using of different thresholds at different wavelet decomposition levels, scaling of wavelet coefficients that are kept by a fixed amount, and so on. However, what is common to all these variations is that in the prior art the process is performed only once, on a single signal frame.

One of the assumptions made in conventional de-noising is that the SNR of the signal being de-noised is relatively high. The algorithm relies on the fact that the amplitude of the signal is substantially larger than the amplitude of the noise, thus producing larger wavelet coefficients for the signal than for the noise. Hence, an application of conventional de-noising to small SNR signals fails as taught by the prior art.

Conventional de-noising has been demonstrated in the literature as a fast estimator of signals corrupted by noise. It operates on a single frame of the signal, by performing a single wavelet transform, setting select coefficients to zero, and then performing an inverse wavelet transform. This suggests that there are two ways to apply conventional de-noising to ABR signals, given that a single frame of data is required as an input to the algorithm. One way is to de-noise each frame individually, and then average the results. When conventional de-noising is applied to a single, un-averaged frame, thresholding the wavelet coefficients $|C(j,k)|<\delta$ to zero effectively eliminates almost all of the wavelet coefficients, including the ones representing the signal. This approach fails completely, because most of the signal energy is lost by setting the wavelet coefficient to zero. The inverse wavelet transform of the de-noised single frame wavelet coefficients produces a very low amplitude, noise only, signal.

The second way to apply conventional de-noising is to first average the individual ABR frames together to create a single averaged frame, and then de-noise that single averaged frame. This approach also leads to a substantial decrease in performance, until a very large number of frames (several thousand) are pre-averaged together. Hence conventional de-noising does not work for de-noising ABR signals when compared to linear averaging.

The present invention presents a new algorithm that may be conveniently implemented in a digital processor that utilizes information from all of the individual N frames of data and produces an estimator whose performance exceeds that of the linear averaging process. The new algorithm recombines the original low SNR data frames in a tree-like fashion, creating an array of new frames of size N*K, where K>>1. Two adjacent frames of original data are linearly averaged and de-noised, thus creating a new frame that is not a linear combination of the original two adjacent frames. A new level of frames is created and each new frame at that level is averaged and de-noised with a small threshold value. This is illustrated in FIG. 5.

The process of building an array of new frames is iterative. The new method first applies de-noising with a small threshold $\delta_k$ to each of the N original ABR data frames and then recombines the frames to obtain new single-frame sub-averages. De-noising is applied again with a different threshold $\delta_{k+1}$ to each one of the new frames. This process continues until a set of N*K wavelet de-noised frames is obtained. When the last level of frames K is obtained, the frames at this level are linearly averaged to generate a single de-noised frame. The operation of frame recombination preferably has K=$\log_2$ (N) levels, and at each level preferably a different wavelet coefficient threshold $\delta_k$ is applied as a function of the level k. The novel algorithm in its broadest sense has three main features, amongst others:

1. Each individual frame of the N original data frames is used to estimate the signal,
2. De-noising is performed in step-by-step fashion, and preferably using different threshold levels,
3. K*N new frames of data are preferably created from the original N frames.

Application of this algorithm increases the quality of the averaged signal such that a waveform can be reliably interpreted by a human expert after only a small number of ABR frames have been acquired. The novel algorithm may be compared to linear averaging. The performance may be tested against linear averaging using both simulated data and human subjects, to demonstrate that the novel algorithm produces a faster estimate of key features of the underlying low SNR signal.

While some of the advantages and features of the present invention have been explained above, a fuller understanding may be gained by referring to the drawings and detailed description of the preferred embodiment that follow.

BRIEF DESCRIPTION OF THE DRAWINGS

FIG. 19 is a graph showing a tree de-noising averaging algorithm for example N=8 frames wherein the original signal x[n] is dyadically averages and at three levels creating three new signals x1[n], x2[n], x3[n];

FIG. 20 is a graph showing a cyclic-shift tree denoising (CSTD) algorithm for example N=8 frames wherein the depth of the tree is $\log_2(8)$=3 and each level contains exactly N frames, consisting of a different combination of frames from the level immediately above it;

FIG. 35 is a series of graphs showing a comparison between linear averaging and CSTD for 32, 128, 256, and 512 frames;

FIG. 38 is a series of graphs showing $F_{sp}$ recordings for a patient's ears (Ear 3 through Ear 8) wherein Ear 3 and Ear 4 belong to the same patient and share no-stimulus recording and all other ears share no-stimulus recording;

FIG. 50 is a series of graphs showing Ear 9 CSTD (left) and variance comparison (right);

DETAILED DESCRIPTION OF THE PREFERRED EMBODIMENT

Figure 1:
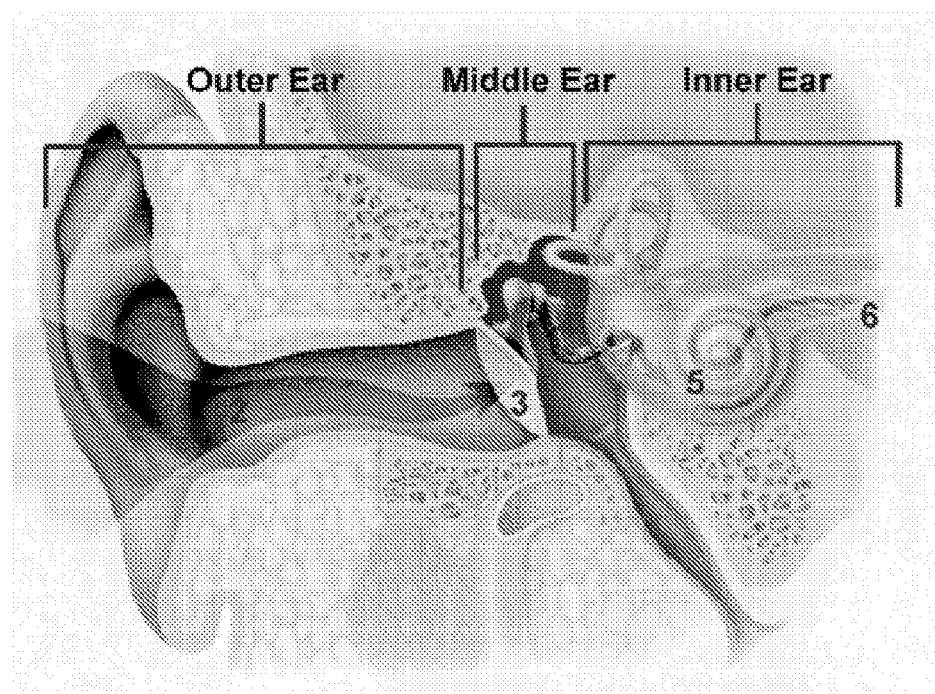
FIG. 1 is a partial cross sectional view of the Human peripheral auditory system.
Figure 2:
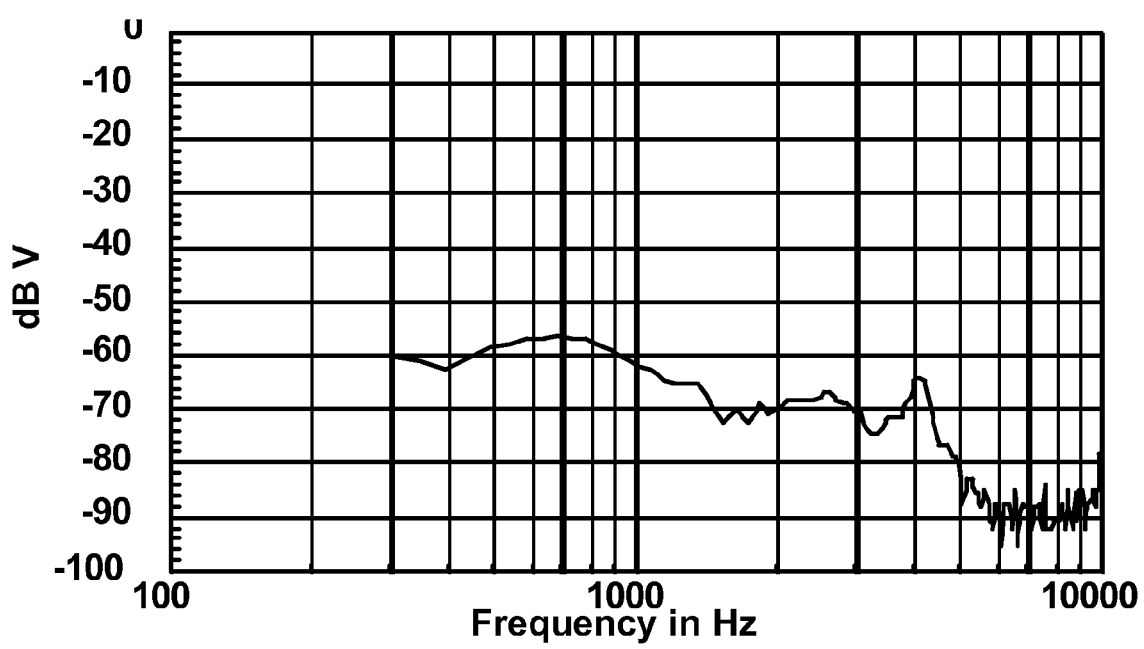
FIG. 2 is a graph showing frequent domain characteristics of a typical ABR click stimulus as measured in the ear using the ER-10C transducer.
Figure 3:
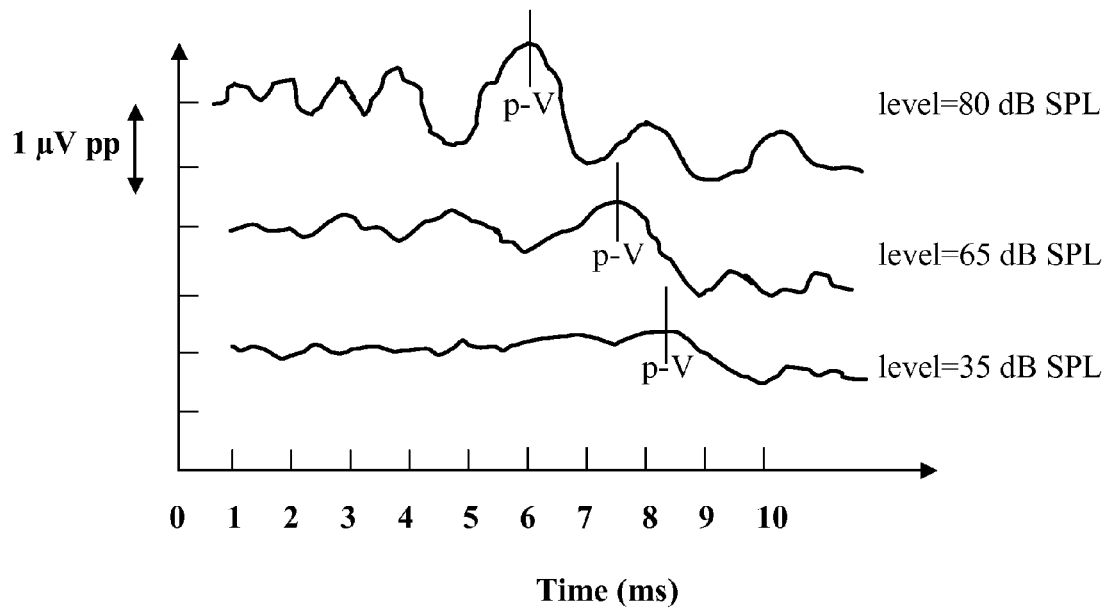
FIG. 3 is a graph showing typical ABR peak pattern for a normal hearing adult.
Figure 4:
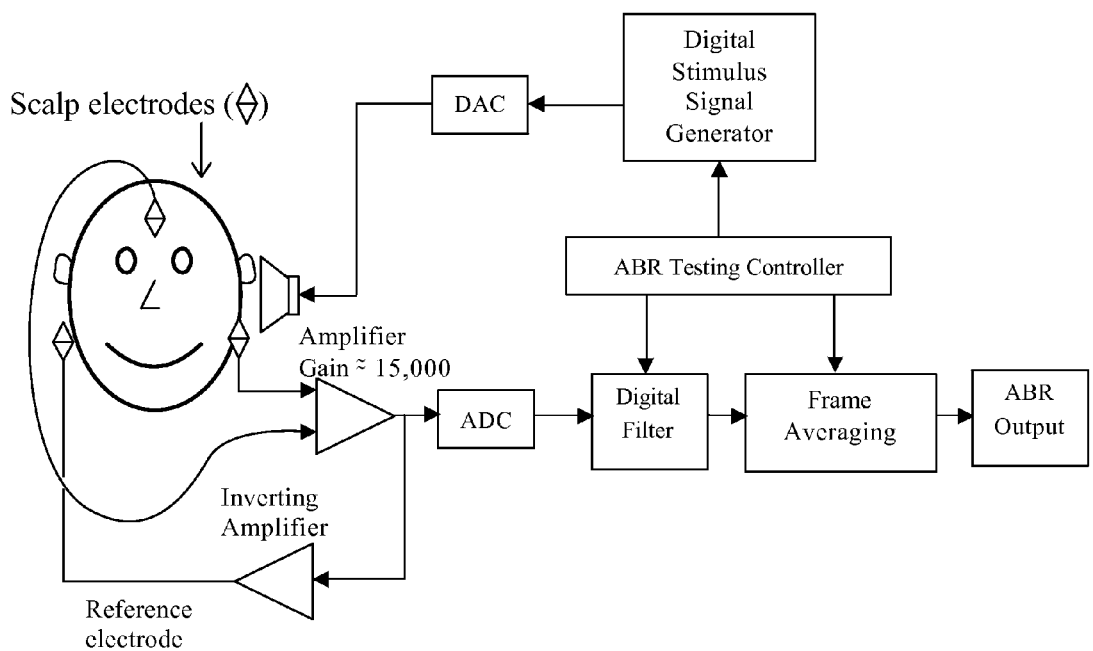
FIG. 4 is a schematic diagram showing a typical ABR signal acquisition ands processing system.
Figure 5:
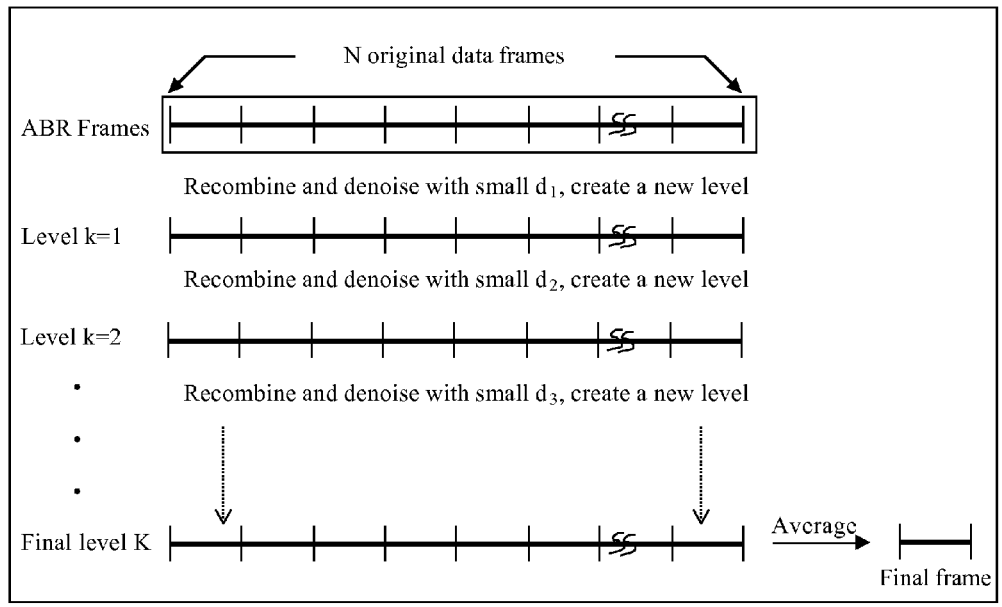
FIG. 5 is a graph showing a tree-denoising algorithm wherein original N frames of ABR data are combined and denoised and a set of new frames is created at the new level, the process being repeated to level K, creating a total noise of N*K new frames where the frames at level K are averaged together to create the final averaged frame.
Figure 6:
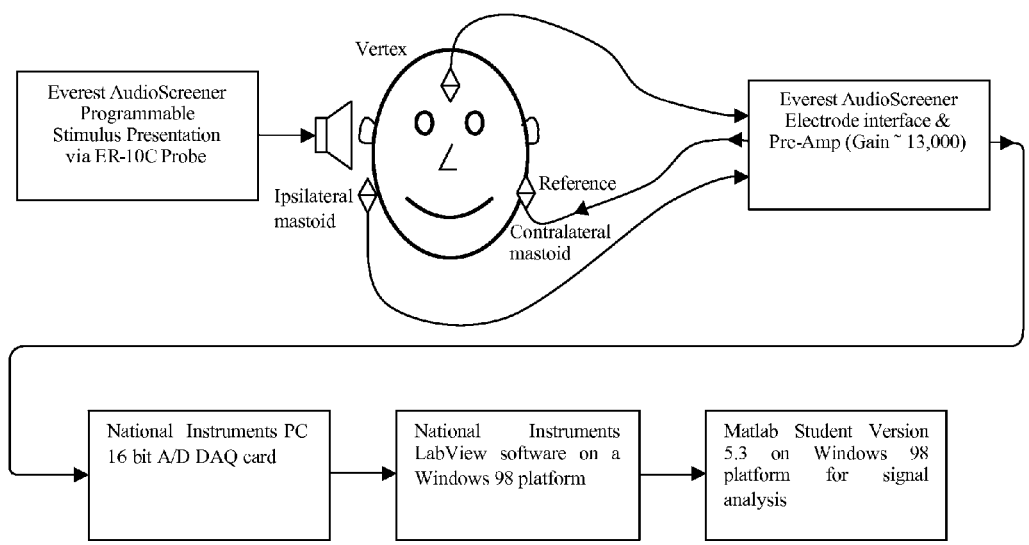
FIG. 6 is a schematic drawing showing a block diagram of a data acquisition and processing system.
Figure 7:
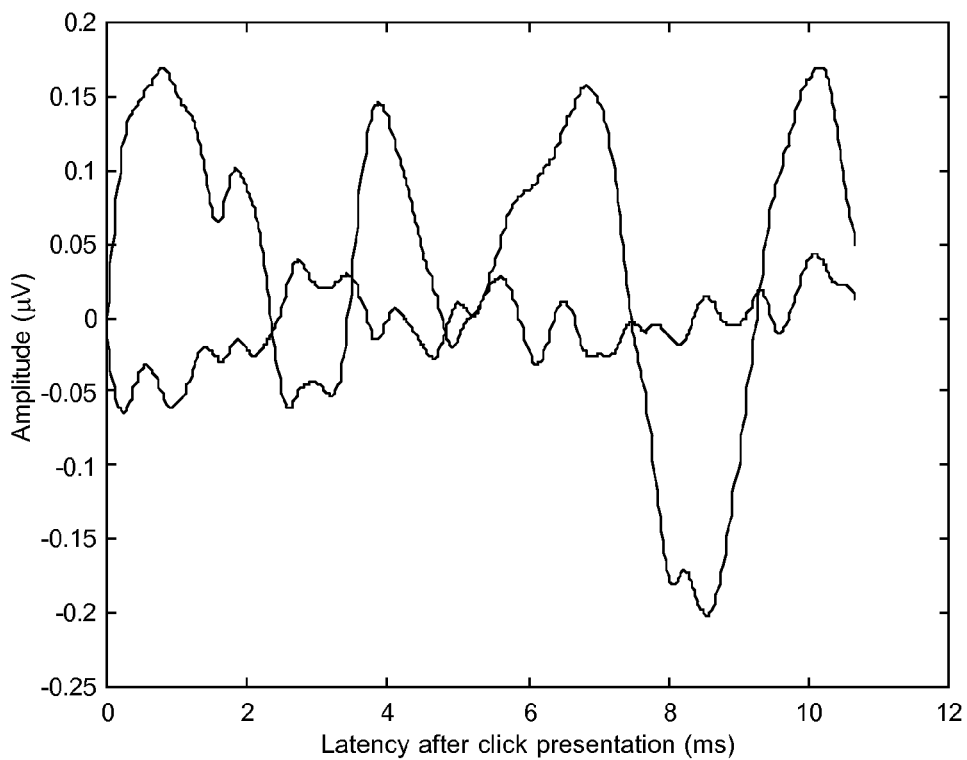
FIG. 7 is a graph showing a typical ABR waveform resulting from 65 dB SPL stimulus and averaged over 8,192 frames, overlaid by the system noise waveform wherein the noise was recorded using a Y-network of three 5.2 kΩ resistors attached to electrodes.
Figure 8:
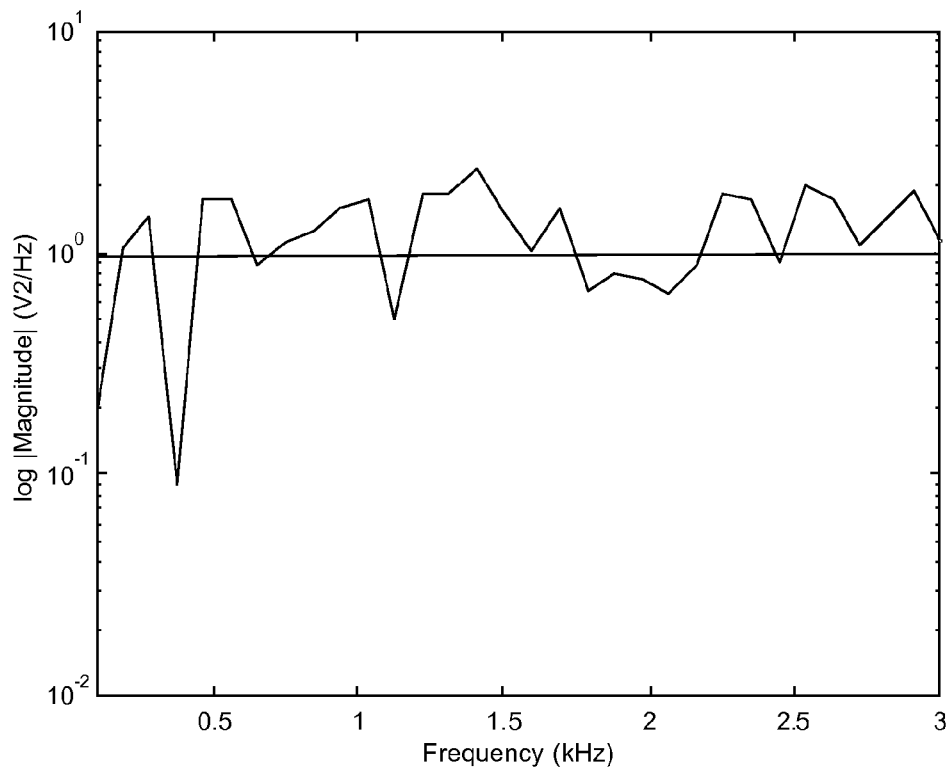
FIG. 8 is a graph showing a power spectral density of no-stimulus recording colleted from a subject's scalp without averaging.
Figure 9:
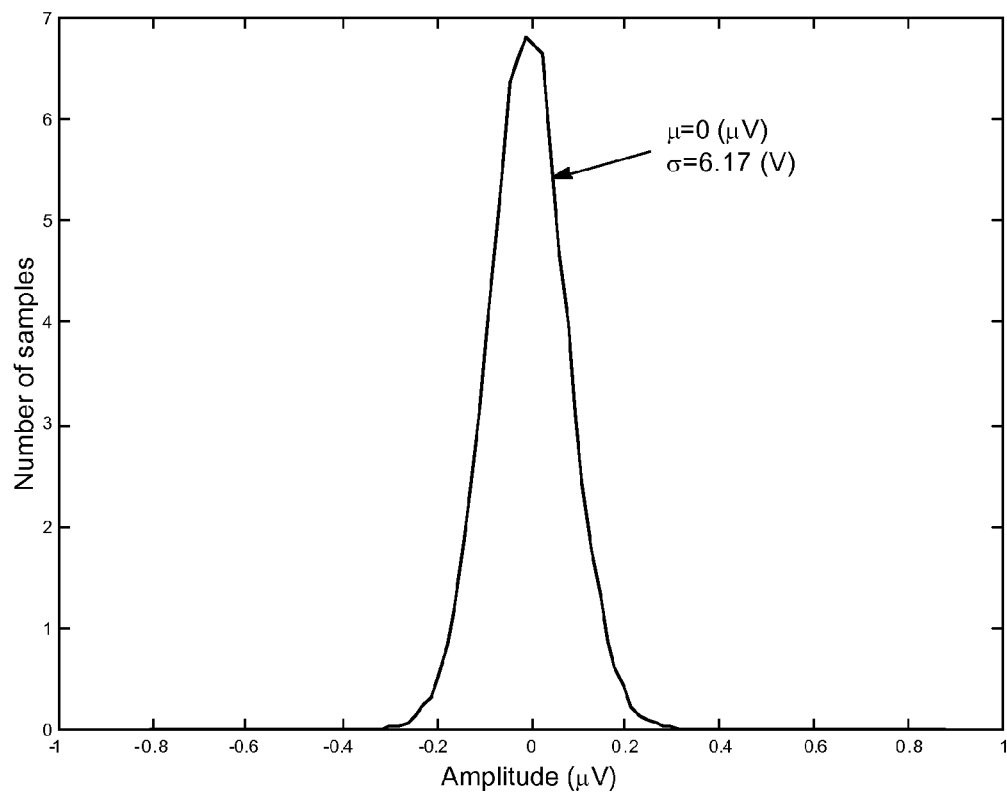
FIG. 9 is a histogram of no-stimulus ABR recording without averaging.
Figure 10:
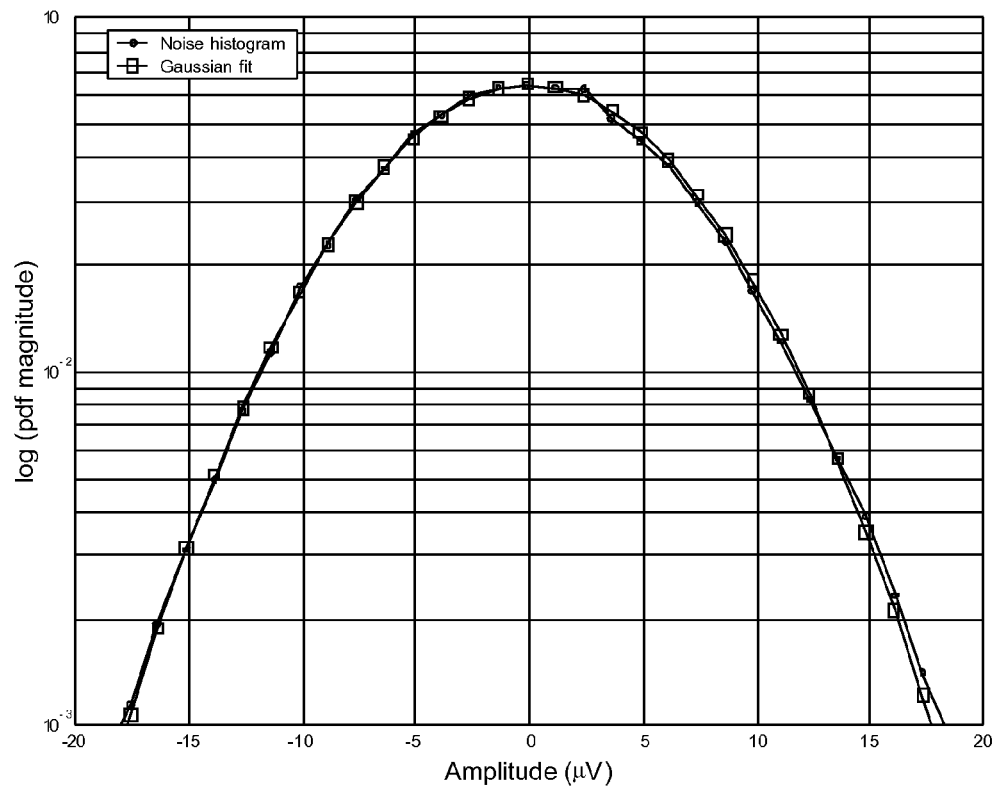
FIG. 10 is a graph showing a log-plot of noise-only recording fir to a Guassian probability density function with 6δ.
Figure 11:
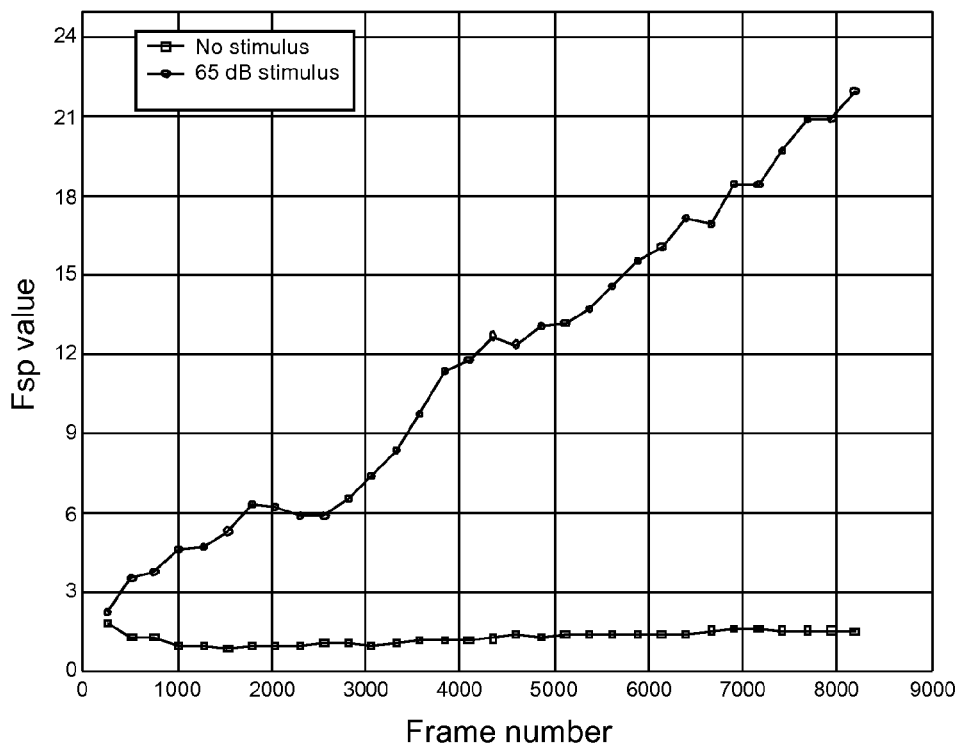
FIG. 11 is a graph showing a comparison of $F_{sp}$ values with and without stimulus presentation.
Figure 12:
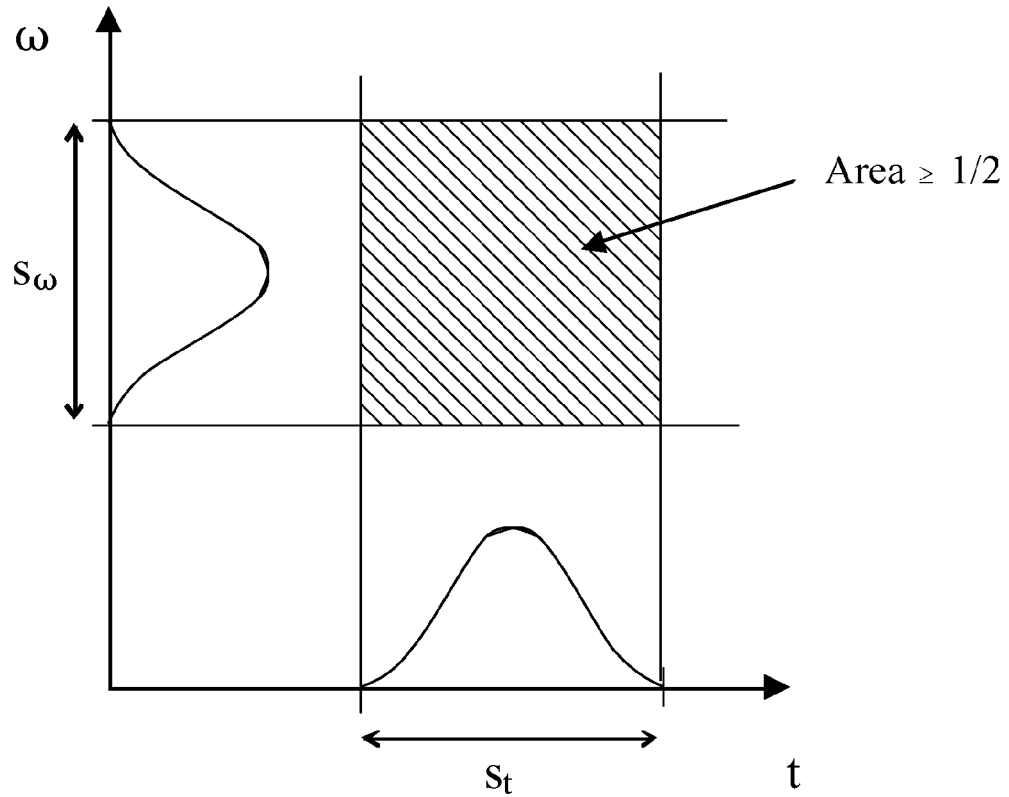
FIG. 12 is a time frequency-box representing energy concentrations in time and frequency domains for a wavelet function.
Figure 13:
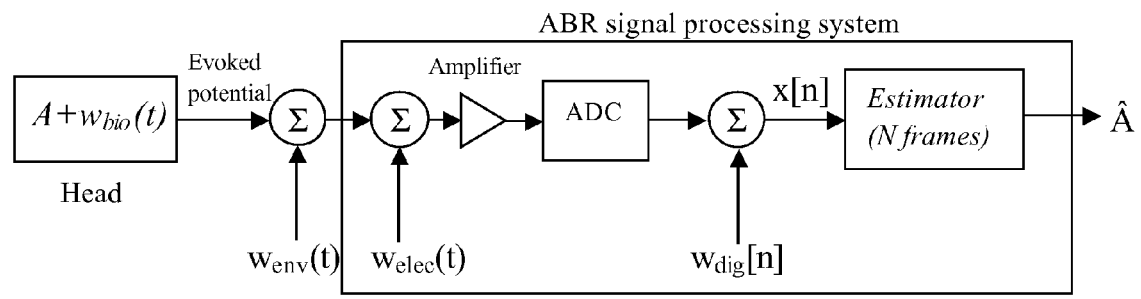
FIG. 13 is a ABR signal block diagram.
Figure 14:
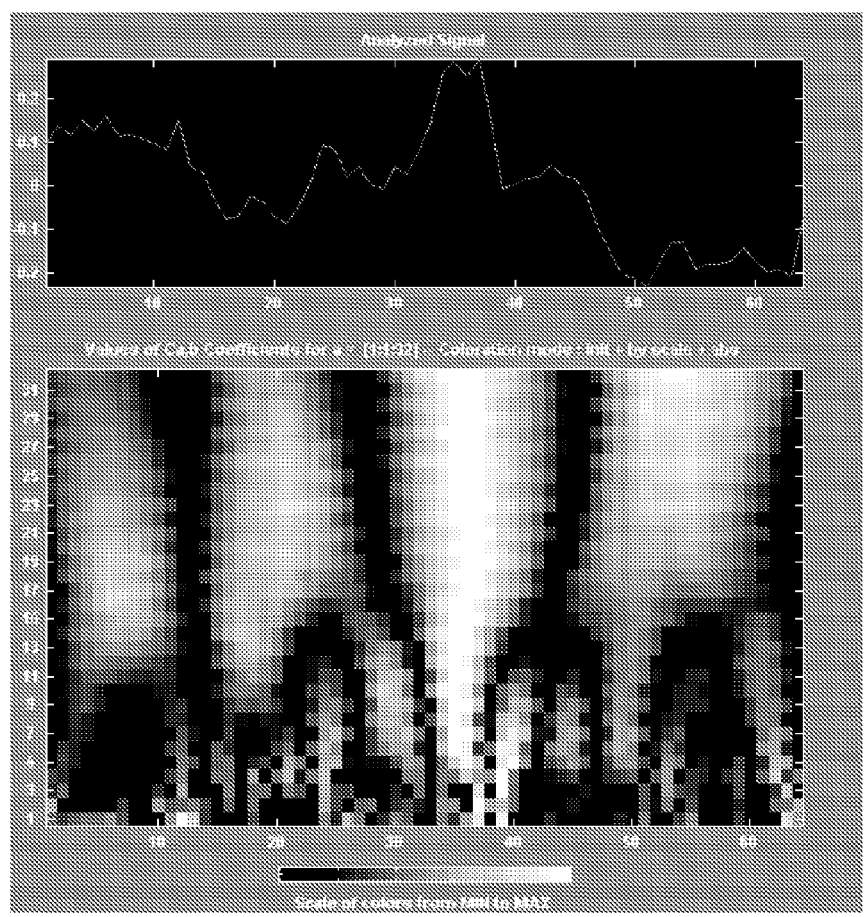
FIG. 14 is graph showing decomposituion of a typical averaged ABR signal using a wavelet transform at 32 levels with a biorthogonal 9-7 wavelet.

A typical commercial ABR system as found in the prior art to collect data presents clicks into the ear canal and records data from the scalp electrodes. The data is filtered and then averaged together in frames of approximately 15 ms following the stimulus presentation. Existing commercial ABR systems do not have a capability of recording long sessions of raw data—unfiltered and unaveraged. To investigate the performance of the novel algorithm, several thousand frames of unprocessed data (i.e., N=8,192) were needed to be recorded for later analysis. The objective was that exactly the same data was analyzed for different processing schemes and parameters. A custom-built system was used for data acquisition and storage. This system was built by Everest Biomedical Instruments Company (Everest), a designer and manufacturer of commercial OAE and ABR test equipment. The system was built from a combination of clinical ABR components and high quality laboratory data acquisition equipment. The basic system consists of an ear probe to present the acoustical signal in the ear, electrodes connected to a pre-amplifier, data acquisition interface, and a signal processing system. The block diagram of the system is shown in FIG. 2-1 below.

The acoustic stimuli were presented to the ear with the Etymotic Research ER-10C probe, which has two independent speakers (receivers), and two inter-connected microphones. The probe was inserted into the ear canal using a foam ear tip, also manufactured by Etymotic Research. Only one of the speakers was used to present the stimuli. The microphones were used to ensure probe fit during the test by checking "acoustic leakage" of a low frequency test signal, and for in-the-ear calibration of the stimulus level. Three electrodes were attached to each subject's head, one each on the left and right mastoid process (M1 and M2), the bone behind the ear, and one applied to the vertex ($C_z$), in the middle of the top of the forehead. The electrodes were located per standard EEG and ABR configuration—vertex ($C_z$) and mastoid (M1 and M2). The electric potentials were recorded differentially between the vertex and the ipsilateral mastoid process (behind the ear containing the probe). The contralateral mastoid electrode (behind the other ear) was used as a reference. Inverted common mode voltage between the vertex and the ipsilateral electrode was fed into the reference electrode to reduce 60 Hz power line interference.

The front-end electronics interface to which the electrodes were attached was the Everest Biomedical Instruments' AudioScreener™, as presently commercially available. This product has been tested for safety and certified by Underwriters Laboratories (UL) to meet the UL 2601 Electrical Safety standard for medical devices. The product is also U.S. Food and Drug Administration (FDA) approved for clinical use for hearing screening via the 510(k) process. However, because it is a handheld product primarily used for hearing screening, it, like the other devices available in the prior art, does not have the capability to record long streams of data.

Therefore, only the front end of the AudioScreener™ was used as an audio stimuli generator and a high-quality EEG pre-amplifier.

The auditory click stimuli were generated using the AudioScreener™ audio output section. The peaks were calibrated using a standard procedure and IEC standard, as known in the art. An external signal generator generating a pure sine wave at 1 kHz was fed into a speaker portion of the insert ear probe. The output was measured in peak dB SPL with a precision calibrated sound level meter (Quest Model 1800) with a Quest standard 0.5 cc coupler ($0.5 \times 10^{-6} m^3$). The electrical output of the signal generator was also measured using a two channel digital oscilloscope (Hewlett Packard 54645D). The AudioScreener™ then generated a 100 μs rectangular pulse, which was measured on the second channel of the oscilloscope. The peak magnitudes of the sine wave and the click were aligned, and a peak SPL level was established. This reference level was used for in-the-ear calibration during testing. The stimulus repetition rate was set to 37 per second, or one 100 μs click every 27.03 ms. This rate was selected to match the normative data given by well known literature in the art. Stimulus repetition rates of 21, 33, 37, 38, etc., are commonly used because they are relatively prime to both 50 Hz and 60 Hz power line frequencies. Hence, when frames acquired at the frequency of 37 per second were linearly averaged, the effect of 60 Hz interference was reduced, because the power line interference is out of phase with the acquired frames. The ABR signal contained in the frames added constructively with each new acquired frame, while the 60 Hz power line interference added destructively.

The electrodes were attached to a front-end amplifier of the AudioScreener™. The signal was amplified differentially by a factor of 13,000, and presented to the next stage. The differentially amplified signal was inverted and fed into the reference electrode attached to the ipsilateral mastoid, to reduce any common mode interference such as 60 Hz power line interference. Also, the differentially amplified signal was filtered with a built-in second order analog highpass filter (HPF) filter with −3 dB point at 30 Hz, and a third order lowpass filter (LPF) with a −3 dB point at 3 kHz. The input impedance of the Everest preamplifier was 10 MΩ, and common mode rejection ratio (CMRR) of the input amplifiers was 110 dB. The leakage current was certified by UL to be below 100 μA AC and below 100 μA DC.

The output of the AudioScreener™ pre-amplifier section was fed to a commercially available National Instruments data acquisition (DAQ) board with a successive approximation Crystal Semiconductors A/D converter (NI DAQ PCI-MIO-16XE-10). Data was sampled at 16 bit resolution. The input range of the ADC was ±10V. Thus, the minimum detectable voltage by the ADC was 0.305 mV at the ADC input. This means that the signal resolution as measured by the scalp electrodes is 23 nV. See, National Instruments Corporation, *PCI-MIO E Series User Manual*, Austin, Tex. (1997).

The sampling frequency of the existing hardware and software data acquisition system was fixed at $f_s$=48,000 Hz, with an anti-aliasing filter set at 24 kHz. It is important to note that the signal of interest had a bandwidth of 3 kHz. If a system had been built specifically for this work, the anti-aliasing filter would have also been set at 3 kHz and the sampling frequency selected at just above 6 kHz. However, this was an existing, custom-built system used internally by Everest on a regular basis for various other signal processing investigations. Thus, other arrangements as would be known to routineers in the art given the inventors teaching herein would work as well. Additionally, software associated with the data acquisition hardware was built and tested thoroughly to process signals sampled at 48 kHz, and was not easily re-programmable for other sampling frequencies. Such sampling software may be readily duplicated by any one of skill in the art without undue experimentation, and such software used to acquire the data is not considered as related specifically to the present invention which instead focuses on de-noising the data after acquisition. Finally, the existing system collected 1,024 samples per frame, corresponding to approximately 21.3 ms of a recording following a stimulus. This was done to investigate the ABRs for low level stimuli, whose latency can extend to approximately 20 ms. Only about 10 ms of a response following a stimulus was required for this work, and that could have been sampled at the rate of 6 kHz. This means that a single frame should consist of 64 samples. This was accomplished by post processing the data, as described below, although as previously noted the present invention is intended to be directed at de-noising the data regardless of how it is collected and pre-processed.

A National Instruments data acquisition software package called LabVIEW was used to take the data from the DAQ card and store it in a standard file format on the hard disk on the host PC computer. A total of 8,192 frames of data were collected for each testing condition. Each frame contained 1,024 samples or 21.3 ms of data synchronized with the click presentation. While LabVIEW is an advanced system for data acquisition and processing, it does not lend itself well for complex computations and large data array manipulations. Furthermore, it has limited built-in wavelet capabilities. The LabVIEW package simply collected the data from the pre-amplifiers and saved on them on disk. No signal processing took place in LabVIEW, filtering or otherwise.

Once the data were available in a standard file format, an advanced software package called Matlab was employed for analysis. Matlab (by MathWorks) Version 5.3.1 was used for all of the signal processing. In addition to Matlab's standard tools, Matlab Signal Processing, Wavelet, and Statistics toolboxes were utilized.

All signal processing operations were conducted in Matlab. The first one was to reduce the oversized data set collected by the existing LabVIEW system. The second was to calculate wavelet transforms for each of the frames and obtain wavelet coefficients. Then, in accordance with the teaching of the present invention and as explained in greater detail below, these frames of wavelet coefficients were recombined and thresholded, and an inverse wavelet transform was calculated for the final frame of wavelet coefficients. Finally, all of the data were plotted using the Matlab graphing features.

The reduction of the LabVIEW data set was accomplished in two steps. First, 512 samples were extracted from the 1,024 sample frame corresponding to 10.67 ms of a response following stimulus presentation. Next, the frame size needed to be reduced from 512 to 64 samples. Sampling a 3 kHz signal at the sampling rate of 48 kHz introduced unnecessary noise energy beyond the signal of interest. The signal was oversampled by a factor of 8. However, standard signal processing techniques can adequately correct this condition by filtering and resampling. A typical signal processing method to accomplish this is to first lowpass filter the data at one eight of the original sample rate, or 6 kHz, using a finite response filter (FIR), and then decimate the resulting samples by a factor of 8 to create 64 samples per frame. However, a slightly different method with an equivalent result was used. Because wavelet processing was being performed on all data frames anyway for the purpose of implementing the present invention, the lowpass filtering and resampling was performed in the wavelet domain. The wavelet transform was originally performed on each 512 point data frame, resulting in $\log_2(512)=9$ decomposition levels. The first three levels of wavelet decomposition produced high frequency wavelet coefficients. All the coefficients at these levels were set to zero. The rest of the wavelet coefficients were kept: a total of 64. This process is analogous to lowpass filtering and resampling using standard signal processing techniques. No resampling was required, because the wavelet transform already produced the 64 samples at the next decomposition level. As will be discussed below, the wavelet transform is performed using successive applications of FIR filters, so the computational cost of filtering by using a wavelet transform was similar to that using a standard signal processing method.

The similarity of the two methods was tested on a subject recording of 8,192 frames. The data was LP filtered at 6 kHz using a Butterworth linear phase Matlab filter. The frames were then decimated by a factor of 8, producing 64 samples per frame. Then a 64-point wavelet transform was performed at 6 decomposition levels, producing 64 wavelet coefficients per frame. The entire algorithm with frame recombination and wavelet thresholding was applied, and an inverse wavelet transform was performed yielding 64 time domain samples of the processed ABR data. In parallel, the same data was processed without LP filtering by a 512-point wavelet transform. The first three levels of coefficients (of lengths 256, 128, and 64, respectively) were set to zero. This was analogous to LP filtering. The remaining 64 coefficients per frame were processed using the same algorithm as in the above case. The inverse wavelet transform again yielded 64 time domain samples of the processed ABR data, produced essentially the same data, and had almost identical performance when compared to linear averaging. The data was not completely identical because the FIR filter characteristics of the Butterworth filter and the wavelet filter were slightly different. Hence, all novel signal processing in this work was performed on the 64-sample frames, and the only negative effect of initial oversampling were increased file sizes and computational penalties.

Because of the large amount of noise present in the ABR recording process, it was necessary to assure that the recorded data indeed had a signal component. Many factors such as electrode misplacement or an acoustical probe falling out of the ear canal during the recording can cause the data to be inaccurate. Therefore it was necessary to check the recording process to make sure that a valid ABR signal was present.

The validity of the recording was obtained by examining the variance of the signal. It is expected that if only noise is recorded with no stimulus present that the absolute energy of the averaged recording will tend to zero. If there is a stimulus present, this long term average energy will be larger than zero.

The performance of the ABR data acquisition system was thoroughly tested using both the electronics testing methods as well as standard tests published in commonly cited audiology research literature. The system was tested with shorted inputs, with known inputs generated by an arbitrary signal generator, with EEG data with no stimulus present, and finally with EEG data with auditory stimuli present. The system performed as expected and as reported in the literature.

There are many types of wavelets used for wavelet transforms, and many types of transforms available. Because of the nature of digital acquisition of ABR signals the present invention will focus on the discrete wavelet transform (DWT) using a particular type of symmetrical wavelets called biorthogonal wavelets, as known in the art. The wavelet transform gives a two dimensional array of coefficients. De-noising reduces the magnitude of the wavelet coefficients, which preserves the local smoothness of the signal.

Figure 16:
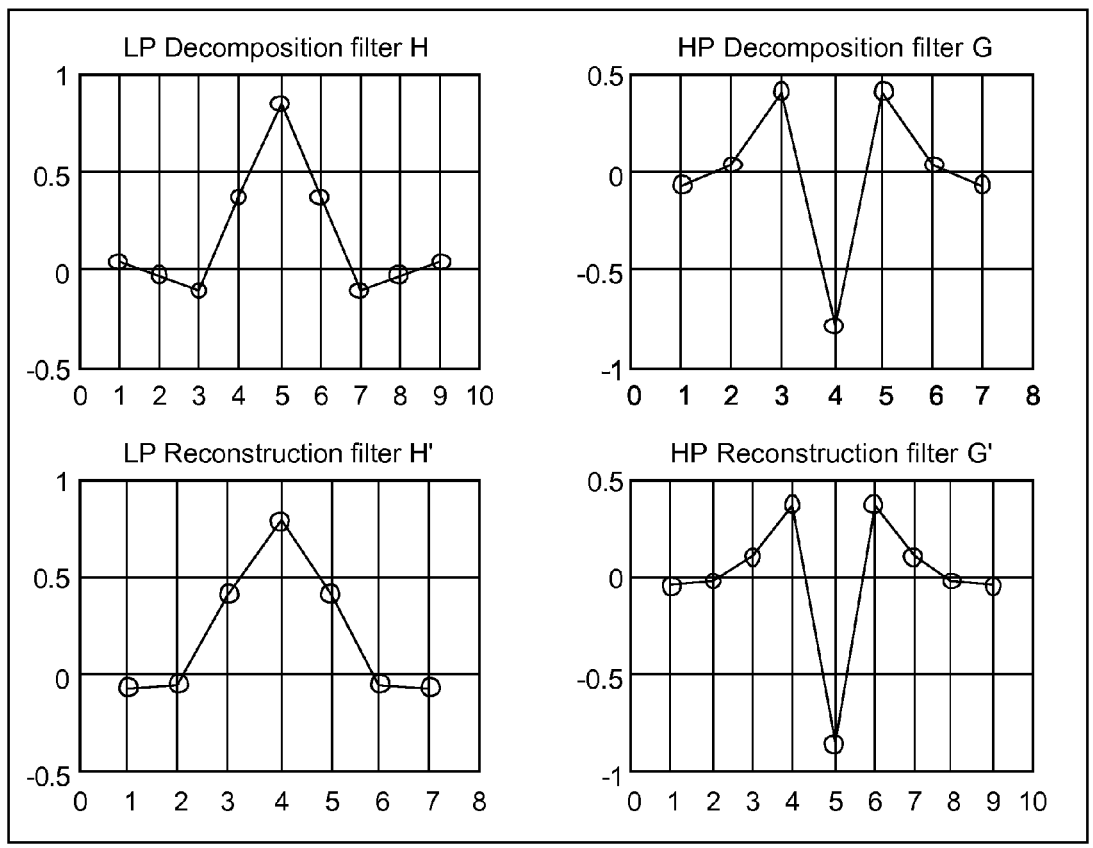
FIG. 16 is a series of graphs showing LP filter H and HP filter G for decomposition and LP filter H' and HP filter G' for reconstruction for biorthogonal 9-7 wavelet transform wherein Matlab indexing convention was used with filters H and G indexed [1,9] and [1,7] respectively, instead of H and G indexed by [4,4] and [−4,2], respectively.
Figure 17:
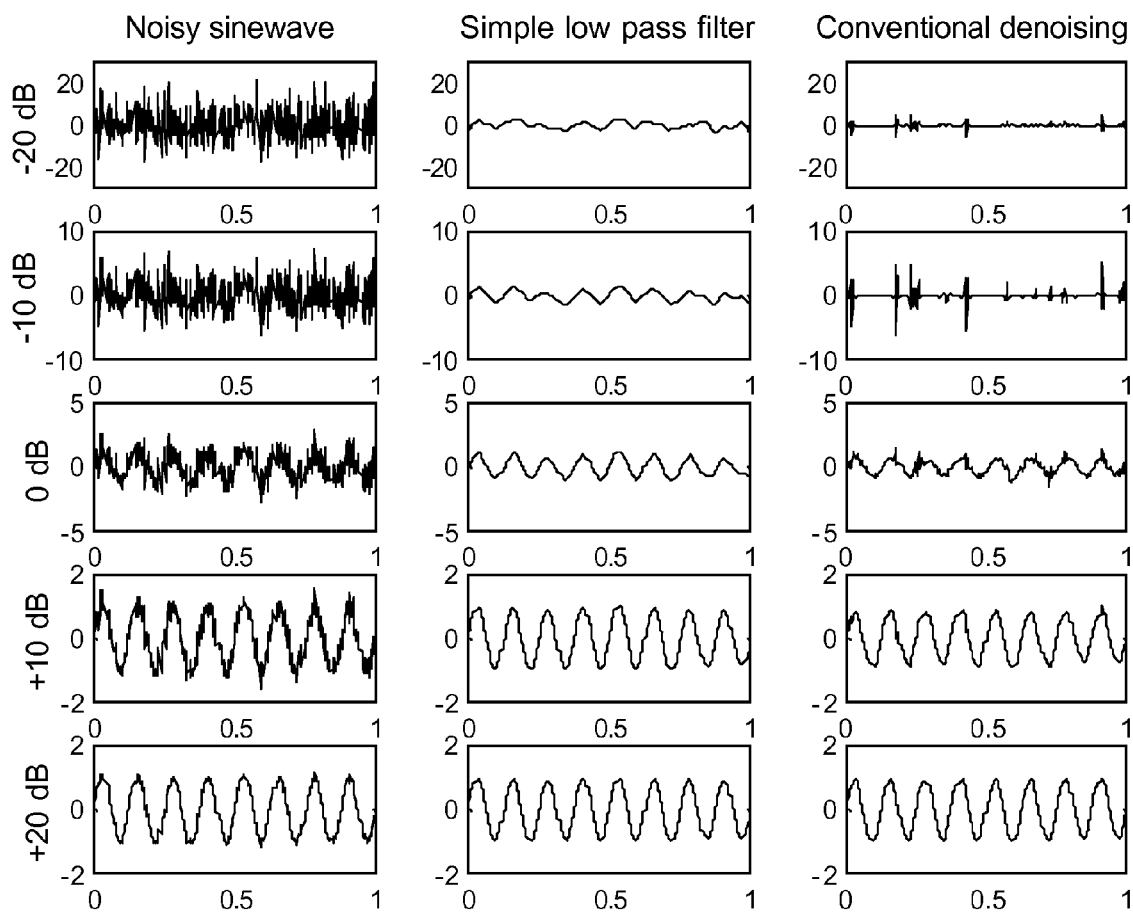
FIG. 17 is a series of graphs showing the results of low pass filtering compared to conventional denoising applied to noisy sinewaves with SNRs from −20 dB to +20 dB.
Figure 18:
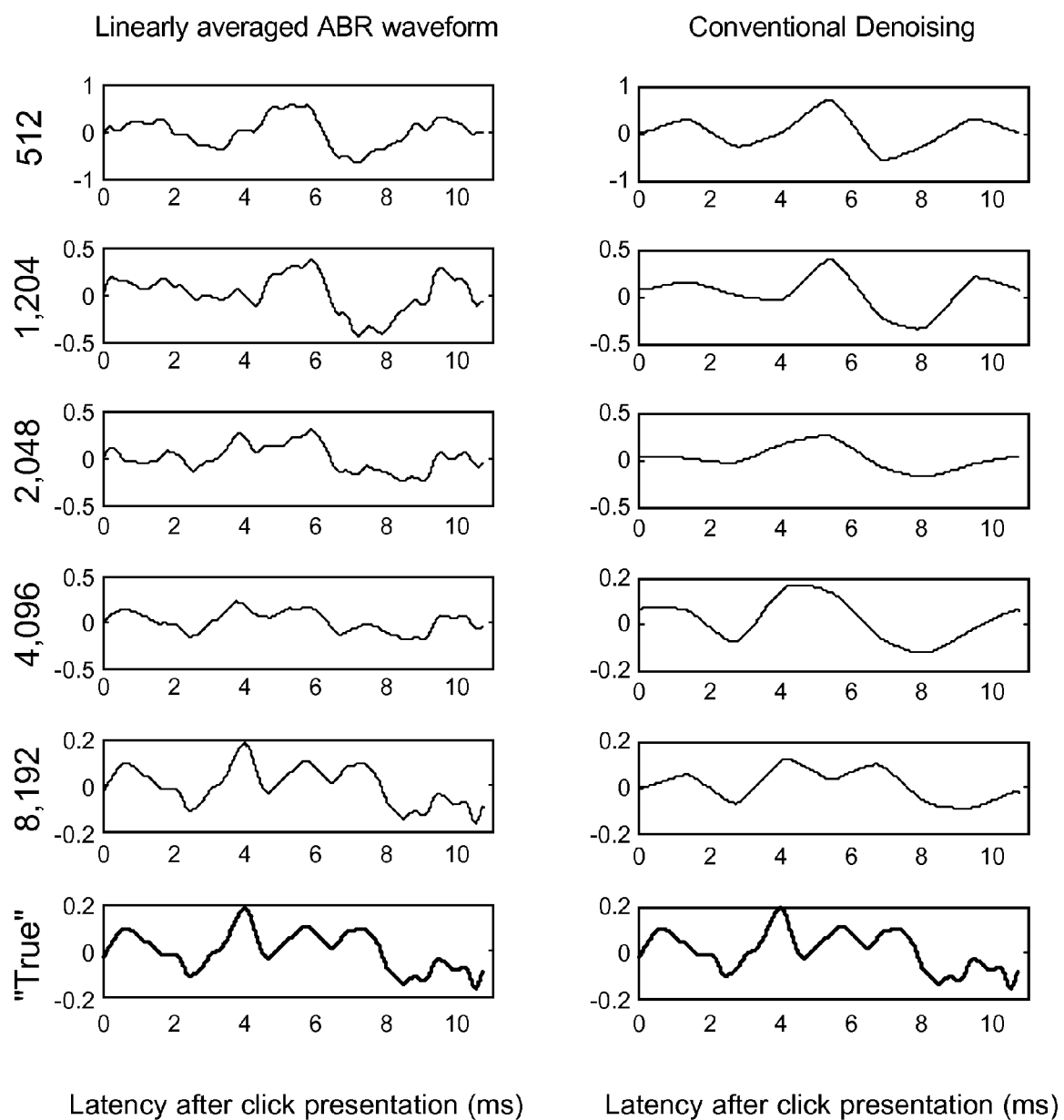
FIG. 18 is a series of graphs showing conventional denoising applied to a typical ABR signal wherein the left column shows a progression of linear averaging of 512 through 8,192 frames and the right column shows the corresponding conventionally denoised linear averaging.

A simplistic view of the wavelet transform is that the transform utilizes a mother wavelet function and creates a family of wavelet functions that are different dilations and translations of the mother wavelet. Each of these new wavelet functions is convolved with the original signal, and a two dimensional space of coefficients is produced, at different scales and translations. FIG. 16 shows a graph of a wavelet transform of a typical averaged and filtered ABR signal, at 32 scales (vertical dimension) and 64 translations at each scale (horizontal dimension). The biorthogonal wavelet was used for the wavelet transform.

Figure 15:
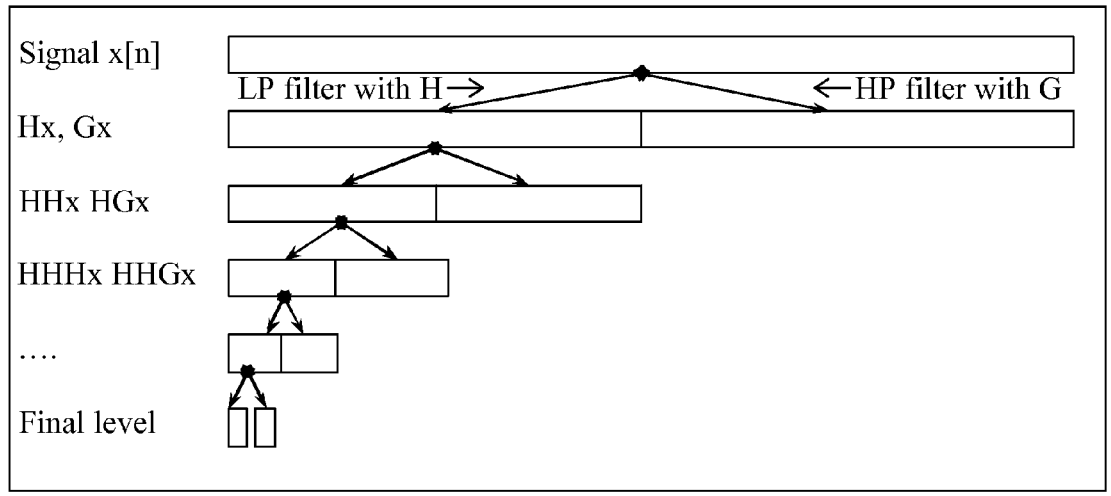
FIG. 15 is a graph showing DWT by using a set of LP and HP filters and decimation applied to signal x.

The DWT as implemented in this invention can be viewed as processing the original signal using a bank of "constant-Q" filters applied successively. The application of filters decomposes a signal in high-pass (HP) and low-pass (LP) components, decimates by a factor of 2, and then further decomposes to another set of highpass and lowpass components, and so on, until the signal is fully decomposed. At each of the decomposition levels, the coefficients can be either set to zero or reduced in magnitude, such that a particular feature of the signal is affected upon reconstruction. If the LP and HP filters (H and G respectively) used for decomposition are quadrature mirror filters (QMFs), and if their biorthogonal complements are used for reconstruction with proper treatment of endpoints, then a perfect reconstruction in phase and amplitude can be achieved. FIG. 15 below shows graphically how the wavelet decomposition is done using successive applications of LP and HP filters.

The DWT used to describe the wavelet coefficients for using the Biorthogonal 9-7 wavelet is as follows:

$$H\{x\} = \sum_{k=-4}^{4} h[k]X[2n-k],$$

$$G\{x\} = \sum_{k=-4}^{2} g[k]X[2n-k].$$

Functions h[k] and g[k] are biorthogonal decomposition filters for the 9-7 wavelet. The name 9-7 comes from 9 taps for the h[k] filter [−4,4], and 7 taps for the g[k] filter [−4,2]. An alternate way that biorthogonal 9-7 wavelet is defined is by the number of vanishing moments, which is 4 each for both the h[k] and the g[k] filter. The biorthogonal 9-7 wavelet has 4 vanishing moments (its name in Matlab is bior4.4). The coefficients used for the filters using this wavelet are given in Table 2 below which shows FIR filter coefficients for the Biorthogonal 9-7 wavelet

| K | h[k] = (−1)$^k$ g'[k] | k | g[k] = −(−1)$^k$h'[k] |
|---|---|---|---|
| −4.4 | 0.03782845550699 | −4.2 | −0.064538882628938 |
| −3.3 | −0.02384946501938 | −3.1 | 0.040689417609558 |
| −2.2 | −0.11062440441842 | −2.0 | 0.418092273222212 |
| −1.1 | 0.37740285561265 | −1 | −0.788485616405664 |
| 0 | 0.85269867900940 | | |

A biorthogonal class of wavelets was chosen because their DWT implementation can be accomplished using simple and short FIR filters, and still allow perfect reconstruction.

The biorthogonal 9-7 wavelet was chosen because it is symmetric and because it has 4 vanishing moments. This makes it suitable for distinguishing between the expected regularity of the smooth ABR signal vs. the zero regularity for the rough AWGN noise. The H, H', G, and G' filters implementing the biorthogonal 9-7 wavelet are shown in FIG. 16.

The biorthogonal 9-7 wavelet is also the wavelet used for EEG wavelet signal processing in research literature, the JPEG 2000 image compression standard, and is also used by the FBI for the national fingerprint storage database.

Relevant characteristics of the existing conventional de-noising algorithm are as follows:
1. Wavelet coefficients thresholded to zero at each wavelet decomposition level
2. SNR of the original signal must be large prior to applying de-noising (>+10 dB)
3. All de-noising operations are performed on a single data vector The first characteristic is in common with the present invention. The second characteristic is a limitation that is overcome by the present invention, whose performance is demonstrated for signals with SNR less than zero. The third characteristic of conventional wavelet de-noising is expanded here from a single data vector to all the available data, or in the case of ABR, from de-noising a single, final linearly averaged frame, to step-by-step de-noising of all of the available frames and their recombinations in a tree like fashion.

One aspect of the present invention is that it reduces the variance of the ABR signal estimator as a function of the number of frames, beyond that of the optimum linear estimator. The inventor makes use of the fact that wavelet de-noising is a nonlinear process, and that he has each of the individual N frames available. Ways are found to recombine the original N frames, and de-noise those recombinations, thus creating additional frames that are not a linear combination of the original frames. The method of the present invention then performs step-by-step de-noising, by combining original frames and de-noising them, and then repeating the procedure until all original and new frames are recombined in as many ways as possible. A wide variety of different algorithms are possible to implement this task.

Preferably, the frames are combined by using two adjacent frames and calculating their linear average. This method is chosen for its simplicity, computational stability, and well-understood behavior. This dyadic linear average is then de-noised, and a new frame is created. The overall idea is to generate as many permutations of the original arrangement of frames as possible, and keep averaging and de-noising those new combinations of frames. This recombination process is a tree-like process, in which new levels of recombined frames are created. The average and de-noise operation creates frames at level k, which are no longer a linear combination of frames from level k−1.

The many possible algorithms to accomplish this task can be evaluated by different criteria: ease of implementation, computational efficiency, computational stability, etc. For the present invention, ease of implementation is used, because the key aspect of the invention is implementation of different wavelet de-noising techniques and not combinatorics of frame rearrangements. The goal of the preferred embodiment in frame rearranging is to produce enough new frames to obtain acceptable performance.

Several algorithms are suitable for generating large arrays of recombinations of frames. One such algorithm produces an array of new frames by dyadically averaging and de-noising. The new frames in this array are a function of the ordering of frames in the original ABR signal, i.e., $\{1, 2, \ldots, N\}$. Another algorithm involves a reordering of the original ABR frames by permutations i.e., $\{7, 19, \ldots, N, \ldots, N\text{-}93\}$, or $\{73, 4, \ldots N, \ldots, N\text{-}121\}$. This reordering process does not involve any averaging or de-noising, simply a rearrangement of frame indices. When a new reordering is obtained, the dyadic average and de-noising algorithm is applied to create a new array of frames. This way many arrays of frames are created, generating an overall large number of frames M>>N.

Given that a chosen method of frame recombination is dyadic averaging and de-noising, simple algorithms are disclosed to accomplish this. For all of the algorithms, wavelet coefficient thresholding is accomplished using the thresholding function by setting to zero all wavelet coefficients less than $\delta_k$. This thresholding process is denoted below by a function den(frame data,$\delta_k$).

A simple way to accomplish creation of new frames is by a tree de-noising algorithm as follows:
1. Collect a set of N frames of original data $[f_1, f_2, \ldots, f_N]$
2. Take the first two frames of the signal, $f_1$ and $f_2$, and average together, $f_{12}=(f_1+f_2)/2$
3. De-noise this average $f_{12}$ using a threshold $\delta_1$, $fd_{12}=$den$(f_{12},\delta_1)$
4. Linearly average together two more frames of the signal, $f_{34}$, and de-noise that average, $fd_{34}=$den$(f_{34},\delta_1)$ Continue this process for all N frames
5. Create a new level of frames consisting of $[fd_{12}, fd_{34}, \ldots, fd_{N-1,N}]$
6. Linearly average each two adjacent new frames to create $f_{1234}=(fd_{12}+fd_{34})$, and de-noise that average to create $fd_{1234}=$den$(f_{1234},\delta_2)$
7. Continue to apply in a tree like fashion
8. Apply a different $\delta_k$ for de-noising frames at each new level k.

This tree de-noising algorithm is depicted in FIG. 19. The total number of levels is K=log$_2$(N). The number of frames at each new level k is decreased by a factor of 2, because the average and de-noise operation of two adjacent frames at level k−1 create a single frame at level k. Then at the root of the tree, the level k=K, there is only one frame remaining. The total number of new frames created is N−1. A simple modification of this algorithm provides a larger number of frames, and will be presented next.

The simple tree de-noising algorithm can be expanded to maintain the same number of frames at each new level in the tree. We extend the new level k to include not only dyadic averages of adjacent frames at level k−1, but also dyadic averages of a cyclical shift by one frame at level k−1. This method is called here cyclic-shift tree de-noising (CSTD). The CSTD algorithm creates a tree (or array) of frames of width N and depth log$_2$N. At each level k, $1 \leq k \leq \log_2 N$, along the depth of the tree, two adjacent frames (dyads) are averaged and de-noised, and a new level is created. As before, since the de-noising operation applied to the dyadic average is a non-linear operation, the new frame is no longer a linear combination of the original two frames.

The algorithm takes N frames, and at first level of averaging produces N/2 averages of frames numbered 1,2; 3,4; 5,6; . . . ; N−1,N. Then another set of N/2 averages is produced at the first level from original N frames by averaging original frames 2,3; 4,5; 6,7; . . . ; (N−2),(N−1); N,1. These two sets of N/2 frames are concatenated, and a new level of frames is produced again of length N. At the next level, the algorithm is repeated, and four sets of cyclic shift averages are produced, each of length N/4. The process is repeated for $k_{max}=$log 2(N) levels (for integer k this requires that N is a power of 2 or $N=2^k$). This is depicted in FIG. 20 for 8 frames, denoting by $fd_{12}$ the operation $fd_{12}=den(f_{12},\delta_1)$:

This is the algorithm used in preferred embodiment because it provides K times more frames than the simple tree de-noising algorithm, and because of its simplicity of implementation and low computational complexity. A total of $M=N*\log_2(N)$ new frames is created. For the algorithm to have an equal number of frames at each level, it is necessary that the original number of frames be a power of two, i.e., $N=2^K$, where K is the depth of the tree.

Figure 53:
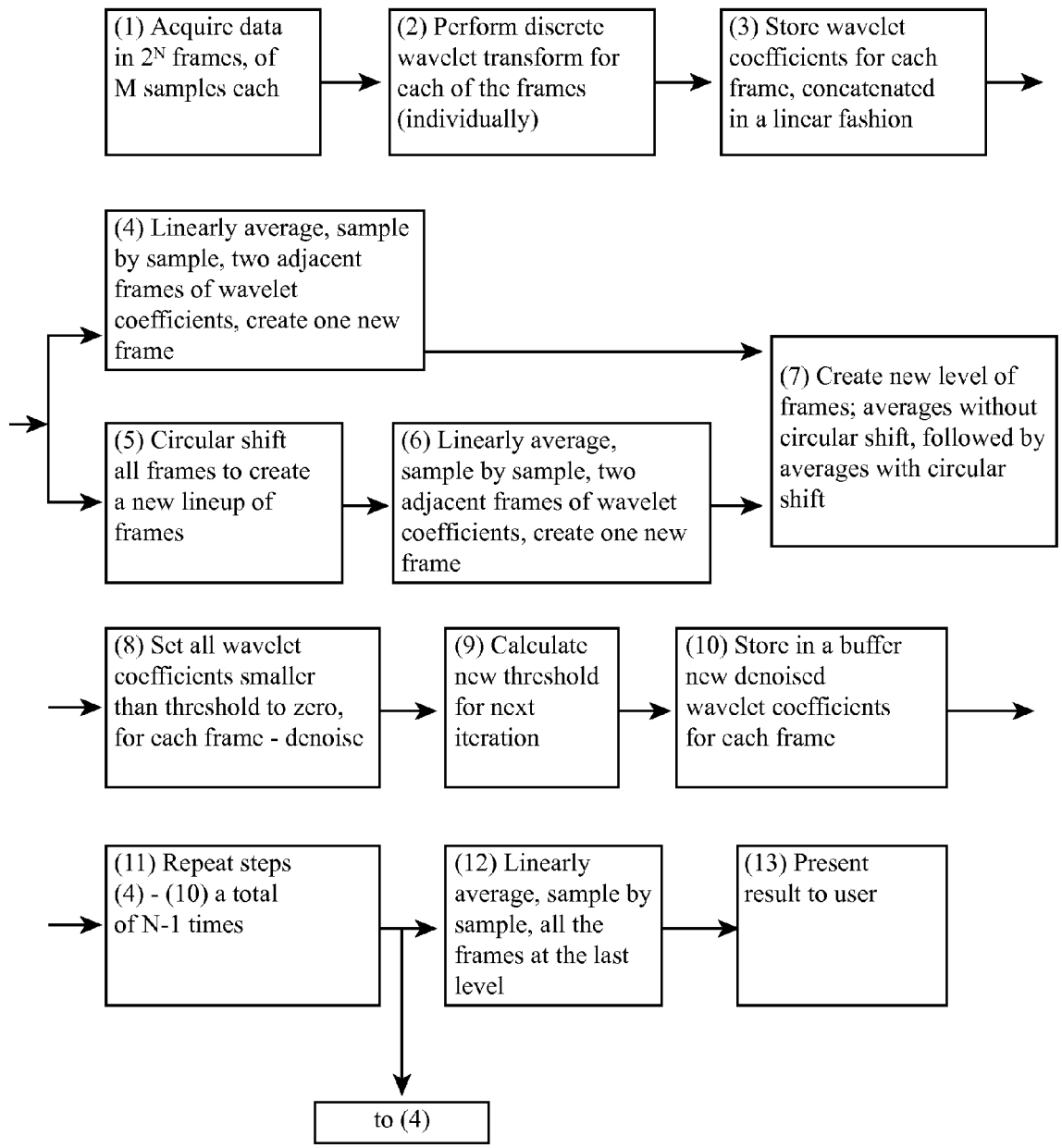
FIG. 53 is a block diagram of the present invention as implemented in a method, or as may be embodied in a processor, such as a computer

As shown in FIG. 53, the method of the present invention preferably comprises first acquiring data in pairs, for a total of $2^N$ data frames, each of which has M samples each. The data frames are next subjected to a discrete wavelet transform, and the coefficients stored for further processing, in a concatenated fashion. The CSTD algorithm is next applied, as shown, to provide half of a new set of frames of wavelet coefficients with the first half provided merely by averaging adjacent frames of wavelet coefficients as determined in the initial discrete wavelet transform. The new set of frames are then de-noised according to what may be a variable threshold, a new threshold is calculated and stored, as well as the de-noised wavelet coefficients. This is repeated iteratively, for N−1 times, and the resultant coefficients are linearly averaged. The final frame may then be inverse discrete wavelet transformed to arrive at the de-noised signal.

Two items are important to note about CSTD algorithm. First, without de-noising, frame recombinations using cyclic-shift tree averaging yield simple linear combinations of frames at each new level. A linear average of frames at any particular level is identical to the linear average of frames at all other levels. The second item to note is that at the bottom of the CSTD tree, each frame is identical to every other frame. This is because the cyclic shift algorithm, without de-noising, assures that each frame at the bottom is the linear average of all the frames at the original level, and that they are included in that average at most once. These two results make the cyclic-shift tree algorithm desirable for investigation of wavelet de-noising.

When the thresholding of wavelet coefficients is applied to the frames at each new level, those frames are not a linear combination of the frames at the previous level, because thresholding is a non-linear operation. Additionally, the frames at the bottom level of the tree, are also a function of the ordering of the frames at the top level of the tree. For example, an application of CSTD to an ordering of frames {1,2,3,4,5,6,7,8} will produce eight frames at the bottom level of the tree that are different from the frames produced when CSTD is applied to an ordering of frames i.e., {5,3,8,1,7,6,4,2}. This is because of the variation of the threshold as a function of the CSTD level. Each frame traverses a different path from the top of the tree to the bottom, and is affected differently by the thresholding function at each new level. This fact offers a possibility of creating a very large number frames that are not linear combinations of each other by simply reordering the frames at the top level of the tree and re-applying the CSTD. There are two algorithms that produce these reorderings. These new algorithms are called "Euler-Fermat frame reordering", and "all possible permutations." Neither one of these algorithms applies any operation on the frames, like averaging or de-noising, they only reorder the sequence of frames in a predictable fashion.

The CSTD algorithm does not exhaust all possibilities of frame recombination. It is possible to rearrange the frames prior to application of CSTD, which will yield more overall combinations. What is needed is a one-to-one and onto function from the set of {1, 2, . . . , N} to a new set that contains the same elements, one of each, and of length N, i.e., {7, 19, . . . , N, . . . , N-93}, or {73, 4, . . . , N, . . . , N-121}. One way to accomplish this is to use a sequence permutation result from abstract algebra, due to Euler and Fermat. We first present a theorem by Euler that uses a function $\phi(k)$ defined as follows: $\phi(1)=1$; for k>1, $\phi(k)$ equals the number of positive integers less than k, and relatively prime to k. Modulo function, denoted mod, gives the remainder of dividing two integers. For example, 3 mod 8=3, 11 mod 8=3, and 16 mod 8=0. The Euler theorem uses the congruence modulo function, denoted $x \equiv y \mod z$, to represent that x mod z is an equivalence relation with y mod z. For example, $73 \equiv 4 \mod 23$, because 73 mod 23=4, and 4 mod 23=4. Hence, we say that 73 and 4 are congruence modulo 23, meaning that both 73 and 4 divided by 23 have the same remainder, namely 4. We use the congruence modulo function to create a new sequence of frame numbers. The theorem is given without proof, as follows:

(Euler) $a^{\phi(k)} \equiv 1 \mod k$ where k is a positive integer and a is relatively prime to k. For example, let k=8. Then $\phi(8)=4$, because there are four numbers (1, 3, 5, 7) less than 8 that are relatively prime to 8. Hence any of these four numbers raised to the $\phi(8)=4^{th}$ power, are congruence modulo 8 with 1, i.e., $1^4=1$, 1 mod 8=1. Also $3^4=81$, 81 mod 8=1. Likewise, $5^4=625$, 625 mod 8=1. Finally, $7^4=2,401$, and 2,401 mod 8=1.

A second theorem, due to Fermat (not his last theorem that was just recently proved), extends this concept to prime numbers. We also state this theorem also without proof:

(Fermat) If p is a prime number and a is any integer, then $a^p \equiv a \mod p$.

For example, let a=8, and p=3. Then $8^3=512$, and 512 mod 3=2. Likewise, 8 mod 3=2. Hence, we say that $8^3 \equiv 8 \mod 3$, or that $8^3$ and 8 are congruence modulo 3, meaning that both $8^3$ and 8 divided by 3 have the same remainder, namely 2.

For a particular number of frames (which needs to be power of 2 for CSTD purposes) we can find a set of prime numbers that yield the largest number of possible reorderings. Particularly, if N denotes the number of frames, p is a number relatively prime to N, and $i_{old}$ is the index of old frames, then index of new frames $i_{new}$ is given by the following equation:

$i_{new} = (i_{old} \cdot p) \mod N$

See, Wickerhauser, M. V., *Personal Communications*. For example, if N=8, Table 3 below provides an example of Euler-Fermat frame index reordering and indicates reorderings of 8 original frames for values p=1, 3, 5, and 7.

| p | Frame 0 | Frame 1 | Frame 2 | Frame 3 | Frame 4 | Frame 5 | Frame 6 | Frame 7 |
|---|---|---|---|---|---|---|---|---|
| 1 | 0 | 1 | 2 | 3 | 4 | 5 | 6 | 7 |
| 3 | 0 | 3 | 6 | 1 | 4 | 7 | 2 | 5 |
| 5 | 0 | 5 | 2 | 7 | 4 | 1 | 6 | 3 |
| 7 | 0 | 7 | 6 | 5 | 4 | 3 | 2 | 1 |

Notice that each new reordering of frames has exactly N=8 elements, and that each element in the original set appears in the reordering only once.

With the help of a simple computer program, we can find the appropriate prime numbers for a given number of frames of original data. We iterate the equation x=(p*x) mod N, n times, until x=1, and that gives us $p^n$=1 mod N. We want to maximize the number of iterations n for a given prime. For example, for N=512 frames of data, numbers 3,5,11,13,27 (which are all relatively prime to 512) produce n=128, so that for these relative primes $p^{128}$=1 mod 512. Relative primes 7 and 9 produce n=64, and the relative prime 17 produces n=32. Hence we select primes 3,5,11,13,27, etc. If N is a power of two, the maximum number of permutations of the original sequence of N elements is equal to N/2. For example, for N=512, the maximum number of different permutations is 256, and all odd numbers less than 512 are relatively prime to 512.

The Euler-Fermat algorithm is implemented to increase the total number of different frame index reorderings prior to the application of CSTD. The overall algorithm first creates many reorderings of original N frames using the Euler-Fermat method described here, and then applies CSTD algorithm to each new reordering of frames. If P new rearrangements are generated using the Euler-Fermat reorderings, this creates a total of M=P*N*log$_2$(N) new frames. We then have an upper bound of the maximum number of frames that can be generated by the combination of Euler-Fermat reorderings and CSTD: M=N*N/2*log$_2$(N)=0.5*(N$^2$*log$_2$(N)).

To create a large number of frames, the most exhaustive choice was to simply calculate all possible permutations, and then dyadically average and de-noise those. However, the number of all possible permutations is N!, which grows very quickly even for a small number of frames. For example, for N=8, the number of all possible permutations is M=40,320, and for N=512 frames the number of all possible permutations is M=3.4*10$^{1166}$. This algorithm was not investigated in the lab, because the combination of Euler-Fermat reorderings and CSTD already produced a very large number of frames, sufficient for evaluation of the novel de-noising algorithm.

Figure 21:
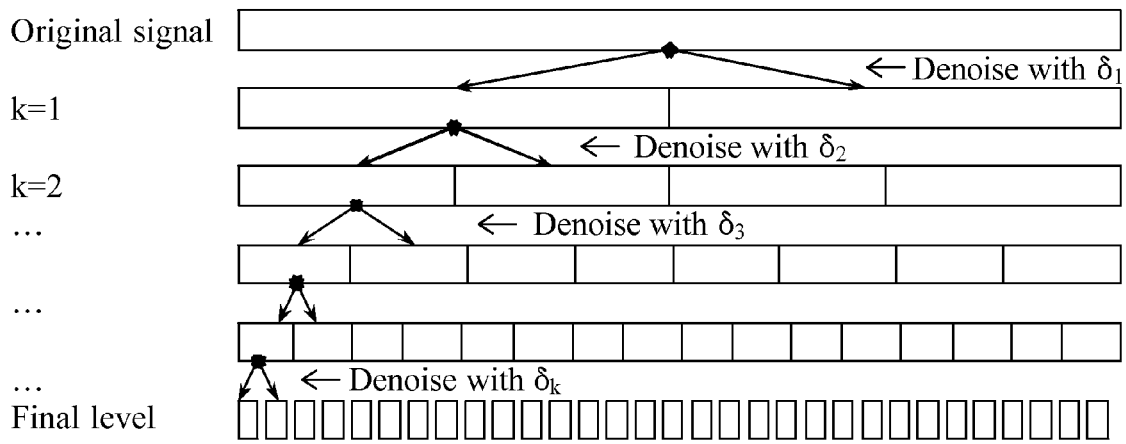
FIG. 21 is a graph showing a cyclic shift denoising algorithm.

FIG. 21 depicts the CSTD process graphically, for a particular Euler-Fermat permutation. The original signal x[n] is composed of N frames of ABR data. For example, let N be 32, then CSTD produces 32*log$_2$(32)=160 new frames in 5 levels.

We now examine the process of thresholding of wavelet coefficients. Thresholding is applied in two different ways. The first way thresholding is applied is within a single DWT. At each level of wavelet decomposition, a different threshold is applied that affects coefficients at different scales differently. Wavelet decomposition scales corresponding to higher frequencies are thresholded with a larger threshold, and as the scale increases with additional levels of decomposition, and the features of the signal are more prominent, fewer coefficients are set to zero. This is the result summarized by Donoho in the prior art. The number of wavelet coefficients corresponds to number of samples in the data frame, and hence wavelet decomposition of a 64 point signal frame yields log$_2$(64)=6 decomposition levels, and 64 wavelet coefficients. This thresholding is implemented in the novel algorithm as suggested in standard wavelet de-noising literature, such that the threshold level drops from scale to scale by a factor of $2^{i/2}$, where i is the wavelet decomposition level. This is a standard method and will not be discussed further.

The second way variable thresholding is implemented is between CSTD levels as depicted in FIG. 21, which is unique to the present invention. Wavelet coefficients are thresholded for each frame at that level with a different initial threshold, denoted $\delta_1$. The correct way to interpret the threshold function is as a function of two variables: $\delta_{k,w}$, where k is the index corresponding to the CSTD algorithm level, and w is the index corresponding to the particular wavelet scale within a single frame, at the k$^{th}$ level of CSTD. Since the within-wavelet-scale thresholding is a part of existing, standard de-noising algorithm, we will not examine it further here, and future discussion of thresholding will assume that. We will only be examining the variation of δ as a function of the CSTD level k—denoted $\delta_k$. When we discuss thresholding, we will exclusively refer to CSTD level-dependent thresholding applied to the present invention.

There are two variables involved with CSTD wavelet coefficient thresholding. First is the function relating the threshold with tree depth level. Second is the initial value ($\delta_1$) at the first level. Both play an important role in the effectiveness of the present invention.

We have many choices when selecting the underlying function that relates δ to the CSTD level. The function $\delta_k$ is selected from a range of commonly used signal processing functions in search of one that minimizes the variance of the estimator. Intuitively, we want to select a monotonic function, either a strictly-increasing, strictly-decreasing, or a constant function, because the behavior of the CSTD is consistent from level to level.

Figure 22:
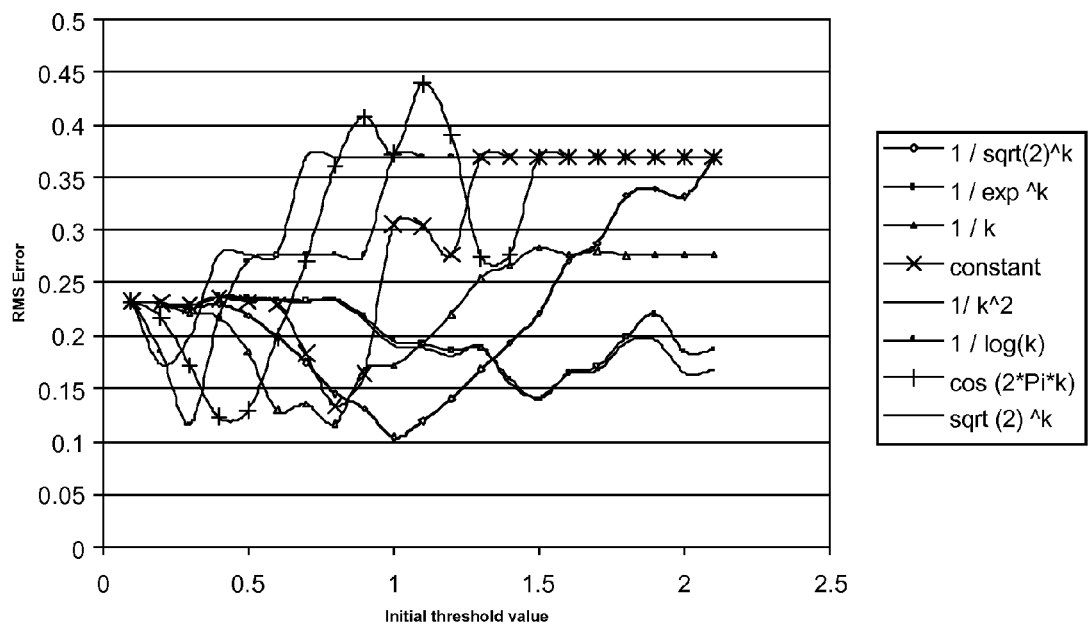
FIG. 22 is a graph showing a threshold function selection plotted for 6 decreasing functions, a constant function and one increasing function (sqrt(2)^k)
Figure 23:
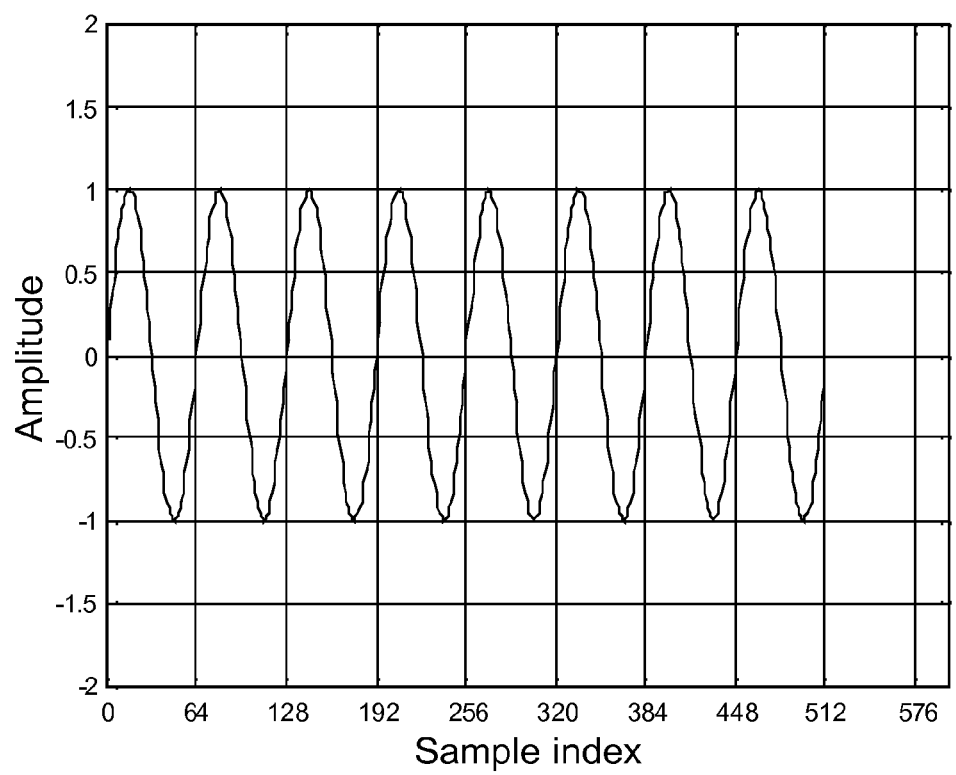
FIG. 23 is a graph showing a eight cycle sinewave.
Figure 24:
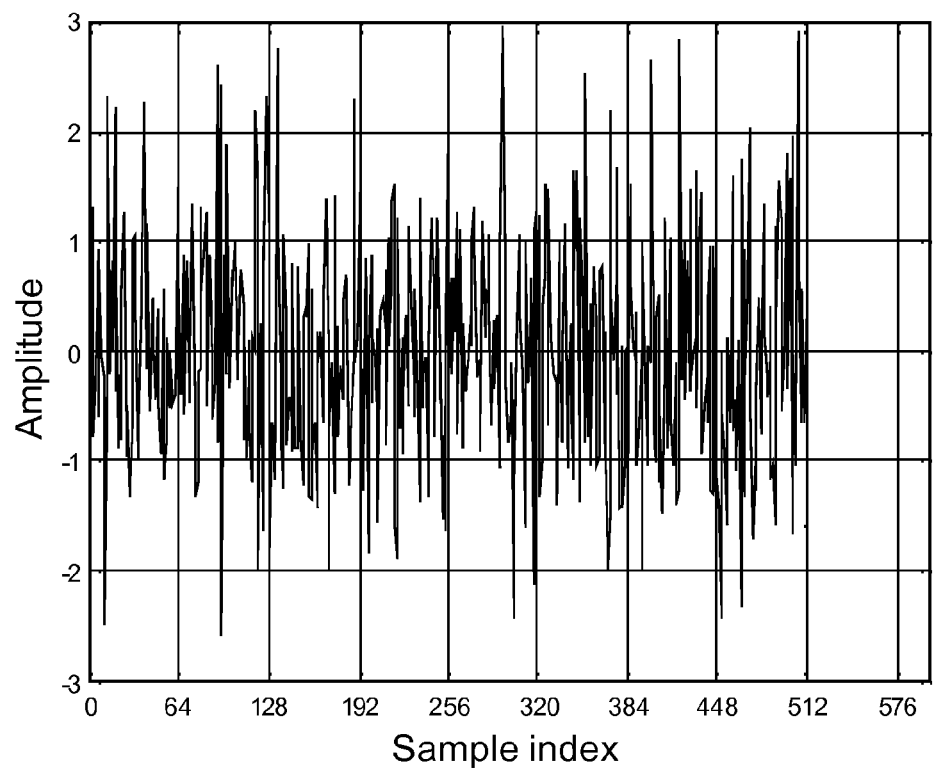
FIG. 24 is a graph showing a time domain of WGN~N [0.1]
Figure 25:
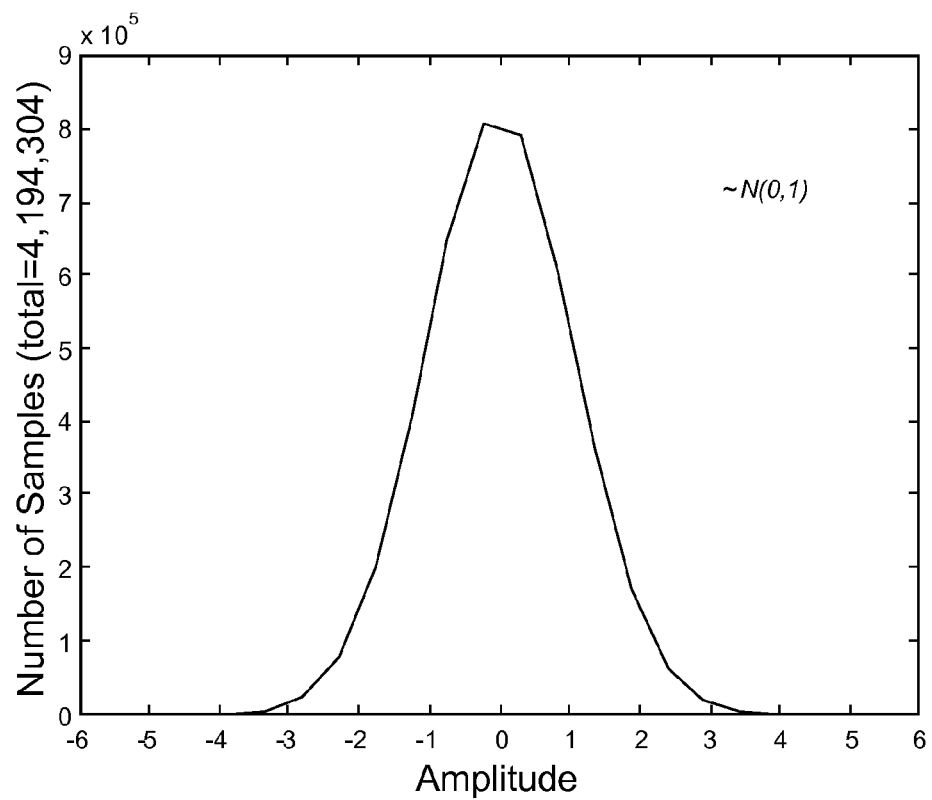
FIG. 25 is a histogram of the random noise vector (mean 9.1848e−005, variance=0.999)
Figure 26:
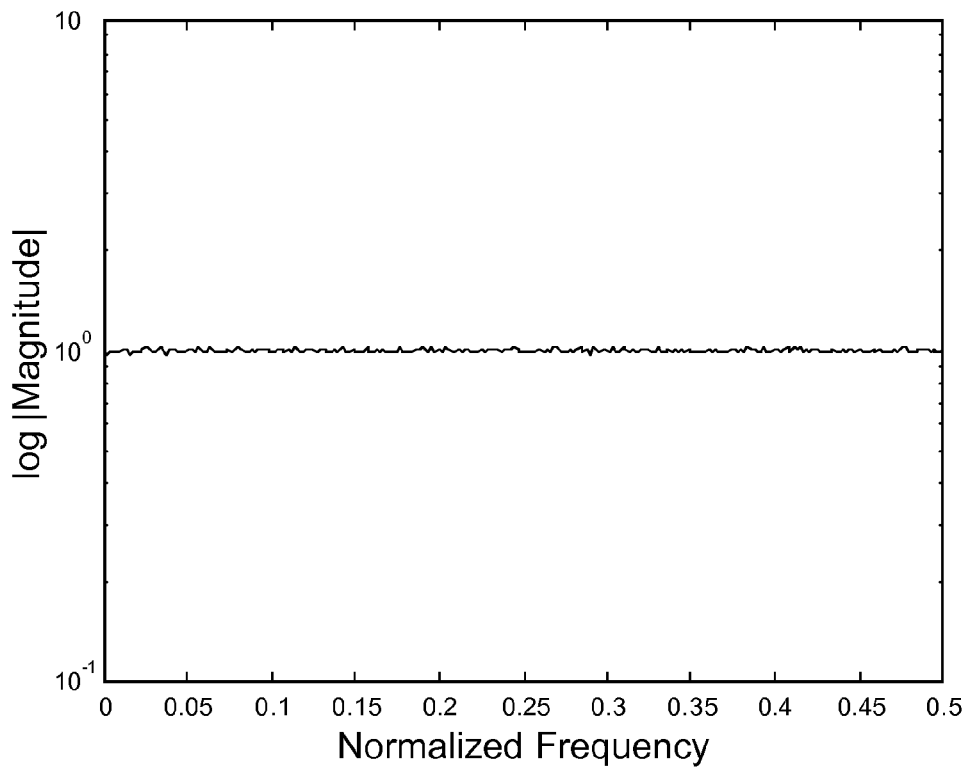
FIG. 26 is a graph showing power spectral density of the random noise vector.
Figure 27:
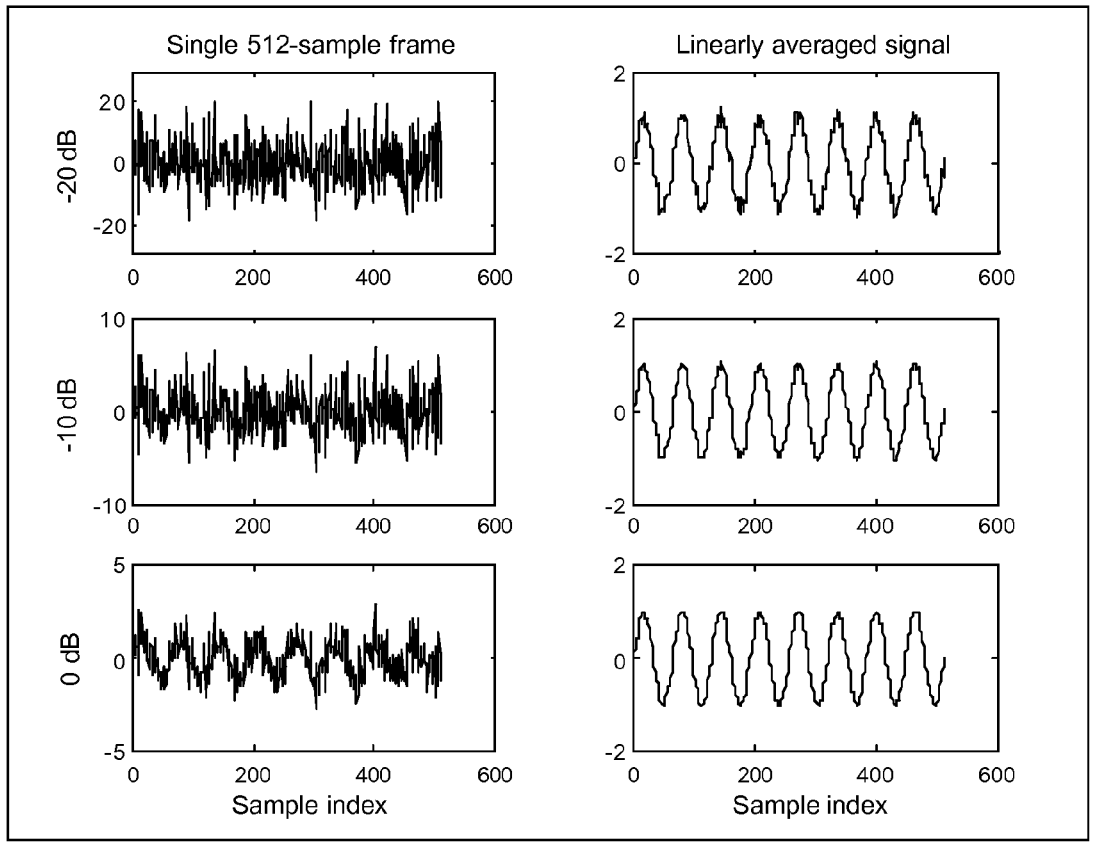
FIG. 27 is a series of graphs showing noisy sinewaves and their linea averages wherein the left column shows three single frame sinewaves with SNRs of −20 dB, −10 dB and 0 dB with added WGN, top to bottom and the right columns shows the respective sinewaves linearly averages over all 8,192 frames.
Figure 28:
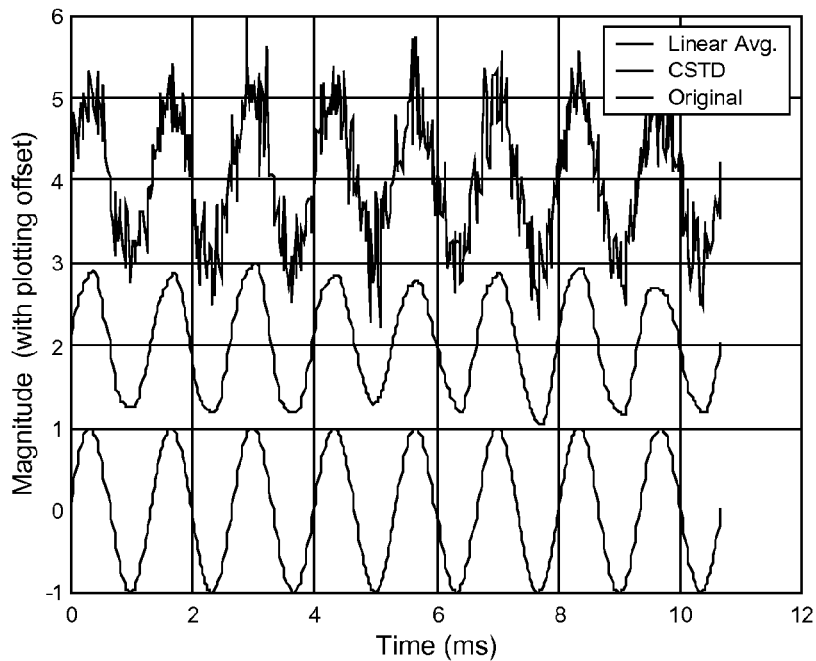
FIG. 28 is a graph showing the performance of the novel wavelet algorithm compared to linear averaging 512 data frames.
Figure 29:
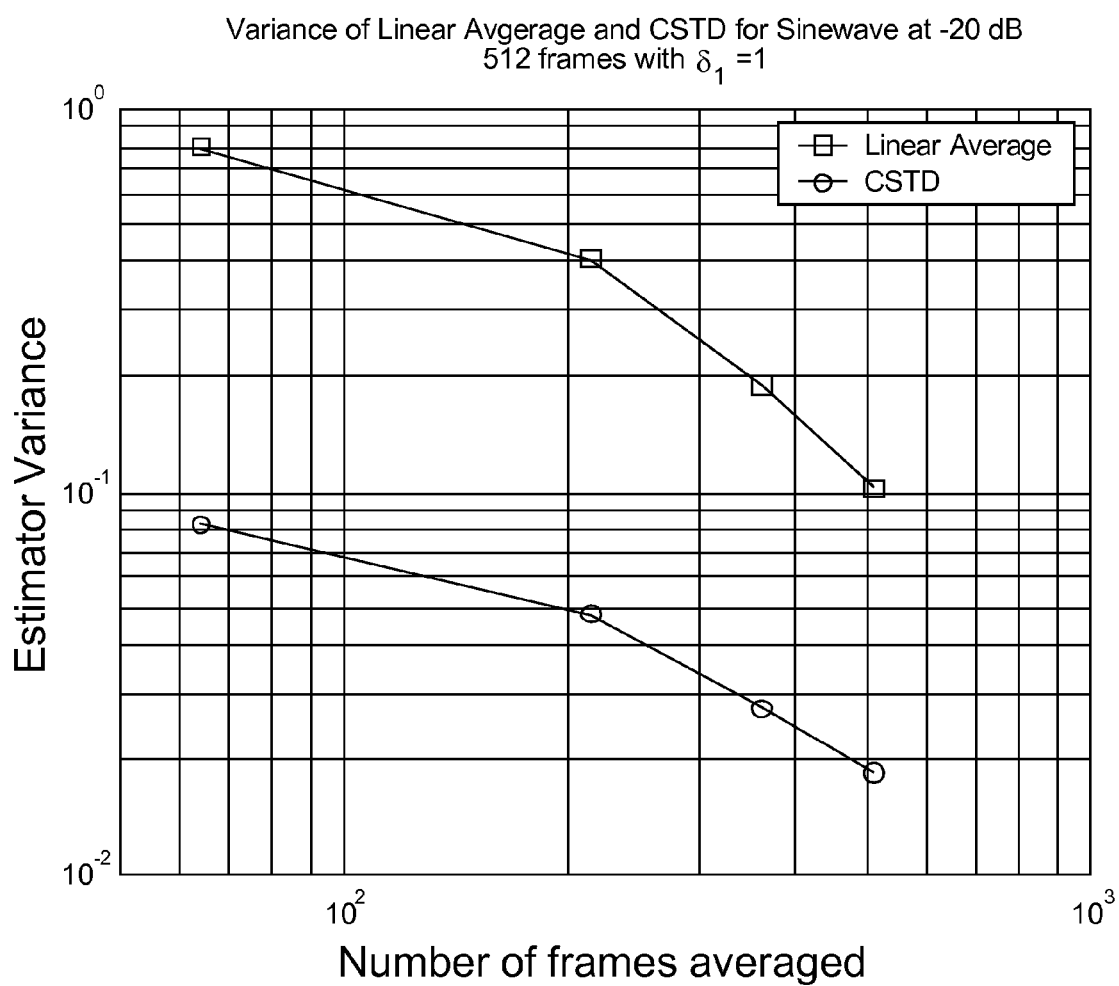
FIG. 29 is a graph showing a variance comparison between linear averaging (top) and novel wavelet algorithm (bottom)
Figure 30:
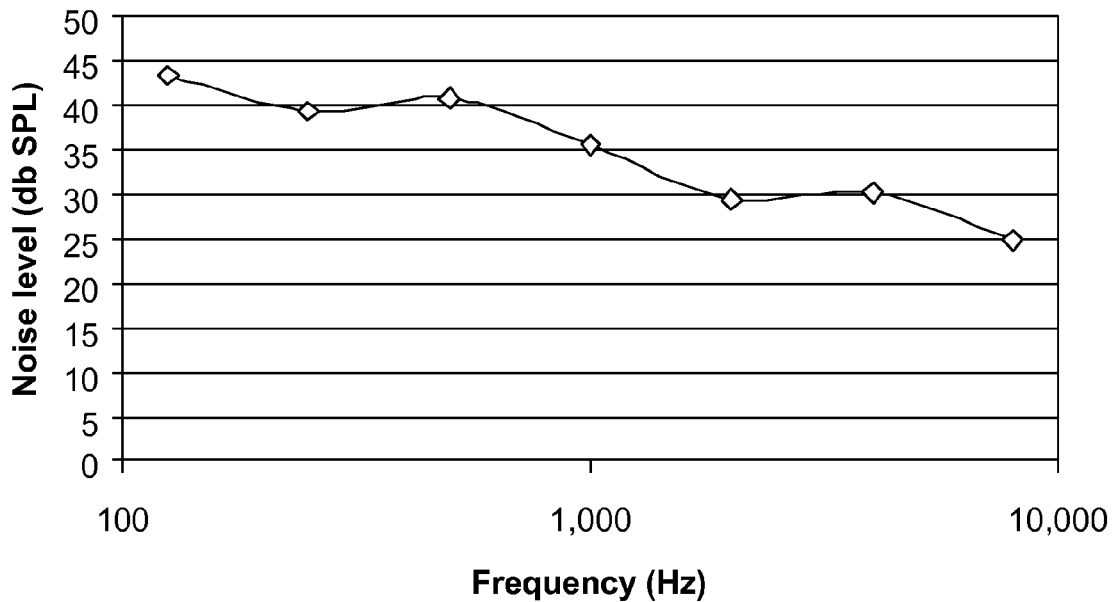
FIG. 30 is a graph showing an experimental environmental noise level measurement.
Figure 31:
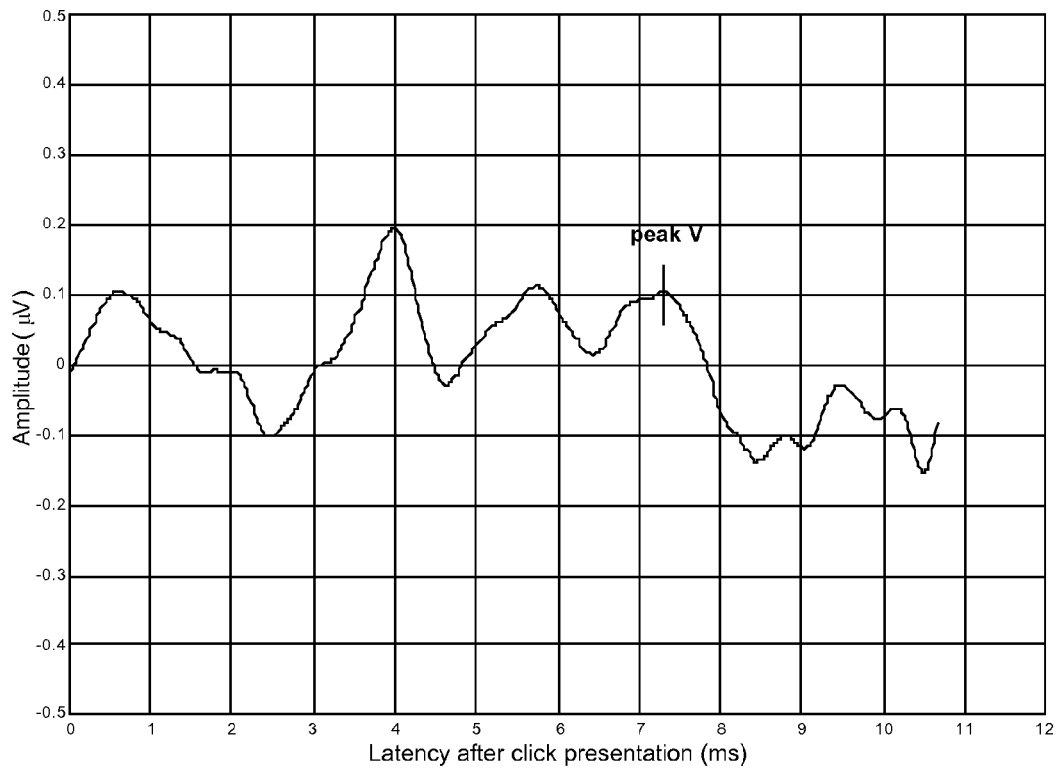
FIG. 31 is a graph showing a typical ABR wave form averages over 8,192 frames and filtered by a BP Butterwoth filter with linear phase (100-1500 Hz)
Figure 32:
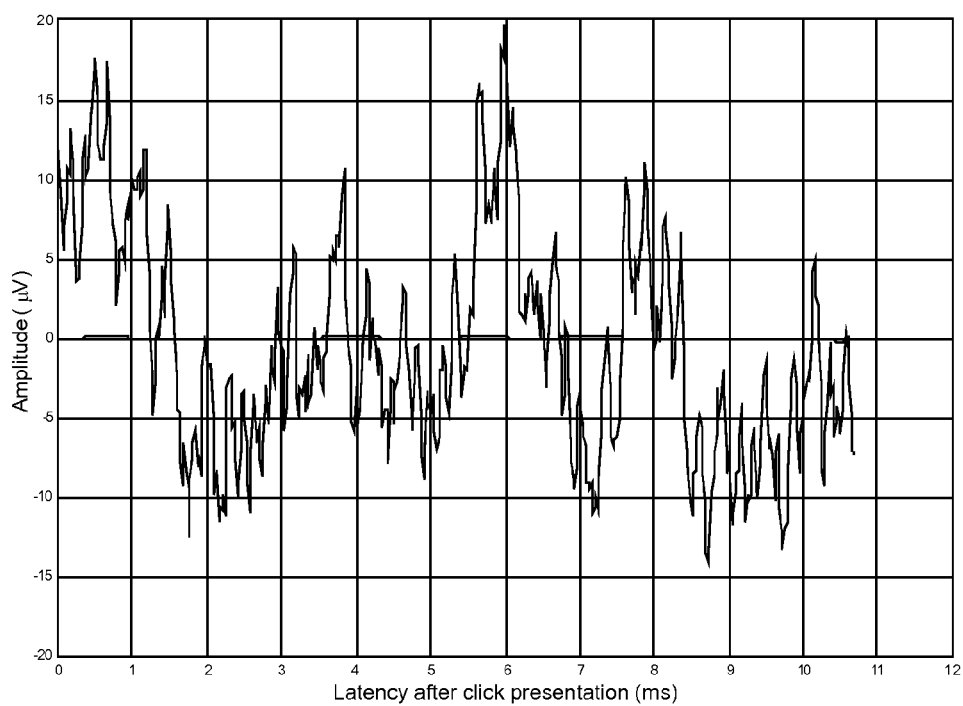
FIG. 32 is a graph showing a typical single frame of ABR data without averaging overlaid on the graph FIG. 29 represented by the darker line.
Figure 33:
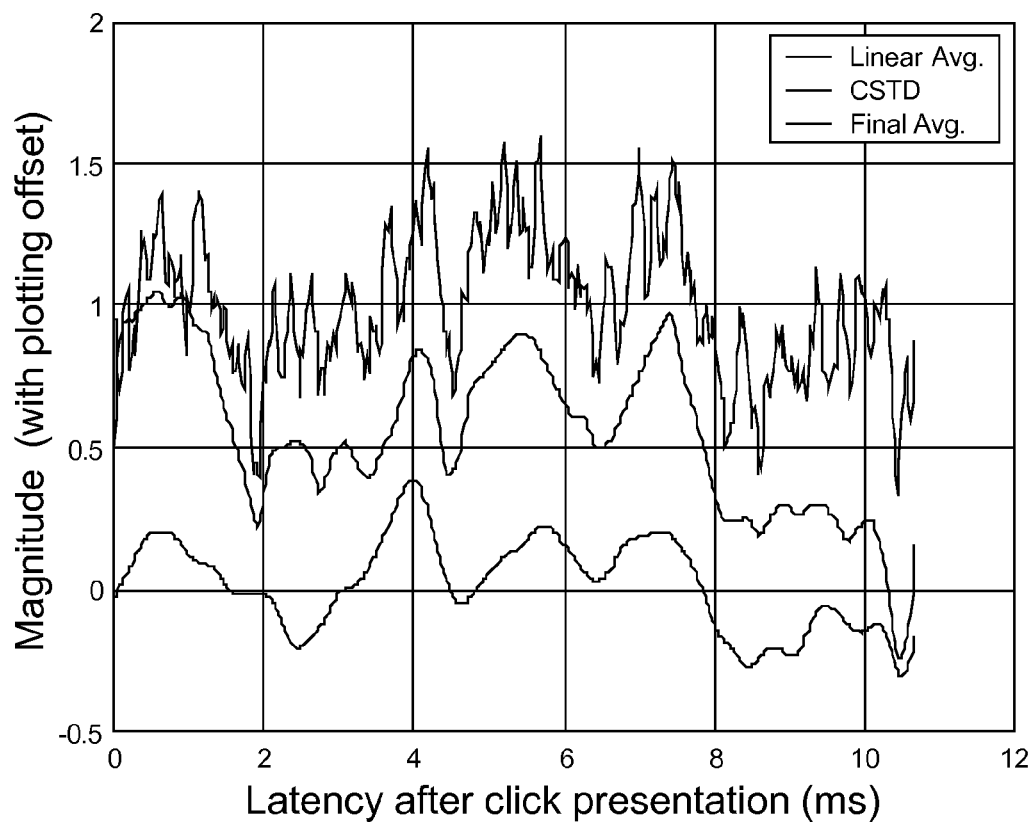
FIG. 33 is a graph showing a comparison of linear averaging to CSTD for 512 frames of data.
Figure 34:
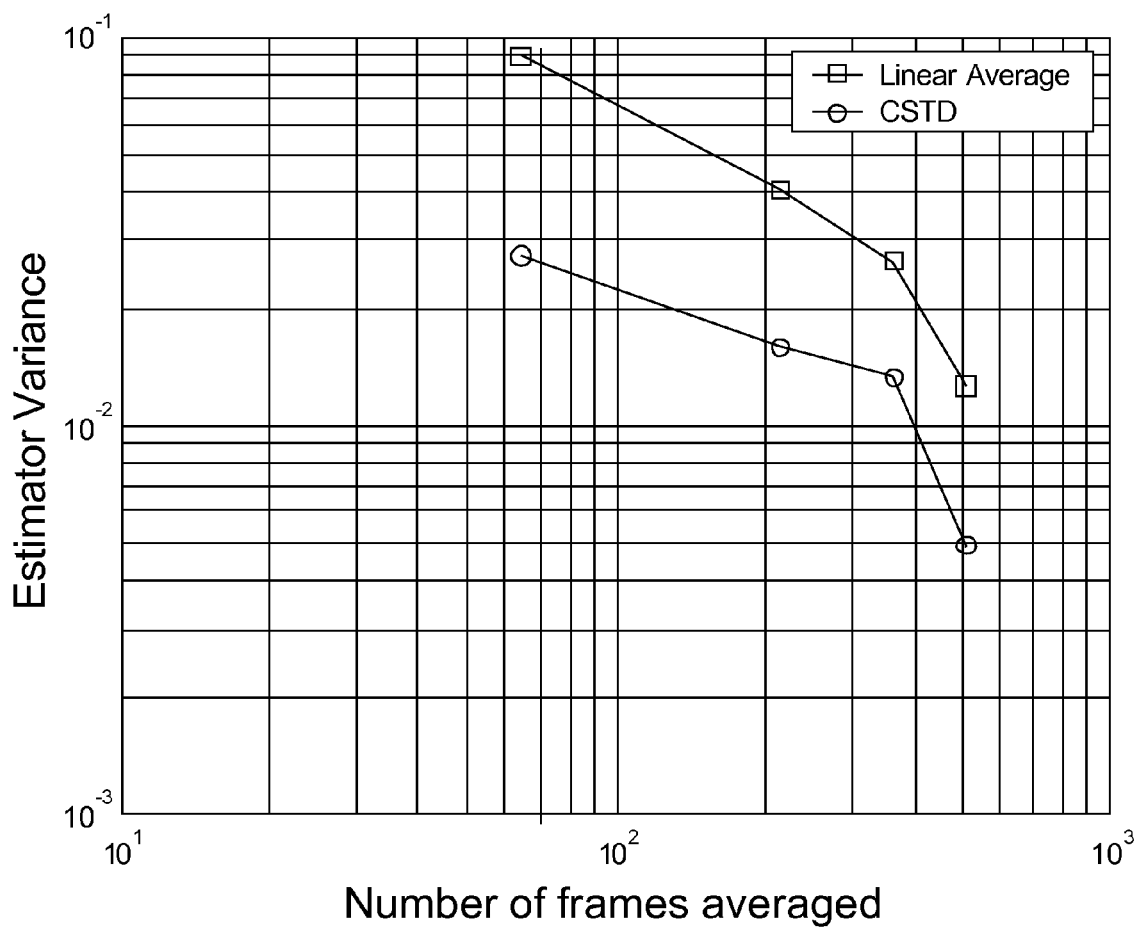
FIG. 34 is a graph showing a variance comparison between linear averaging and CSTD as a function of the number of frames.
Figure 36:
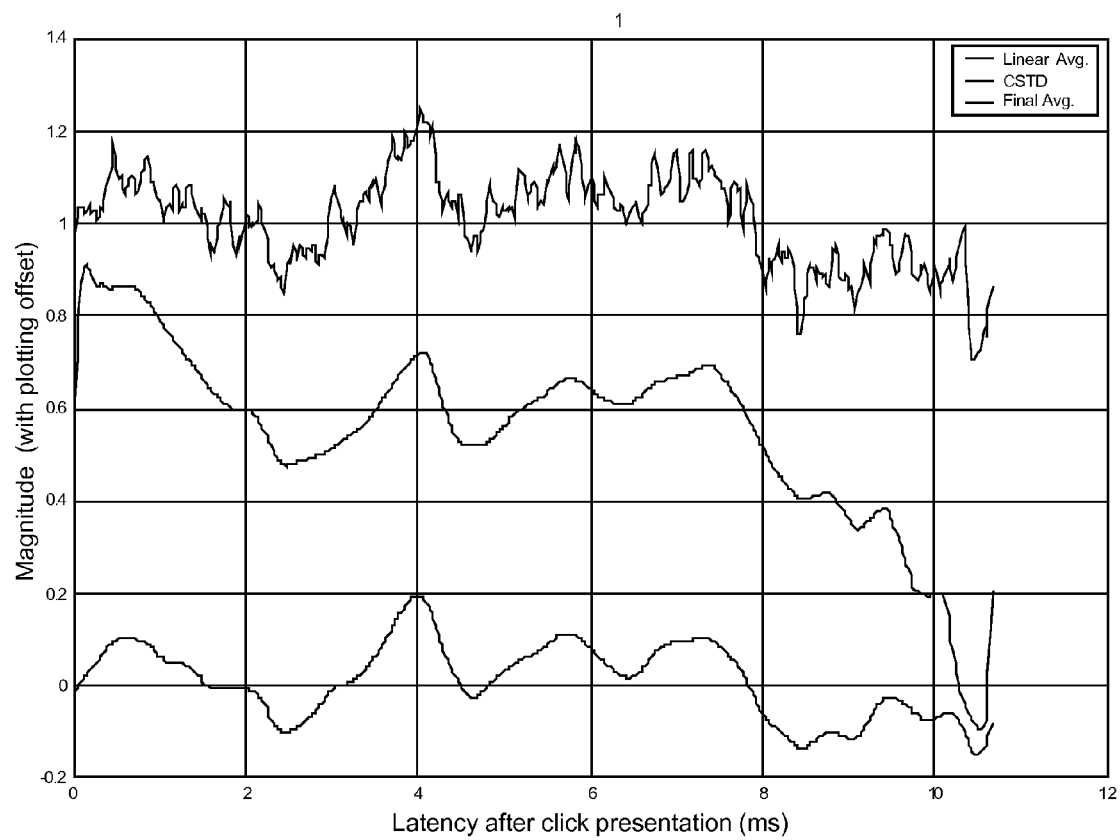
FIG. 36 is a graph showing a comparison of novel wavelet denoising to linear averaging over all 8,192 frames.
Figure 37:
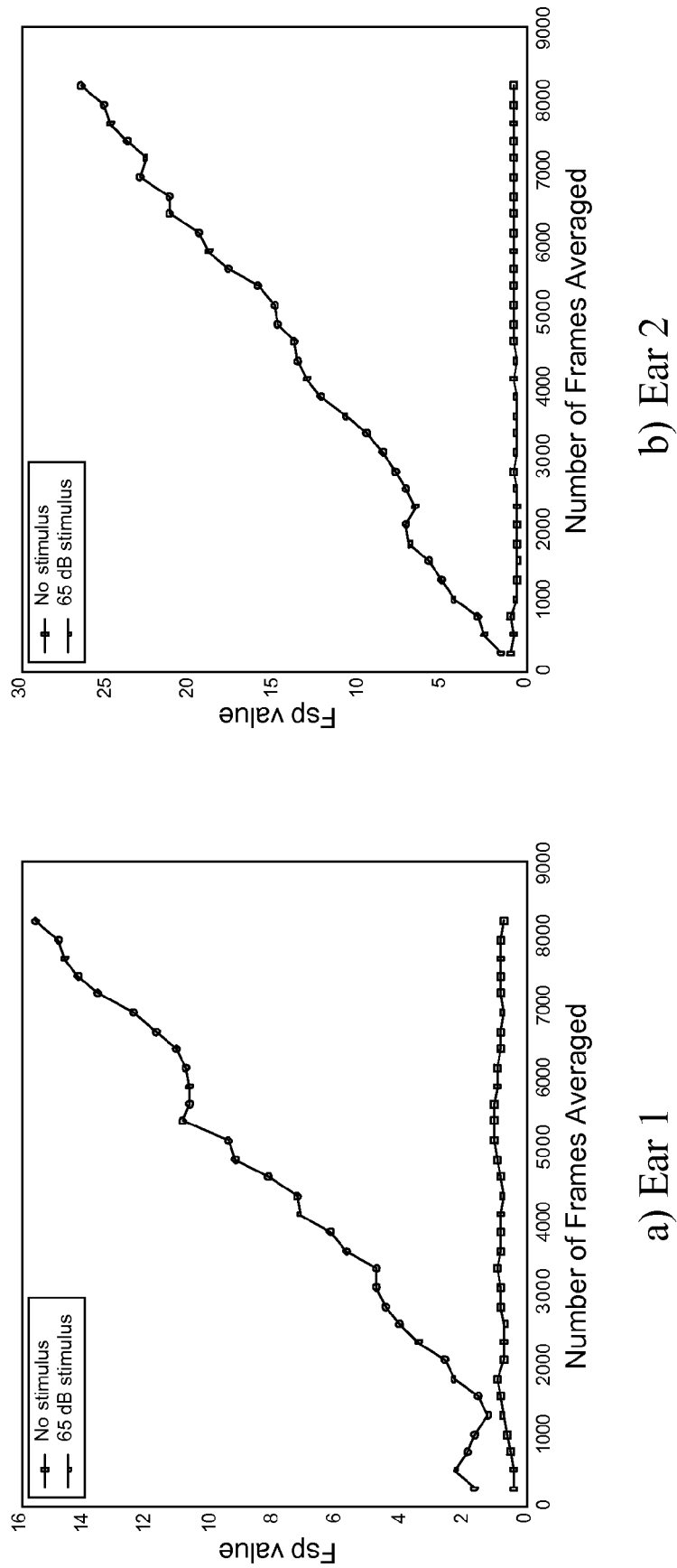
FIG. 37 is a series of graphs showing $F_{sp}$ recordings for a patient's ears (Ear 1 and Ear 2)
Figure 39:
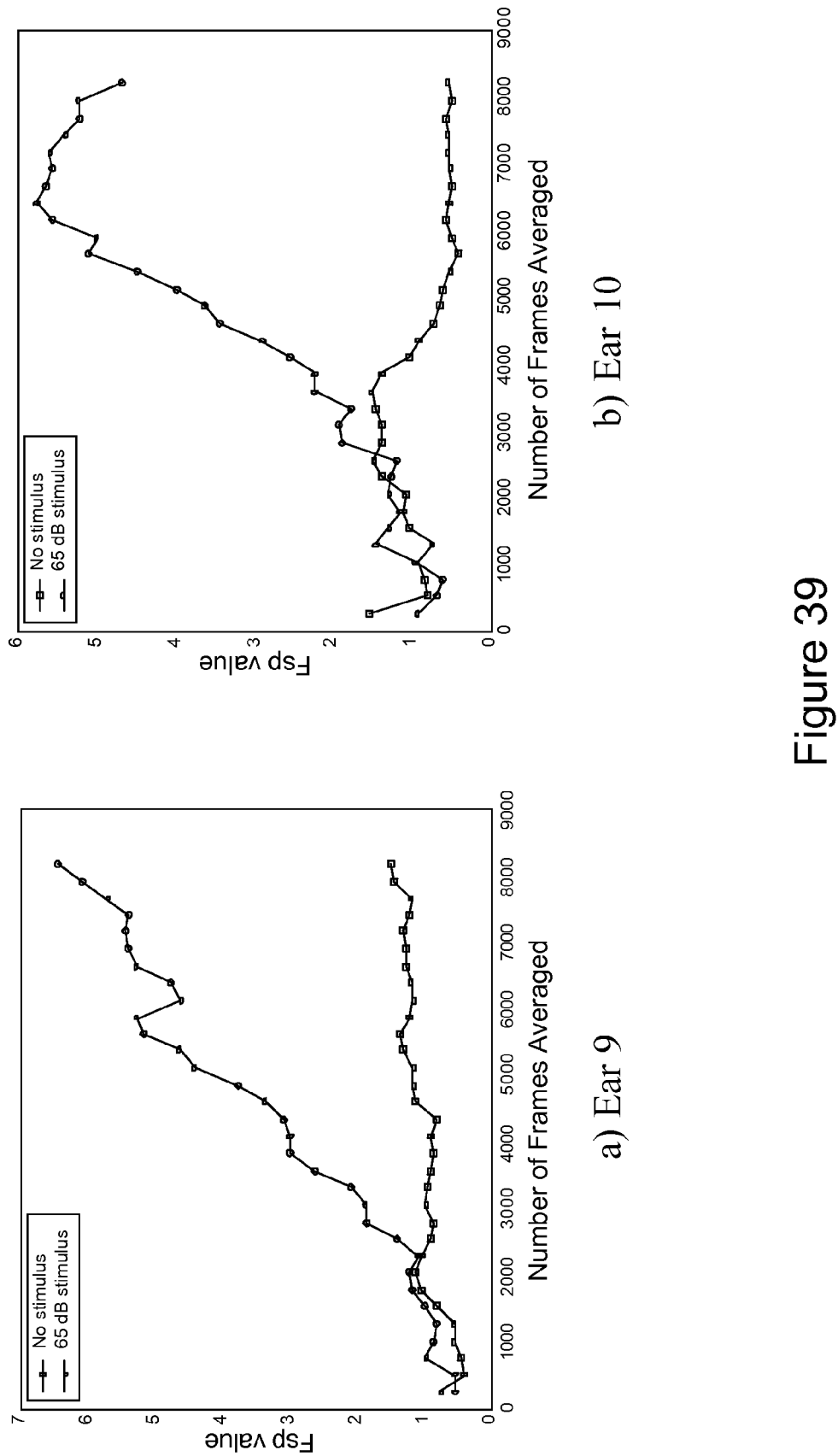
FIG. 39 is a series of graphs showing $F_{sp}$ recordings for a patient's ears (Ear 9 and Ear 10)
Figure 40:
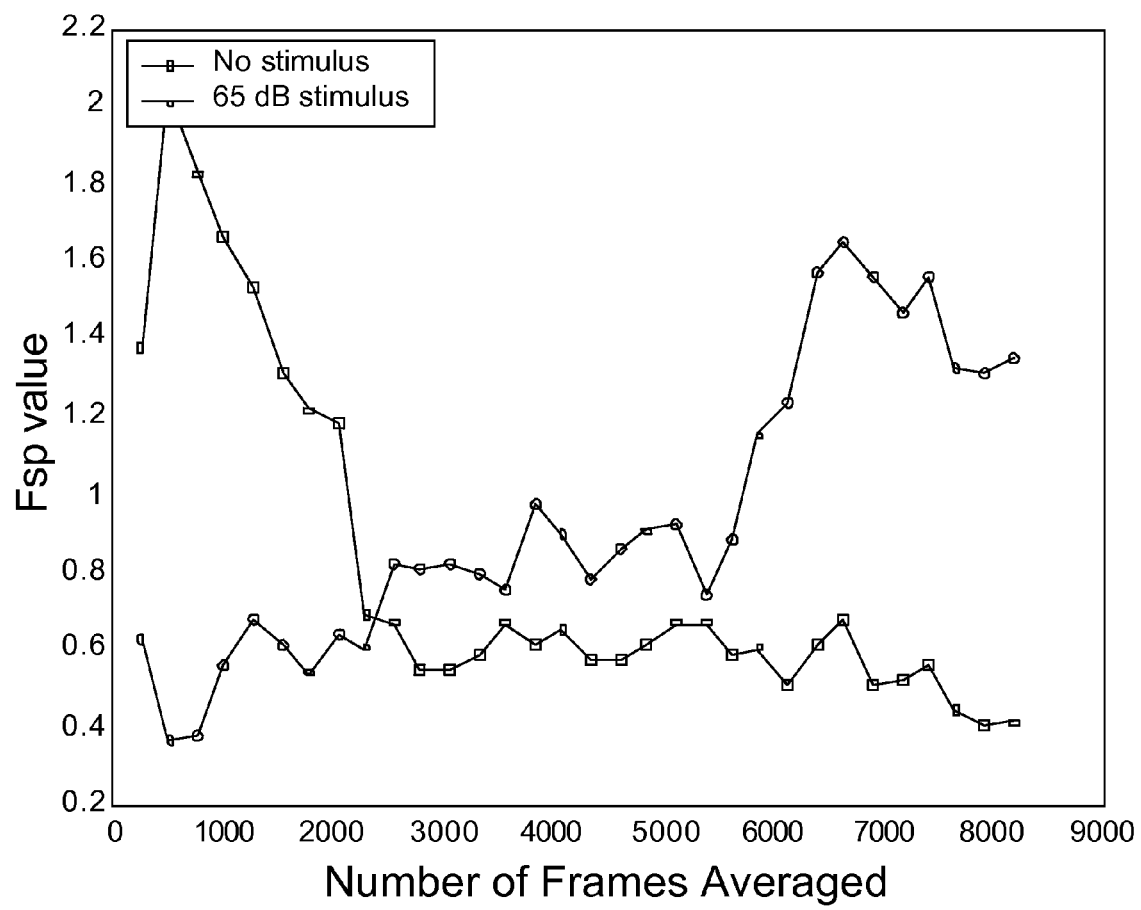
FIG. 40 is a graph of an example of invalid ABR recordings wherein the $F_{sp}$ value did not reach 3.1 and there is no general increasing trend with and increasing number of frames averaged.
Figure 41:
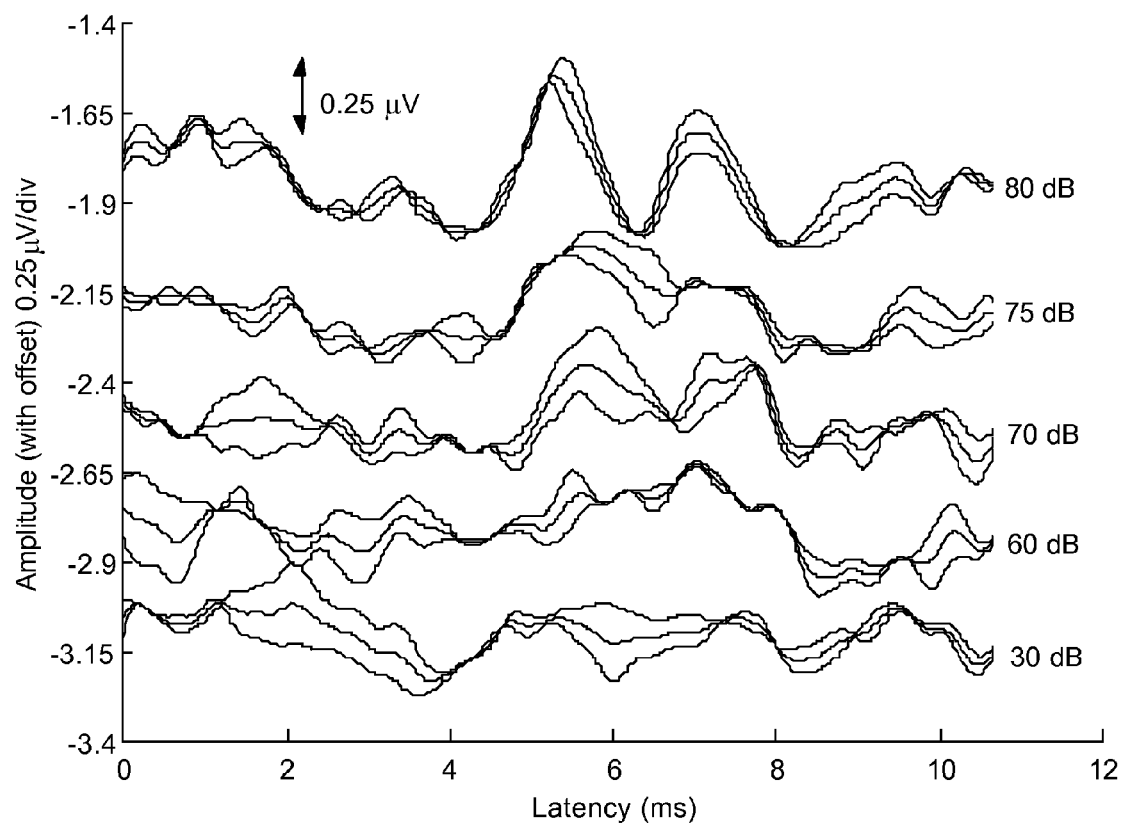
FIG. 41 is a graph of stimulus recording for a subject at 80, 75, 70, 60, and 30 dB SPL wherein three waves forms shown are overlaid for each stimulus level averaged over the following frame numbers: 1-4,096; 4,097-8,192; and 1-8, 192.
Figure 42:
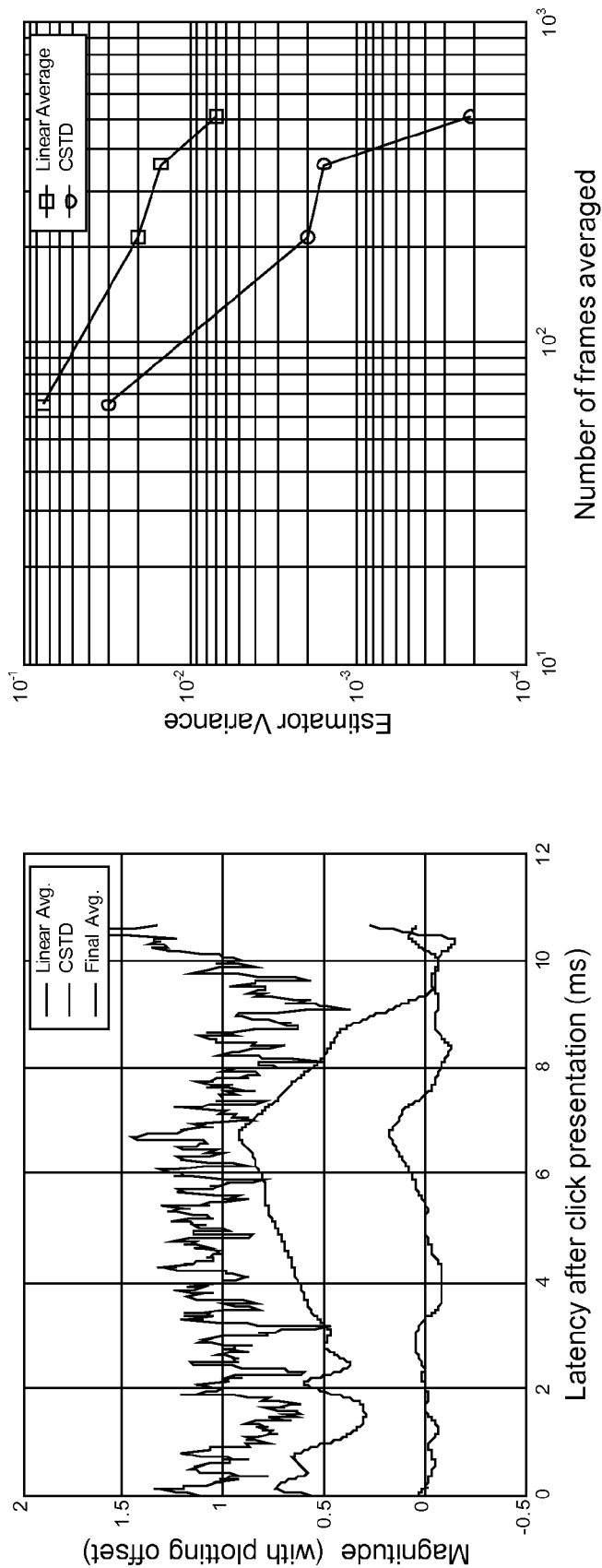
FIG. 42 is a series of graphs showing Ear 1 CSTD (left) and variance comparison (right)
Figure 43:
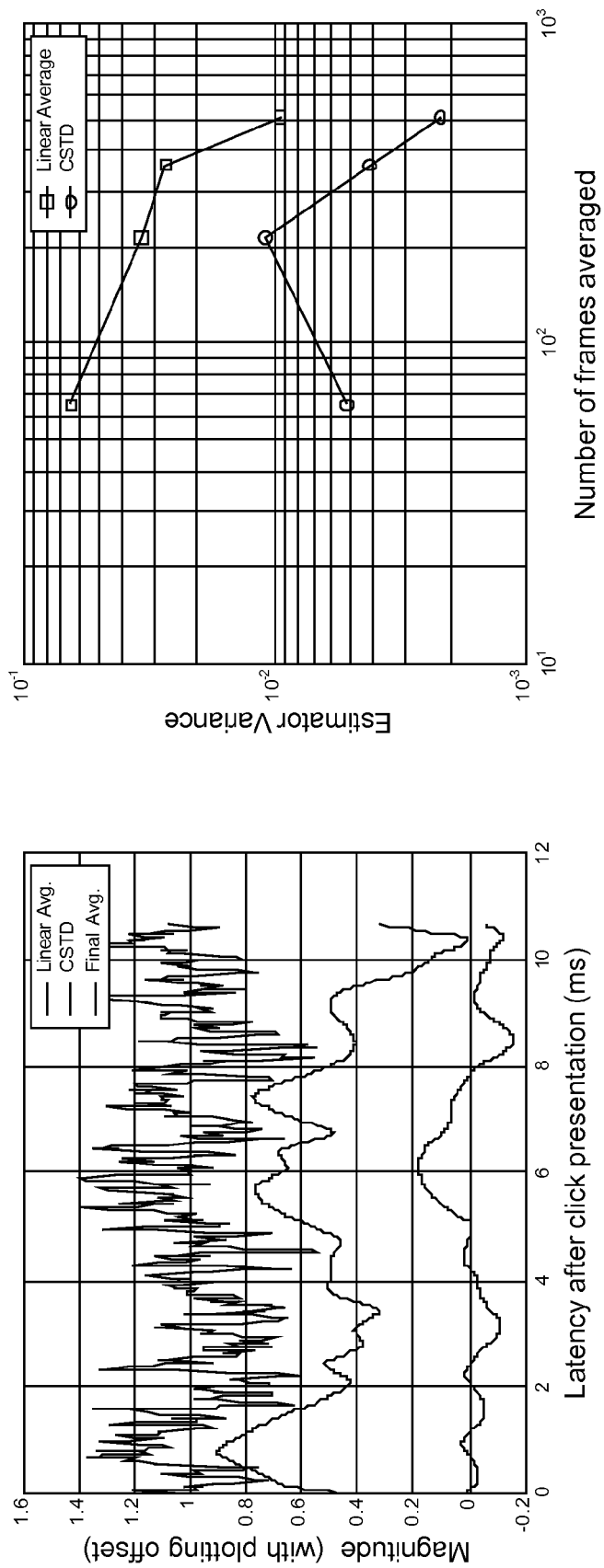
FIG. 43 is a series of graphs showing Ear 2 CSTD (left) and variance comparison (right)
Figure 44:
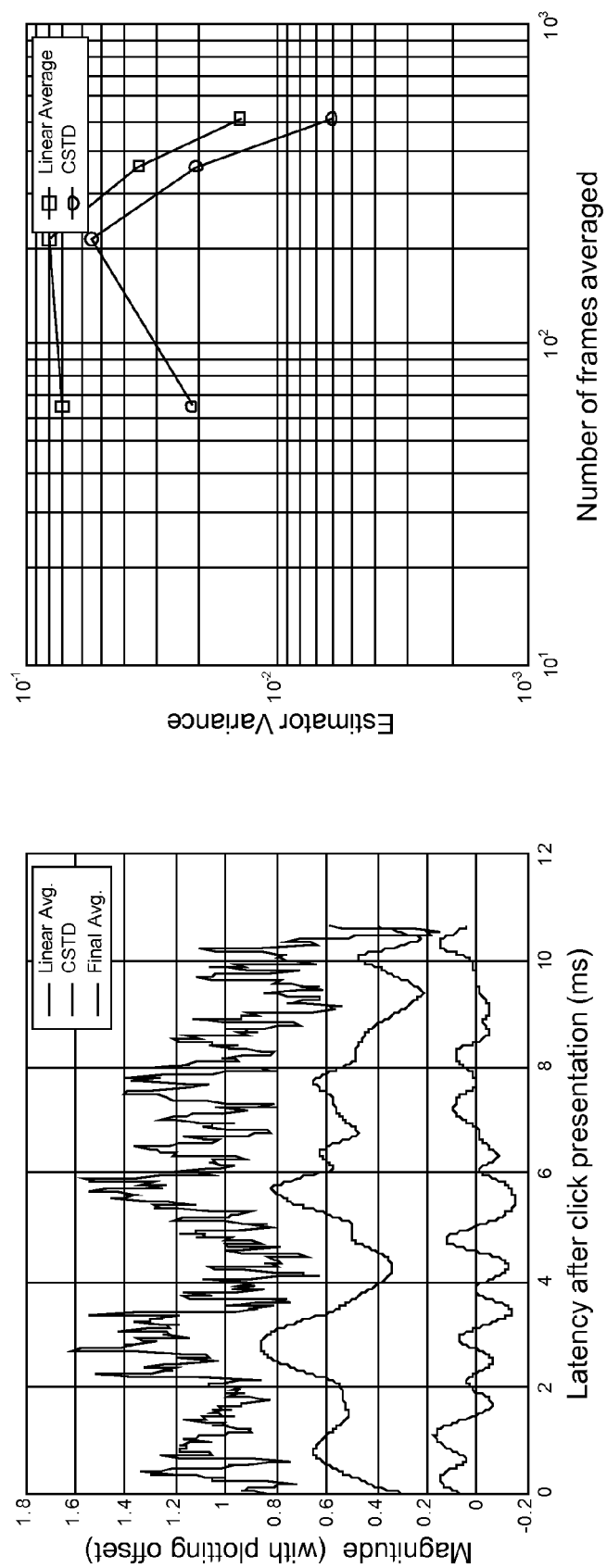
FIG. 44 is a series of graphs showing Ear 3 CSTD (left) and variance comparison (right)
Figure 45:
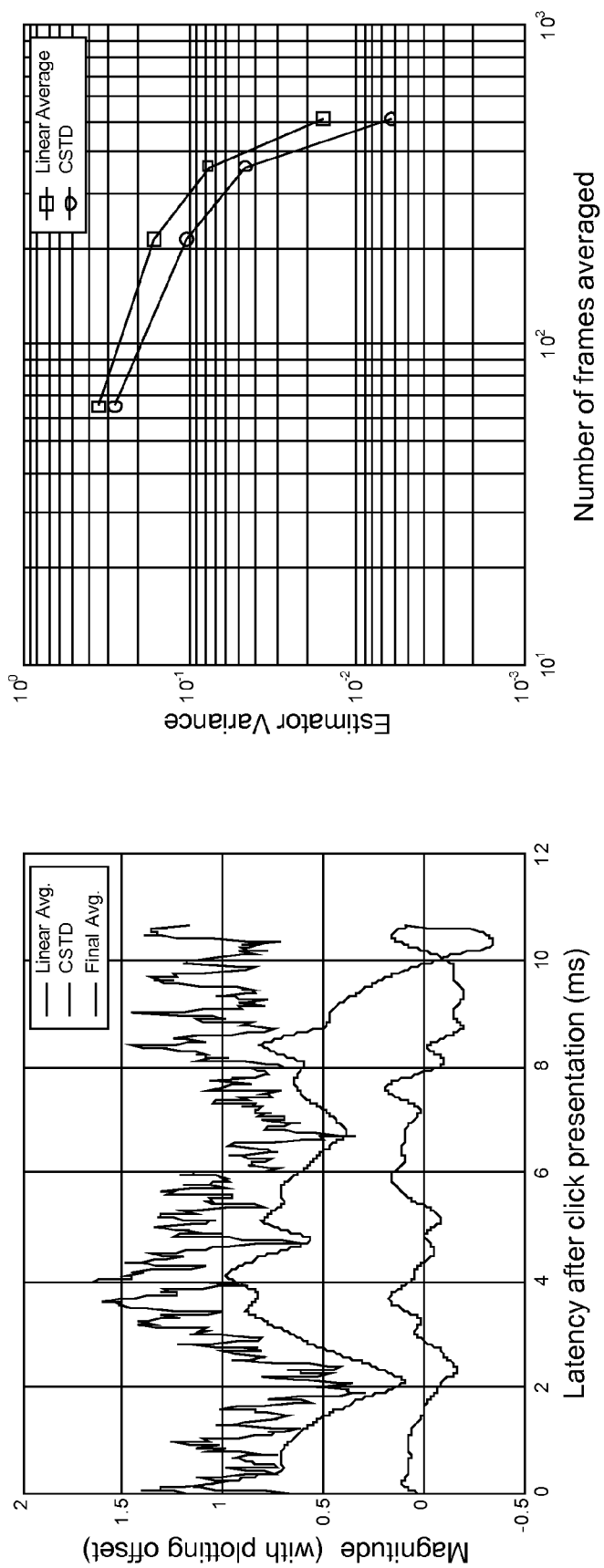
FIG. 45 is a series of graphs showing Ear 4 CSTD (left) and variance comparison (right)
Figure 46:
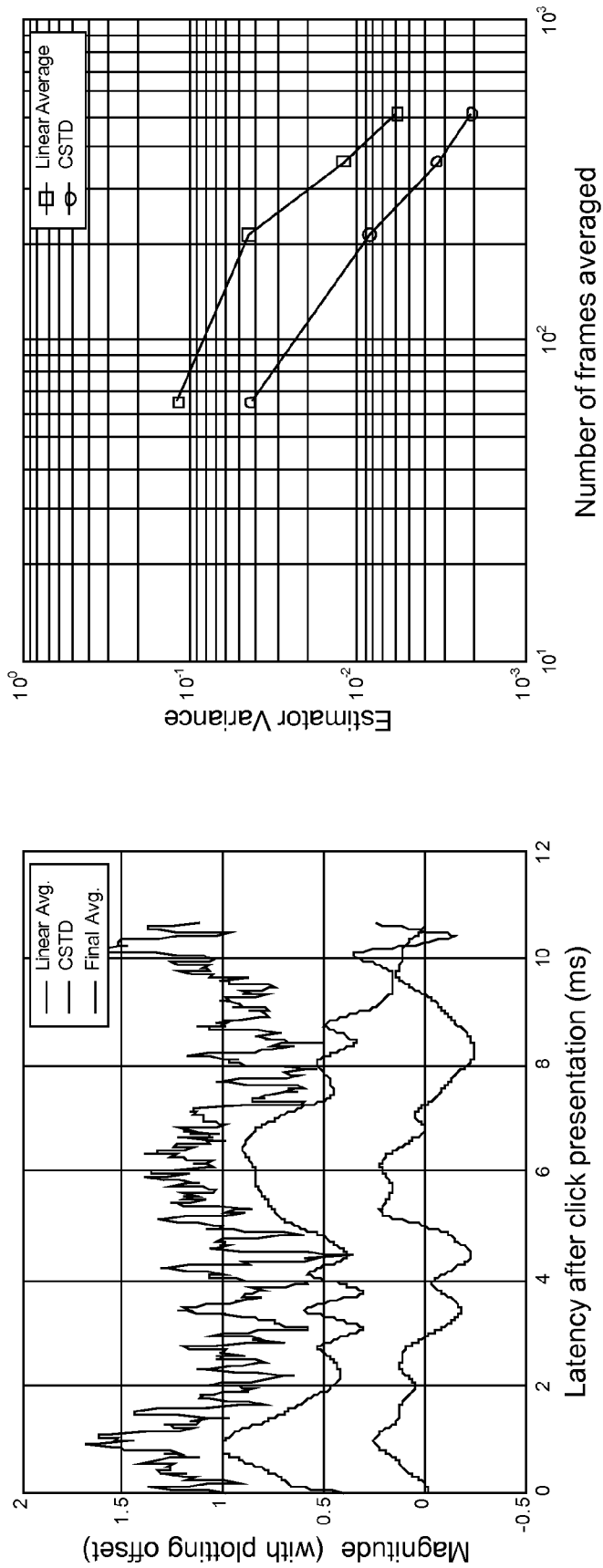
FIG. 46 is a series of graphs showing Ear 5 CSTD (left) and variance comparison (right)
Figure 47:
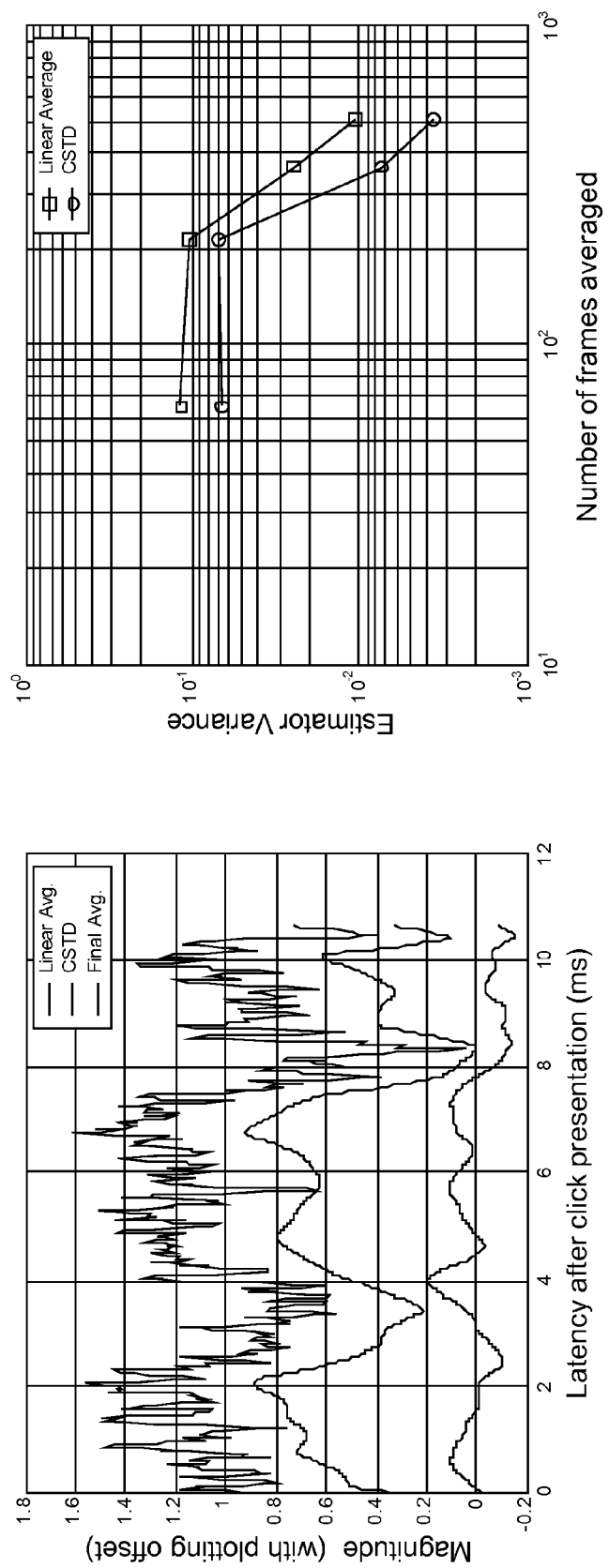
FIG. 47 is a series of graphs showing Ear 6 CSTD (left) and variance comparison (right)
Figure 48:
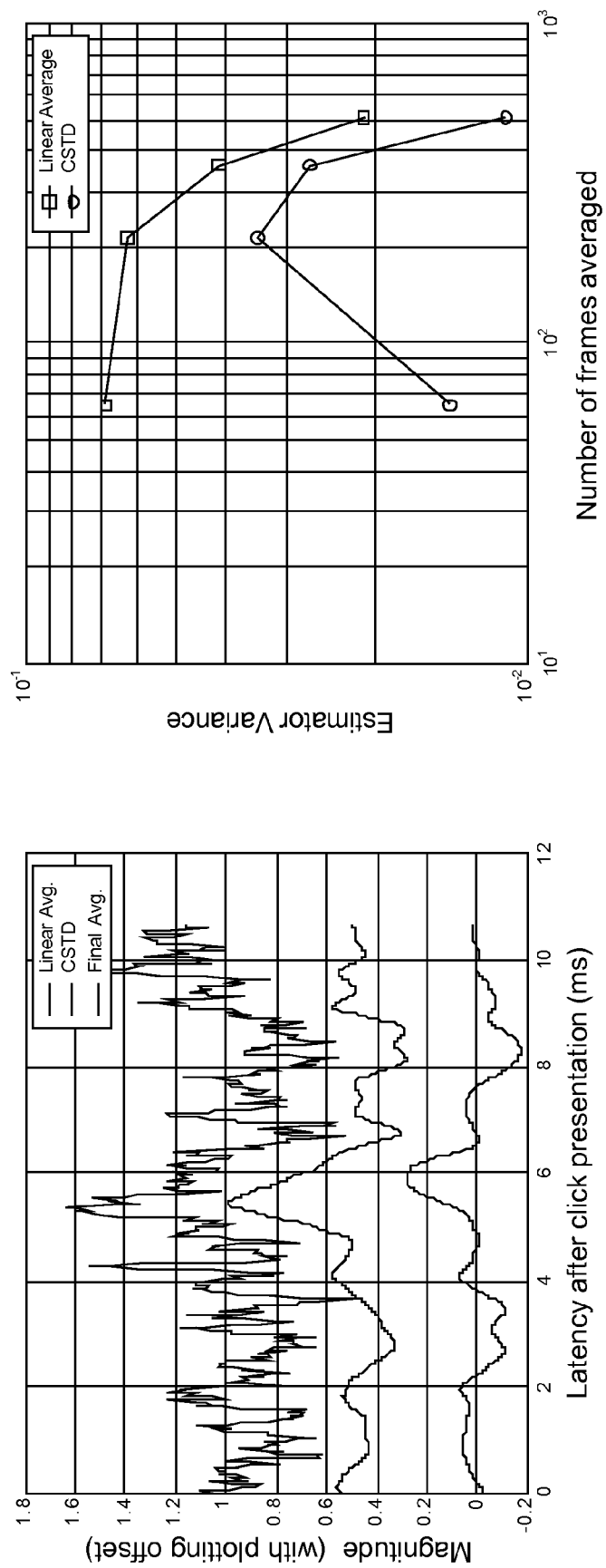
FIG. 48 is a series of graphs showing Ear 7 CSTD (left) and variance comparison (right)
Figure 49:
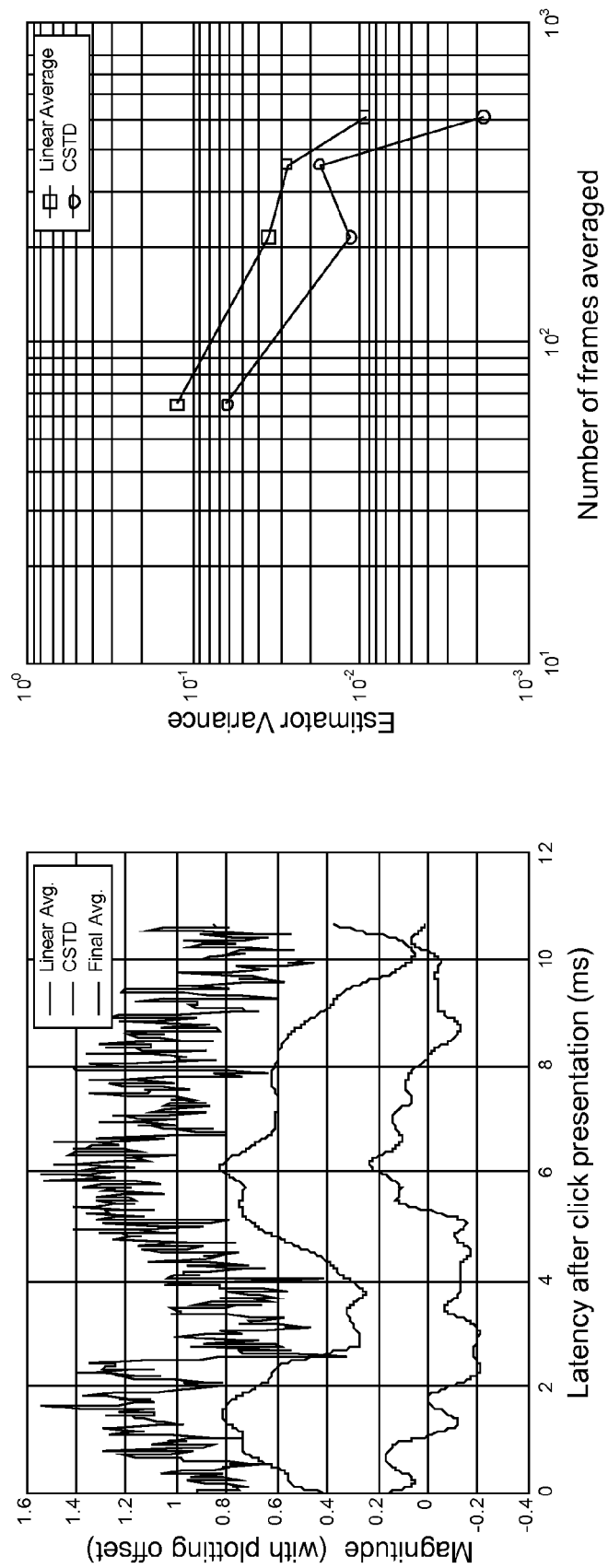
FIG. 49 is a series of graphs showing Ear 8 CSTD (left) and variance comparison (right)
Figure 51:
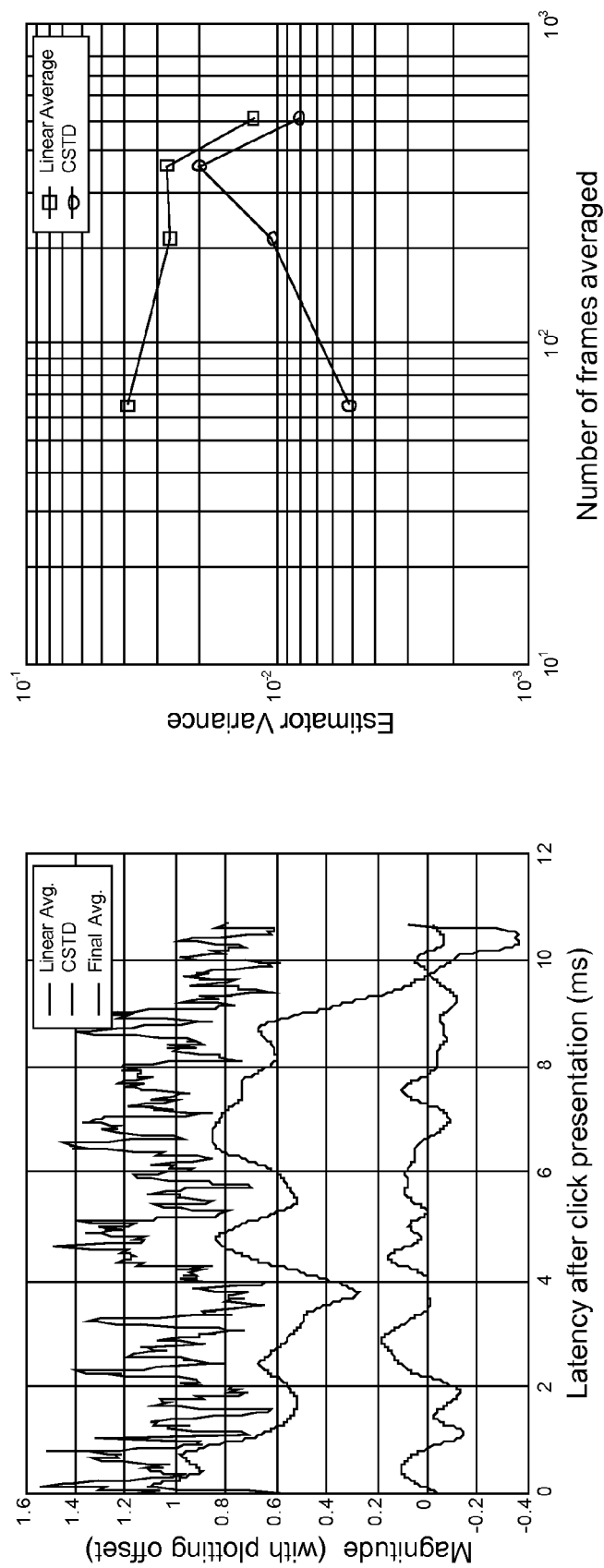
FIG. 51 is a series of graphs showing Ear 10 CSTD (left) and variance comparison (right)
Figure 52:
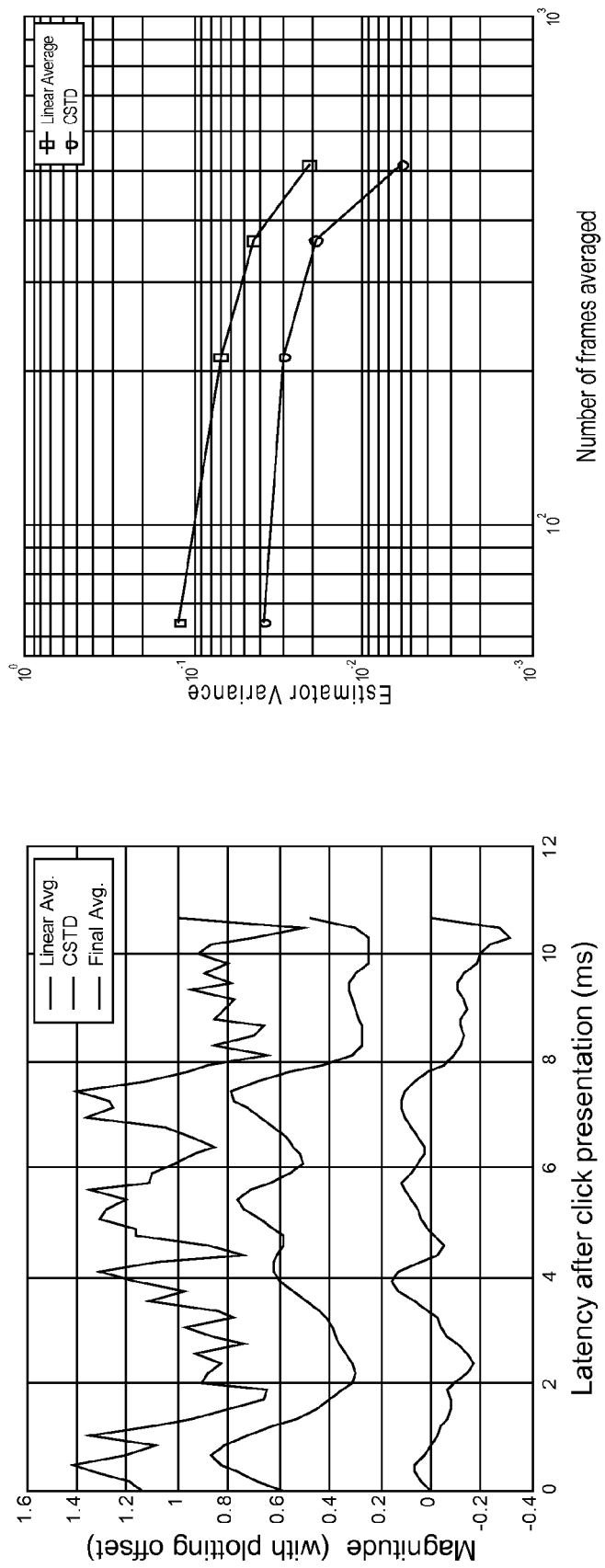
FIG. 52 is a series of graphs showing downsampled data for Ear 6 CSTD (left) and variance comparison (right)

The first choice is a constant function, such that $\delta_k=\delta_{k-1}$ for all k such that $1 \leq k \leq \log_2(N)$. Second major choice to be made is whether the function is increasing or decreasing. Then we choose the way the function increases (decreases), at what rate, in what manner, etc. Both of these hypotheses were tested by applying them to human subject data, and the results clearly indicate that starting with a large delta and decreasing it at each level yields substantially lower variance and RMS error. In addition, the threshold function $\delta^k=2^{-k/2}$ yields the best overall results. This is shown in FIG. 22 below, for typical human subject ABR data:

The result of FIG. 22 demonstrates that the decreasing function $2^{-k/2}$ yields an overall lowest error. It also demonstrates that there exists a minimum for each particular threshold function, which depends on the choice of the initial threshold. This means that the choice of initial threshold below which to set the coefficients to zero is very important, because a very large threshold keeps too many noise-related coefficients, and a very small threshold eliminates coefficients related to the information-bearing signal.

Two choices were possible with regard to the application of the wavelet transform operation within the CSTD algorithm (which created M new frames). One choice was to perform the DWT, de-noise, and then perform an IDWT on each individual frame of all the newly created frames. This would keep all the intermediate frame recombinations in the time domain, however, this required 2*M operations of the order of n*log$_2$(n) (n=64 samples per frame) just for the DWT and IDWT. An alternate way was to first calculate the M different DWTs for each frame, and then use only the wavelet coefficients in CSTD, without performing an IDWT each time. At the output of the CSTD, a single final frame of wavelet coefficients was obtained, and the IDWT was applied only once. This reduced the workload from 2*M to M+1 operations, with respect to performing the wavelet transforms.

We now present the overall algorithm, that combined the ABR signal acquisition and the novel methods of the preferred embodiment. The overall algorithm was as follows:
1. Acquire ABR data from human subjects over 8,192 frames, with and without stimulus presentation using the data acquisition system described above.
2. Create an array of wavelet coefficients by performing a DWT on each frame of the 8,192 frames, arranged like original frames [1, 2, ..., K].
3. Create the "final average" by linearly averaging all 8,192 frames, and filtering to obtain a smooth signal to be used as the "true" ABR signal.
4. De-noise the array of wavelet coefficients using CSTD, to obtain a total of $M=N*\log_2(N)$ new frames, each de-noised differently. (i.e., at most 8,192*13=106,496 frames).
5. Create P new permutations p of the original wavelet coefficient frames using the Euler-Fermat reorderings, to obtain rearranged frames (i.e., [3, 5, 9, ..., N, N−3, ...] of size N). Repeat CSTD operation P times for each new permutation p. This will obtain a total of $0.5*(N^2*\log_2(N))$ new frames.
6. Linearly average all different de-noised reorderings of frames to which CSTD has been applied to obtain a sequence of N frames.
7. Linearly average the N frames to obtain one frame of wavelet coefficients
8. Perform the IDWT on this averaged frame to obtain time domain samples.
9. Calculate the variance and the RMS error between the linear average and final average and compare to the variance and RMS error between de-noised average and final average, for an increasing number of frames.

The effect of Euler-Fermat permutations was investigated, and it was found that the additional frames did not contribute to the performance significantly. The average reduction in variance over linear averaging for the case of a single permutation was a factor of 9.25, while the application of 15 different Euler-Fermat permuations only increased that factor to 9.52, or approximately 3% improvement. This is an indication that the application of CSTD provides a sufficient number of frames to take advantage of the step-by-step de-noising, and that repeating CSTD for various rearrangements of frames does not yield a significant improvement.

However, while the new CSTD frames were not a simple linear combination of the original frames, they were correlated to the original frames to some degree, and not statistically independent. This is the major reason that the amount of SNR improvement using CSTD, while important, is significantly less than the best case theoretically expected result.

Also, the CSTD process is a combination of a linear averaging process and a de-noising process. The key difference between CSTD and linear averaging is that the CSTD sets wavelet coefficients less than a threshold to zero. Setting the threshold to zero in a CSTD process, means that all the wavelet coefficients are kept, and this is analogous to performing linear averaging. Thresholds are reduced as the number of CSTD levels increases. The number of levels, or the depth of the CSTD tree, increases with an increasing number of frames, hence more frames are processed by smaller thresholds while being linearly averaged at the same time. Hence, when compared to linear averaging, for a small number of frames, CSTD de-noises more frames with larger thresholds, while for a large number of frames, CSTD de-noises more frames with very small thresholds as compared to the number of frames that are being linearly averaged. Hence the CSTD approaches linear averaging performance for a very large number of frames.

Furthermore, the linear averaging processes embedded in CSTD from one tree level to the next tree level increases the SNR in addition to the simultaneous wavelet de-noising process. Hence, for a small number of frames, a small amount of linear averaging takes place within CSTD, and most of the SNR improvement comes from setting select wavelet coefficients to zero. As the number of frames increases, more linear averaging is performed within CSTD, and more noise is removed by the linear averaging process, than by wavelet de-noising. In addition, as more frames are processed, a smaller threshold is applied at the new tree levels. Overall, in each tree column, with an increasing number of frames, less noise is removed by de-noising because the thresholds are reduced from level to level, while more noise is removed by linear averaging.

Thus, when we compare the linear averaging process applied by itself, to the CSTD process, which also uses linear averaging as an integral part, we see that the amount of improvement is generally reduced with an increasing number of frames. However, with ABR signal processing, we are concerned with SNR improvement for a small number of frames (i.e., 512 vs. 8,192), hence the CSTD algorithm does offer an improvement when compared to conventional linear averaging.

This invention presents a novel fast wavelet estimator for application to weak biosignals. Weak biosignals are defined as signals produced by the human body and corrupted by a large amount of noise, such that the resulting signal-to-noise ratio (SNR) is below zero dB. Linear averaging of many signal frames is universally used in the prior art to increase the SNR of ABRs. Conventional wavelet de-noising is the process of setting wavelet coefficients that represent the noise to zero, while keeping the coefficients that represent the signal, using a threshold function. However, conventional wavelet de-noising fails for signals whose SNR is below zero, because too many wavelet coefficients are reduced to zero.

Using the apparatus and method of the present invention, the original data frames are recombined to create a large number of new frames, each of which was de-noised using a variable threshold function. Several algorithms for creation of new frame combinations are disclosed, and cyclic-shift tree de-noising (CSTD) is applied to these frames. This CSTD algorithm used the original N frames of data and produced $N*\log_2(N)$ new frames. The new frames were derived by averaging adjacent original frames, and de-noising the average. New levels of frames were created, and at each level different de-noising thresholds are employed. Since de-noising is a non-linear operation, the CSTD algorithm produces new frames that are not a linear combination of the original frames. The experimental results showed that permutation methods to first reorder the original frames, and then recombine them using CSTD did not produce a significant improvement.

Using the CSTD algorithm, it has been shown that applying the novel algorithm to a simulated noisy sinusoid with SNR of −20 dB achieves acceptable performance within the first 512 frames. For a small number of frames (i.e., 512) of the simulated signal the novel algorithm has been shown to reduce the variance of the estimate by a factor of approximately ten, when compared to linear averaging. The application of the novel algorithm to human subject ABR data has also produced a large improvement in performance. The area of ABR waveforms in the neighborhood of peak V collected in sub-optimal conditions, can be approximated by the novel algorithm in as few as 512 frames, as compared to linear averaging which requires on the order of 2-3 times more frames to be averaged. The novel algorithm has been shown to reduce the variance of the signal by a factor of approximately three when compared to linear averaging. This is equivalent to reducing the number of frames that need to be collected and averaged by a factor of approximately five.

The novel algorithm has several limitations. Like linear averaging, it cannot be applied to a single frame of data, hence multiple measurements of the same signal must be made. The signal being estimated must be coherent and smooth, when compared to the noise that corrupts it, because this is the basis of wavelet de-noising. Finally, the algorithm in its current implementation requires that all the frames of data be collected and stored prior to the application of the algorithm (i.e., for processing 512 frames, all of the 512 frames must be available in memory).

The novel CSTD algorithm can be applied to other classes of weak signals and biosignals. For example, an input signal that in variant in the sense that it irregularly varies or is aperiodic or is not repetitive may also be de-noised using the present invention using the same signal processor and method. All that is needed is that the input signal be selectively divided up into a number of smaller portions, each of which may then be separately de-noised and the resultant signal may then be re-assembled by reversing the procedure for dividing to thereby produce a de-noised variant signal. The goal of the preferred embodiment is to produce an algorithm that can be applied to universal infant hearing screening, where speed of testing and accuracy of results are of critical importance.

In view of the above, the several objects of the invention are achieved and other advantageous results attained. As various other changes could be made in the above without departing from the scope of the invention, it is intended that all matter contained in the above-description and shown in the accompanying drawings shall be interpreted as illustrative and not in any limiting sense. The invention therefore shall be limited solely by the scope of the claims set forth below.

What is claimed is:

1. A signal processor for de-noising an input signal, said signal processor including a memory for storing said input signal as an array A1 of a plurality of component frames, and a processor configured to:
   (a) perform a wavelet transform on each of said component frames to thereby create a corresponding array of wavelet coefficients;
   (b) iteratively for at least one repetition (i) combine multiple numbers of said wavelet coefficients into a plurality of resultant wavelet coefficients forming an array A2 of a like number $2^N$ of wavelet coefficients, each of said resultant wavelet coefficients being formed from a different combination of wavelet coefficients determined from the original set of wavelet coefficients or the previous iteration, as appropriate; and (ii) wavelet de-noising each resultant wavelet coefficient of array A2; and
   (c) combine the resultant wavelet coefficients resulting from the last iteration to form a combined resultant wavelet coefficient.

2. The signal processor of claim 1 wherein said input signal is characterized by a relatively low signal to noise ratio, and wherein said processor is configured to combine different wavelet coefficients to create each resultant wavelet coefficient.

3. The signal processor of claim 2 wherein said processor is configured to use a different threshold for discrete wavelet de-noising in each iteration.

4. The signal processor of claim 2 wherein said processor is configured to combine adjacent pairs of wavelet coefficients in a cyclic manner to create at least some of the resultant wavelet coefficients.

5. The signal processor of claim 2 wherein the processor is configured to combine the final array of iterated wavelet coefficients by averaging them.

6. The signal processor of claim 2 wherein the processor is configured to combine said wavelet coefficients by Euler-Fermat reordering.

7. The signal processor of claim 2 wherein the processor is configured to combine said wavelet coefficients by creating all mathematical permutations thereof to produce N! frames of wavelet coefficients.

8. A method for de-noising an input signal, said method utilizing a signal processor including a memory for storing said input signal as an array A1 of $2^N$ component frames, said method comprising the steps of:
   (a) performing a discrete wavelet transform on each of said component frames to thereby determine a corresponding array of wavelet coefficients;
   (b) iteratively for N−1 repetitions (i) combining multiple numbers of the wavelet coefficients determined from the previous step or iteration, as appropriate, into a plurality of resultant wavelet coefficients forming an array A2 of a like number $2^N$ of wavelet coefficients, each of said resultant wavelet coefficients being formed from a different combination of wavelet coefficients; and (ii) wavelet de-noising each wavelet coefficient of array A2; and
   (c) combining the resultant wavelet coefficients resulting from the iteration to form a combined resultant wavelet coefficient; and
   (d) performing an inverse discrete wavelet transform on the combined resultant wavelet coefficient to thereby produce the de-noised input signal.

9. The method of claim 8 wherein said input signal is characterized by a relatively low signal to noise ratio, and further comprising the step of combining different wavelet coefficients to create each resultant wavelet coefficient.

10. The method of claim 9 further comprising the step of using a different threshold for discrete wavelet de-noising in each iteration.

11. The method of claim 9 further comprising the step of combining adjacent pairs of wavelet coefficients in a cyclic manner to create at least some of the resultant wavelet coefficients.

12. The method of claim 9 further comprising the step of combining the final array of iterated wavelet coefficients by averaging them.

13. The method of claim 9 further comprising the step of combining said wavelet coefficients by Euler-Fermat reordering.

14. The method of claim 9 further comprising the step of combining said wavelet coefficients by creating all mathematical permutations thereof to produce N! wavelet coefficients.

* * * * *